United States Patent
Novak, III et al.

(10) Patent No.: US 12,342,860 B2
(45) Date of Patent: Jul. 1, 2025

(54) HEATER AND LIQUID TRANSPORT FOR AN AEROSOL DELIVERY SYSTEM

(71) Applicant: RAI Strategic Holdings, Inc., Winston-Salem, NC (US)

(72) Inventors: Charles Jacob Novak, III, Winston-Salem, NC (US); Matthew Joel Nettenstrom, Bartlett, IL (US); Steven Michael Schennum, Plainfield, IL (US); Thomas Michael McKeon, Wheaton, IL (US); Zachary Hy Burchman, Chicago, IL (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 1352 days.

(21) Appl. No.: 16/598,505

(22) Filed: Oct. 10, 2019

(65) Prior Publication Data
US 2020/0113243 A1   Apr. 16, 2020

Related U.S. Application Data

(60) Provisional application No. 62/744,978, filed on Oct. 12, 2018.

(51) Int. Cl.
*A24F 40/42* (2020.01)
*A24B 15/167* (2020.01)
(Continued)

(52) U.S. Cl.
CPC ............ *A24F 40/42* (2020.01); *A24B 15/167* (2016.11); *A24D 1/002* (2013.01); *A24D 1/14* (2013.01);
(Continued)

(58) Field of Classification Search
CPC .......... A24F 40/10; A24F 40/42; A24F 40/40; A24F 40/46; A24F 40/50; A24F 40/485;
(Continued)

(56) References Cited

U.S. PATENT DOCUMENTS

| 2,057,353 A | 10/1936 | Whittemore, Jr. |
| 2,104,266 A | 1/1938 | McCormick |

(Continued)

FOREIGN PATENT DOCUMENTS

| CL | 2012003241 A1 | 9/2013 |
| CL | 2017001137 A1 | 1/2018 |

(Continued)

OTHER PUBLICATIONS

Liu, Atomizer, Mar. 27, 2015, Foreign Translation relied upon (Year: 2015).*

(Continued)

*Primary Examiner* — Michael H. Wilson
*Assistant Examiner* — Stephanie Lynn Moore
(74) *Attorney, Agent, or Firm* — Womble Bond Dickinson (US) LLP

(57) ABSTRACT

The present disclosure relates to an aerosol delivery device. In some implementations, the aerosol delivery device may comprise a control device and a cartridge having a mouthpiece portion and a tank portion with respective proximal and distal ends, the tank portion being configured to contain a liquid composition, and the cartridge further including a liquid transport element and an atomizing member. At least a portion of the liquid transport element may be positioned proximate the atomizing member, and at least a portion of the atomizing member may be positioned proximate the distal end of the mouthpiece portion. In other implementations, at least a portion of the atomizing member may be positioned above the proximal end of the tank portion. In
(Continued)

still other implementations, at least a portion of the atomizing member may be positioned between the proximal end of the tank portion and the distal end of the tank portion.

13 Claims, 45 Drawing Sheets

(51) Int. Cl.
*A24D 1/00* (2020.01)
*A24D 1/14* (2006.01)
*A24F 7/00* (2006.01)
*A24F 7/02* (2006.01)
*A24F 40/40* (2020.01)
*A24F 40/46* (2020.01)
*A61M 11/04* (2006.01)
*H01R 13/17* (2006.01)
*H01R 13/62* (2006.01)
*H05B 3/20* (2006.01)

(52) U.S. Cl.
CPC .............. *A24F 7/00* (2013.01); *A24F 7/02* (2013.01); *A24F 40/46* (2020.01); *A61M 11/042* (2014.02); *H01R 13/17* (2013.01); *H01R 13/6205* (2013.01); *H05B 3/20* (2013.01); *A24F 40/40* (2020.01); *A61M 11/041* (2013.01); *A61M 2205/0288* (2013.01); *A61M 2205/3368* (2013.01); *A61M 2205/50* (2013.01); *A61M 2205/584* (2013.01); *A61M 2205/587* (2013.01); *A61M 2205/8206* (2013.01); *H05B 2203/021* (2013.01)

(58) Field of Classification Search
CPC .......... A24F 40/20; A24F 40/60; A24F 40/44; A24F 40/53; A24F 40/90; A24F 40/70; A24F 40/30; A24F 40/48; A24F 40/00; A24F 40/51; A24F 40/65; A24F 13/04; A24F 40/05; A24F 47/00; A24F 7/02; A24F 1/32; A24F 15/12; A24F 40/57; A24F 40/85; A24F 42/10; A24F 42/60; A24F 7/00; A61M 15/06; A61M 11/042; A61M 11/041

See application file for complete search history.

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,060,671 A | 10/1991 | Counts et al. | |
| 5,093,894 A | 3/1992 | Deevi et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 8,528,569 B1 | 9/2013 | Newton | |
| 8,833,364 B2 | 9/2014 | Buchberger | |
| 8,950,395 B2 | 2/2015 | Schennum | |
| 9,220,304 B2 | 12/2015 | Greim | |
| 9,462,831 B2 | 10/2016 | Liu | |
| 9,877,508 B2 | 1/2018 | Kane | |
| 10,015,990 B2 | 7/2018 | Mironov | |
| 10,028,537 B1 | 7/2018 | Hawes et al. | |
| 10,058,125 B2 | 8/2018 | Worm et al. | |
| 10,080,851 B2 | 9/2018 | Davidson et al. | |
| 10,085,481 B2 | 10/2018 | Verleur et al. | |
| 10,092,037 B2 | 10/2018 | Tucker et al. | |
| 10,104,913 B2 | 10/2018 | Lau et al. | |
| 10,117,463 B2 | 11/2018 | Thomas | |
| 10,117,467 B2 | 11/2018 | Hawes et al. | |
| 10,791,767 B2 | 10/2020 | Novak, III et al. | |
| 11,502,466 B2 | 11/2022 | Novak, III et al. | |
| 11,677,201 B2 | 6/2023 | Novak, III et al. | |
| 11,856,988 B2 | 1/2024 | Novak, III et al. | |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0151717 A1 | 6/2009 | Bowen et al. | |
| 2009/0188490 A1 | 7/2009 | Hon | |
| 2009/0272379 A1 | 11/2009 | Thorens et al. | |
| 2009/0320863 A1 | 12/2009 | Fernando et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0226236 A1* | 9/2011 | Buchberger | A61K 31/465 128/200.23 |
| 2011/0265806 A1 | 11/2011 | Alarcon et al. | |
| 2013/0037041 A1 | 2/2013 | Worm et al. | |
| 2013/0042865 A1 | 2/2013 | Monsees et al. | |
| 2013/0306084 A1 | 11/2013 | Flick | |
| 2013/0319435 A1 | 12/2013 | Flick | |
| 2014/0000638 A1 | 1/2014 | Sebastian et al. | |
| 2014/0076310 A1 | 3/2014 | Newton | |
| 2014/0096781 A1 | 4/2014 | Sears et al. | |
| 2014/0096782 A1 | 4/2014 | Ampolini et al. | |
| 2014/0109921 A1 | 4/2014 | Chen | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0270729 A1 | 9/2014 | DePiano et al. | |
| 2014/0366898 A1 | 12/2014 | Monsees et al. | |
| 2015/0020832 A1 | 1/2015 | Greim et al. | |
| 2015/0083147 A1* | 3/2015 | Schiff | A24F 40/44 131/329 |
| 2015/0128976 A1 | 5/2015 | Verleur et al. | |
| 2015/0150308 A1 | 6/2015 | Monsees et al. | |
| 2015/0164142 A1 | 6/2015 | Li et al. | |
| 2015/0181941 A1 | 7/2015 | Liu | |
| 2015/0208729 A1 | 7/2015 | Monsees et al. | |
| 2015/0216233 A1 | 8/2015 | Sears et al. | |
| 2015/0245659 A1 | 9/2015 | DePiano et al. | |
| 2015/0305406 A1 | 10/2015 | Li et al. | |
| 2015/0313283 A1 | 11/2015 | Collett et al. | |
| 2015/0313287 A1 | 11/2015 | Verleur et al. | |
| 2015/0335075 A1 | 11/2015 | Minskoff et al. | |
| 2016/0309786 A1 | 10/2016 | Holtz | |
| 2016/0338410 A1 | 11/2016 | Batista et al. | |
| 2016/0366947 A1 | 12/2016 | Monsees et al. | |
| 2017/0027226 A1 | 2/2017 | Mironov et al. | |
| 2017/0071256 A1 | 3/2017 | Verleur et al. | |
| 2017/0095005 A1 | 4/2017 | Monsees et al. | |
| 2017/0119060 A1 | 5/2017 | Li et al. | |
| 2017/0135404 A1 | 5/2017 | Reevell | |
| 2017/0135405 A1 | 5/2017 | Reevell | |
| 2017/0143042 A1 | 5/2017 | Batista et al. | |
| 2017/0215485 A1 | 8/2017 | Zitzke | |
| 2017/0231281 A1 | 8/2017 | Hatton et al. | |
| 2017/0231282 A1 | 8/2017 | Hatton et al. | |
| 2017/0258143 A1* | 9/2017 | Lederer | A24F 40/70 |
| 2017/0295844 A1 | 10/2017 | Thevenaz et al. | |
| 2017/0325289 A1 | 11/2017 | Liu | |
| 2017/0340011 A1 | 11/2017 | Batista | |
| 2017/0340012 A1 | 11/2017 | Mironov et al. | |
| 2017/0347711 A1 | 12/2017 | Litten et al. | |
| 2017/0347712 A1 | 12/2017 | Singh | |
| 2017/0360093 A1* | 12/2017 | Fernando | A24F 40/485 |
| 2017/0367402 A1 | 12/2017 | Lau et al. | |
| 2018/0000157 A1 | 1/2018 | Batista et al. | |
| 2018/0000160 A1 | 1/2018 | Taschner et al. | |
| 2018/0014575 A1 | 1/2018 | Fursa | |
| 2018/0020723 A1 | 1/2018 | Davis et al. | |
| 2018/0020731 A1 | 1/2018 | Rasmussen et al. | |

(56) References Cited

U.S. PATENT DOCUMENTS

| | | | |
|---|---|---|---|
| 2018/0020736 A1 | 1/2018 | Silvestrini |
| 2018/0027877 A1 | 2/2018 | Tucker et al. |
| 2018/0035717 A1 | 2/2018 | Batista |
| 2018/0042306 A1 | 2/2018 | Atkins et al. |
| 2018/0043114 A1 | 2/2018 | Bowen et al. |
| 2018/0077967 A1 | 3/2018 | Hatton et al. |
| 2018/0084831 A1 | 3/2018 | Mironov |
| 2018/0103685 A1 | 4/2018 | Yener |
| 2018/0132525 A1 | 5/2018 | Patil et al. |
| 2018/0140019 A1 | 5/2018 | Guo et al. |
| 2018/0168225 A1 | 6/2018 | Zinovik et al. |
| 2018/0168227 A1 | 6/2018 | Fraser et al. |
| 2018/0177230 A1 | 6/2018 | Hawes et al. |
| 2018/0213850 A1 | 8/2018 | Brinkley et al. |
| 2018/0228214 A1 | 8/2018 | McAdam et al. |
| 2018/0242643 A1 | 8/2018 | Silvestrini et al. |
| 2018/0279682 A1 | 10/2018 | Guo et al. |
| 2018/0280637 A1 | 10/2018 | Mayle et al. |
| 2018/0295888 A1 | 10/2018 | Newcomb et al. |
| 2018/0296777 A1 | 10/2018 | Terry et al. |

FOREIGN PATENT DOCUMENTS

| | | |
|---|---|---|
| CL | 2017003454 A1 | 6/2018 |
| CL | 2021000899 A1 | 9/2021 |
| CL | 2021000900 A1 | 9/2021 |
| CN | 1541577 | 11/2004 |
| CN | 2719043 | 8/2005 |
| CN | 201379072 | 1/2010 |
| CN | 102014677 A | 4/2011 |
| CN | 105559150 A | 5/2016 |
| CN | 106255430 A | 12/2016 |
| CN | 106263031 A | 1/2017 |
| CN | 106998819 A | 8/2017 |
| CN | 206403199 U | 8/2017 |
| CN | 207011690 U | 2/2018 |
| CN | 17890142 B | 4/2018 |
| CN | 207306069 U | 5/2018 |
| EP | 1 618 803 | 1/2006 |
| EP | 2113178 A1 | 11/2009 |
| KR | 10-2018-0048847 A | 5/2018 |
| TW | 201825827 A | 7/2018 |
| WO | WO 2004/080216 | 9/2004 |
| WO | WO 2005/099494 | 10/2005 |
| WO | WO 2007/131449 | 11/2007 |
| WO | 2016/005533 A1 | 1/2016 |
| WO | WO 2016/026811 | 2/2016 |
| WO | 2016/096497 A1 | 6/2016 |
| WO | 2016/154797 A1 | 6/2016 |
| WO | WO 2017/051006 | 9/2016 |
| WO | 2016/172907 A1 | 11/2016 |
| WO | 2016/197485 A1 | 12/2016 |
| WO | WO 2017/207442 | 5/2017 |
| WO | 2017/163046 A1 | 9/2017 |
| WO | 2018/048813 A1 | 3/2018 |
| WO | WO 2018/167166 | 9/2018 |
| WO | WO 2018/202732 | 11/2018 |

OTHER PUBLICATIONS

Partial International Search Report from corresponding International Appl. No. PCT/IB2019/058710, dated Jan. 17, 2020.

* cited by examiner

HEATER AND LIQUID TRANSPORT FOR AN AEROSOL DELIVERY SYSTEM

CROSS-REFERENCE TO RELATED APPLICATIONS

This application claims priority to, and the benefit of, U.S. Provisional Patent Application No. 62/744,978, titled Aerosol Forming Device, filed on Oct. 12, 2018, which is incorporated herein in its entirety by reference.

TECHNOLOGY FIELD

The present disclosure relates to aerosol delivery devices such as smoking articles, and more particularly to aerosol delivery devices that may utilize electrical power for the production of aerosol (e.g., smoking articles commonly referred to as electronic cigarettes). The smoking articles may be configured to vaporize an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. App. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety. It would be desirable to provide an aerosol delivery device with advantageous usability features.

BRIEF SUMMARY

The present disclosure relates to aerosol delivery devices, methods of forming such devices, and elements of such devices. The disclosure particularly relates to an aerosol delivery device. In this regard, various embodiments of the disclosure provide an aerosol delivery device with advantageous usability features. The present disclosure includes, without limitation, the following example implementations:

An aerosol delivery device comprising a control device that includes an outer housing defining an outer wall and having a proximal end and a distal end, the proximal end of the control device defining a cartridge receiving chamber, the control device further including a power source and a control component, and a cartridge that includes a mouthpiece portion and a tank portion, the mouthpiece portion and the tank portion having respective proximal and distal ends, the tank portion being configured to contain a liquid composition, the cartridge further including an atomizing member and a liquid transport element, wherein a portion of the cartridge is configured to be removably coupled with the cartridge receiving chamber of the control device, wherein at least a portion of the liquid transport element is located proximate the atomizing member, wherein the atomizing member is configured to vaporize the liquid composition to generate an aerosol, and wherein at least a portion of the atomizing member is positioned above the proximal end of the tank portion.

The aerosol delivery device of any preceding example implementation, or any combination of any preceding example implementations, wherein the atomizing member comprises a heating member, and wherein the heating member is configured to heat the liquid composition to generate the aerosol.

The aerosol delivery device of any preceding example implementation, or any combination of any preceding example implementations, the cartridge further including a second liquid transport element, and wherein the second liquid transport element is configured to transport liquid to the first liquid transport element.

The aerosol delivery device of any preceding example implementation, or any combination of any preceding example implementations, wherein at least a portion of the heating member is positioned between the distal end of the mouthpiece portion and the proximal end of the tank portion.

The aerosol delivery device of any preceding example implementation, or any combination of any preceding example implementations, wherein the cartridge further includes a collar portion disposed between the mouthpiece portion and the tank portion, and wherein at least a portion of the heating member is located within the collar portion.

The aerosol delivery device of any preceding example implementation, or any combination of any preceding example implementations, wherein the heating member comprises a flat heating member installed in a curved orientation, wherein the second liquid transport element defines a longitudinal portion that intersects a curved transverse portion, and wherein a length of the longitudinal portion of the second liquid transport element is longer than a length of the transverse portion.

The aerosol delivery device of any preceding example implementation, or any combination of any preceding example implementations, further comprising a curved hood feature, wherein the curvature of the hood feature opposes the curvature of the heating member.

The aerosol delivery device of any preceding example implementations, or any combination of any preceding example implementations, wherein the heating member comprises a flat heating member installed in a curved orientation, wherein the second liquid transport element defines a longitudinal portion that intersects a curved transverse portion, and wherein a length of the transverse portion of the second liquid transport element is longer than a length of the longitudinal portion.

The aerosol delivery device of any preceding example implementation, or any combination of any preceding example implementations, further comprising a curved hood feature, wherein the curvature of the hood feature opposes the curvature of the heating member.

The aerosol delivery device of any preceding example implementation, or any combination of any preceding example implementations, wherein the heating member comprises a coil heating member, wherein the first liquid transport element has a U-shape defining a central portion and two opposite leg portions, wherein a portion of the heating member is wrapped around at least the central portion of the first liquid transport element, wherein the second liquid transport element defines a longitudinal portion that intersects a transverse portion, and wherein a length of the longitudinal portion of the second transport element is longer than a length of the transverse portion.

The aerosol delivery device of any preceding example implementation, or any combination of any preceding example implementations, wherein the heating member comprises a coil heating member, wherein the first liquid transport element has a U-shape defining a central portion and two opposite leg portions, wherein a portion of the heating member is wrapped around at least the central portion of the first liquid transport element, wherein the second liquid transport surrounds both of the legs of the first liquid transport element, and wherein a length of the legs of the first liquid transport element is longer than a length of the central portion of the first liquid transport element.

The aerosol delivery device of any preceding example implementation, or any combination of any preceding example implementations, wherein the heating member comprises a coil heating member, wherein the first liquid transport element has a cylindrical shape and is substantially aligned with a longitudinal axis of the cartridge, wherein a portion of the heating member is wrapped around at least a portion of the first liquid transport element, and wherein the second liquid transport element has a cylindrical shape and is substantially aligned with a longitudinal axis of the cartridge.

The aerosol delivery device of any preceding example implementation, or any combination of any preceding example implementations, wherein the second liquid transport element is substantially solid, and wherein a length of the second liquid transport element is longer than a length of the first liquid transport element portion.

The aerosol delivery device of any preceding example implementation, or any combination of any preceding example implementations, wherein the second liquid transport element is hollow, wherein the second liquid transport element surrounds at least a portion of the first liquid transport element, and wherein a length of the first liquid transport element is longer than a length of the second liquid transport element.

The aerosol delivery device of any preceding example implementation, or any combination of any preceding example implementations, wherein the first liquid transport element is hollow and comprises a ceramic material.

The aerosol delivery device of any preceding example implementation, or any combination of any preceding example implementations, wherein the first liquid transport comprises at least one of a cotton material and a silica material.

The aerosol delivery device of any preceding example implementation, or any combination of any preceding example implementations, wherein the heating member comprises a coil heating member, wherein the first liquid transport element has a cylindrical shape and is substantially aligned with a longitudinal axis of the cartridge, wherein a portion of the heating member is embedded within at least a portion of the first liquid transport element, and wherein the second liquid transport element has a cylindrical shape and is substantially aligned with a longitudinal axis of the cartridge.

The aerosol delivery device of any preceding example implementation, or any combination of any preceding example implementations, wherein the second liquid transport element is substantially solid, and wherein a length of the second liquid transport element is longer than a length of the first liquid transport element portion.

The aerosol delivery device of any preceding example implementation, or any combination of any preceding example implementations, wherein the second liquid transport element is hollow, wherein the second liquid transport element surrounds at least a portion of the first liquid transport element, and wherein a length of the first liquid transport element is longer than a length of the second liquid transport element.

The aerosol delivery device of any preceding example implementation, or any combination of any preceding example implementations, wherein the heating member comprises a flat heating member, wherein the second liquid transport element comprises a plurality of capillary tubes, wherein the heating member and the first liquid transport element are substantially aligned with a transverse axis of the cartridge, and wherein the plurality of capillary tubes are substantially aligned with a longitudinal axis of the cartridge.

The aerosol delivery device of any preceding example implementation, or any combination of any preceding example implementations, wherein the plurality of capillary tubes comprises a pair of spaced capillary tubes.

The aerosol delivery device of any preceding example implementation, or any combination of any preceding example implementations, wherein the plurality of capillary tubes comprises five spaced capillary tubes arranged in a cross pattern.

The aerosol delivery device of any preceding example implementation, or any combination of any preceding example implementations, wherein the heating member comprises a flat heating member, wherein the second liquid transport element defines a longitudinal portion that intersects a transverse portion, and wherein a length of the longitudinal portion of the second liquid transport element is longer than a length of the transverse portion.

The aerosol delivery device of any preceding example implementation, or any combination of any preceding example implementations, wherein the cartridge further includes a collar portion disposed between the mouthpiece portion and the tank portion.

The aerosol delivery device of any preceding example implementation, or any combination of any preceding example implementations, wherein the atomizing member is located at least partially within the collar portion.

The aerosol delivery device of any preceding example implementation, or any combination of any preceding example implementations, wherein the atomizing member comprises a heating member configured to heat the liquid composition to generate the aerosol, and further comprising a hood feature positioned proximate the heating member, wherein the hood feature is located at least partially within the mouthpiece portion.

An aerosol delivery device comprising a control device that includes an outer housing defining an outer wall and having a proximal end and a distal end, the proximal end of the control device defining a cartridge receiving chamber, the control device further including a power source and a control component, and a cartridge that includes a mouthpiece portion and a tank portion, the mouthpiece portion and the tank portion having respective proximal and distal ends, the tank portion being configured to contain a liquid composition, the cartridge further including a first liquid transport element, a second liquid transport element, and an atomizing member, wherein a portion of the cartridge is configured to be removably coupled with the cartridge receiving chamber of the control device, wherein the atomizing member is configured to vaporize the liquid composition to generate an aerosol, wherein at least a portion of the atomizing member is positioned between the proximal end of the tank portion and the distal end of the tank portion, wherein at least a portion of the first liquid transport element is positioned below the atomizing member, wherein the second liquid transport element is disposed below the first liquid transport element, and wherein the second liquid transport element is configured to transport liquid to the first liquid transport element.

The aerosol delivery device of any preceding example implementation, or any combination of any preceding example implementations, wherein the atomizing member comprises a heating member, and wherein the heating member is configured to heat the liquid composition to generate the aerosol.

The aerosol delivery device of any preceding example implementation, or any combination of any preceding example implementations, wherein the heating member comprises a flat heating member, and wherein the heating member is positioned proximate the distal end of the tank portion.

An aerosol delivery device comprising a control device that includes an outer housing defining an outer wall and having a proximal end and a distal end, the proximal end of the control device defining a cartridge receiving chamber, the control device further including a power source and a control component, and a cartridge that includes a mouthpiece portion and a tank portion, the mouthpiece portion and the tank portion having respective proximal and distal ends, the tank portion being configured to contain a liquid composition, the cartridge further including an atomizing member and a liquid transport element, wherein a portion of the cartridge is configured to be removably coupled with the cartridge receiving chamber of the control device, wherein at least a portion of the liquid transport element is located proximate the atomizing member, wherein the atomizing member is configured to vaporize the liquid composition to generate an aerosol, and wherein at least a portion of the atomizing member is positioned proximate the distal end of the mouthpiece portion.

The aerosol delivery device of any preceding example implementation, or any combination of any preceding example implementations, wherein the atomizing member comprises a heating member, and wherein the heating member is configured to heat the liquid composition to generate the aerosol.

The aerosol delivery device of any preceding example implementation, or any combination of any preceding example implementations, the cartridge further including a second liquid transport element, and wherein the second liquid transport element is configured to transport liquid to the first liquid transport element.

The aerosol delivery device of any preceding example implementation, or any combination of any preceding example implementations, wherein the heating member comprises a flat heating member installed in a curved orientation, wherein the second liquid transport element defines a longitudinal portion that intersects a curved transverse portion, and wherein a length of the longitudinal portion of the second liquid transport element is longer than a length of the transverse portion.

The aerosol delivery device of any preceding example implementation, or any combination of any preceding example implementations, further comprising a curved hood feature, wherein the curvature of the hood feature opposes the curvature of the heater.

The aerosol delivery device of any preceding example implementation, or any combination of any preceding example implementations, wherein the heating member comprises a flat heating member installed in a curved orientation, wherein the second liquid transport element defines a longitudinal portion that intersects a curved transverse portion, and wherein a length of the transverse portion of the second liquid transport element is longer than a length of the longitudinal portion.

The aerosol delivery device of any preceding example implementation, or any combination of any preceding example implementations, further comprising a curved hood feature, wherein the curvature of the hood feature opposes the curvature of the heater.

The aerosol delivery device of any preceding example implementation, or any combination of any preceding example implementations, wherein the heating member comprises a coil heating member, wherein the first liquid transport element has a U-shape defining a central portion and two opposite leg portions, wherein a portion of the heating member is wrapped around at least the central portion of the first liquid transport element, wherein the second liquid transport element defines a longitudinal portion that intersects a transverse portion, and wherein a length of the longitudinal portion of the second transport element is longer than a length of the transverse portion.

The aerosol delivery device of any preceding example implementation, or any combination of any preceding example implementations, wherein the heating member comprises a coil heating member, wherein the first liquid transport element has a U-shape defining a central portion and two opposite leg portions, wherein a portion of the heating member is wrapped around at least the central portion of the first liquid transport element, wherein the second liquid transport surrounds both of the legs of the first liquid transport element, and wherein a length of the legs of the first liquid transport element is longer than a length of the central portion of the first liquid transport element.

The aerosol delivery device of any preceding example implementation, or any combination of any preceding example implementations, wherein the heating member comprises a coil heating member, wherein the first liquid transport element has a cylindrical shape and is substantially aligned with a longitudinal axis of the cartridge, wherein a portion of the heating member is wrapped around at least a portion of the first liquid transport element, and wherein the second liquid transport element has a cylindrical shape and is substantially aligned with a longitudinal axis of the cartridge.

The aerosol delivery device of any preceding example implementation, or any combination of any preceding example implementations, wherein the second liquid transport element is substantially solid, and wherein a length of the second liquid transport element is longer than a length of the first liquid transport element portion.

The aerosol delivery device of any preceding example implementation, or any combination of any preceding example implementations, wherein the second liquid transport element is hollow, wherein the second liquid transport element surrounds at least a portion of the first liquid transport element, and wherein a length of the first liquid transport element is longer than a length of the second liquid transport element.

The aerosol delivery device of any preceding example implementation, or any combination of any preceding example implementations, wherein the first liquid transport element is hollow and comprises a ceramic material.

The aerosol delivery device of any preceding example implementation, or any combination of any preceding example implementations, wherein the first liquid transport element comprises at least one of a cotton material and a silica material.

The aerosol delivery device of any preceding example implementation, or any combination of any preceding example implementations, wherein the heating member comprises a coil heating member, wherein the first liquid transport element has a cylindrical shape and is substantially aligned with a longitudinal axis of the cartridge, wherein a portion of the heating member is embedded within at least a portion of the first liquid transport element, and wherein the second liquid transport element has a cylindrical shape and is substantially aligned with a longitudinal axis of the cartridge.

The aerosol delivery device of any preceding example implementation, or any combination of any preceding example implementation, wherein the second liquid transport element is substantially solid, and wherein a length of the second liquid transport element is longer than a length of the first liquid transport element portion.

The aerosol delivery device of any preceding example implementation, or any combination of any preceding example implementations, wherein the second liquid transport element is hollow, wherein the second liquid transport element surrounds at least a portion of the first liquid transport element, and wherein a length of the first liquid transport element is longer than a length of the second liquid transport element.

The aerosol delivery device of any preceding example implementation, or any combination of any preceding example implementations, wherein the heating member comprises a flat heating member, wherein the second liquid transport element comprises a plurality of capillary tubes, wherein the heating member and the first liquid transport element are substantially aligned with a transverse axis of the cartridge, and wherein the plurality of capillary tubes are substantially aligned with a longitudinal axis of the cartridge.

The aerosol delivery device of any preceding example implementation, or any combination of any preceding example implementations, wherein the plurality of capillary tubes comprises a pair of spaced capillary tubes.

The aerosol delivery device of any preceding example implementation, or any combination of any preceding example implementations, wherein the plurality of capillary tubes comprises five spaced capillary tubes arranged in a cross pattern.

The aerosol delivery device of any preceding example implementation, or any combination of any example implementations, wherein the heating member comprises a flat heating member, wherein the second liquid transport element defines a longitudinal portion that intersects a transverse portion, and wherein a length of the longitudinal portion of the second liquid transport element is longer than a length of the transverse portion.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
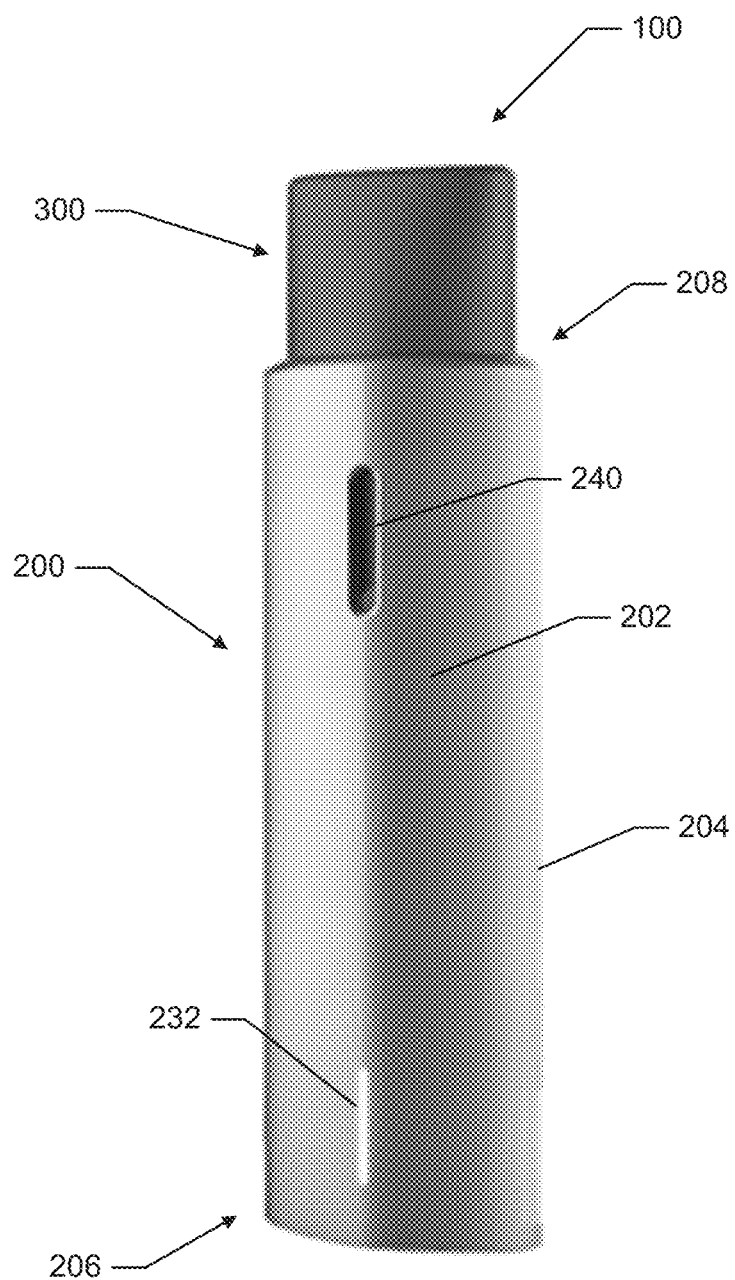
Figure 2:
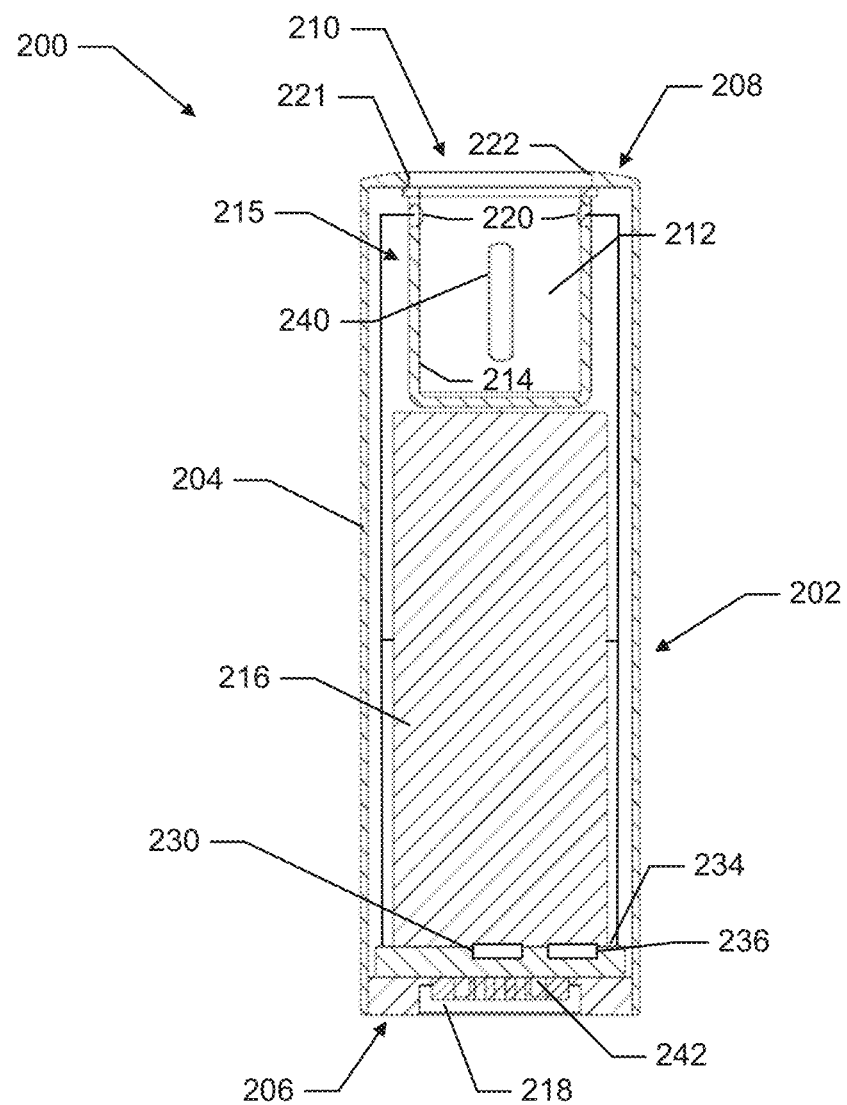
Figure 3A:
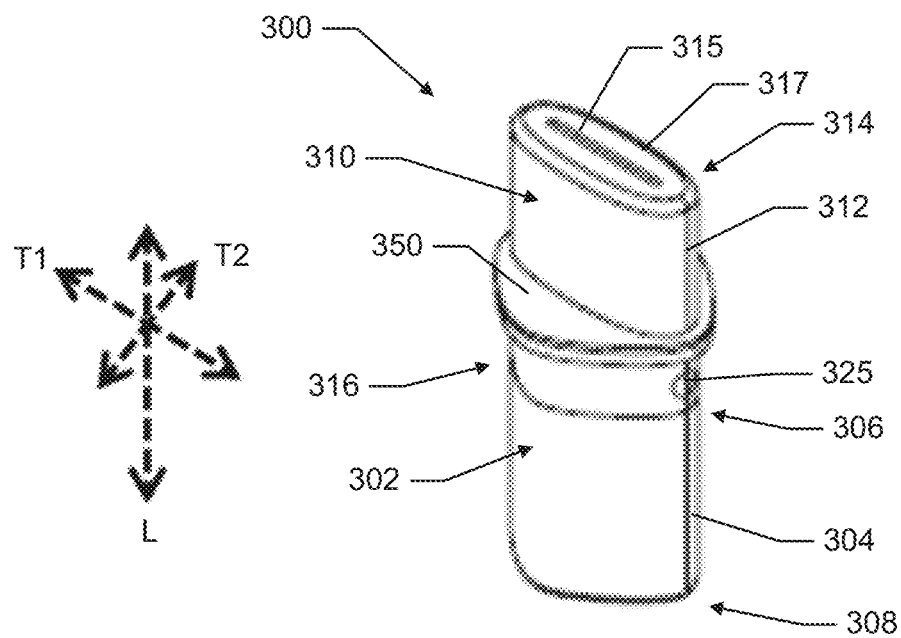
Figure 3B:
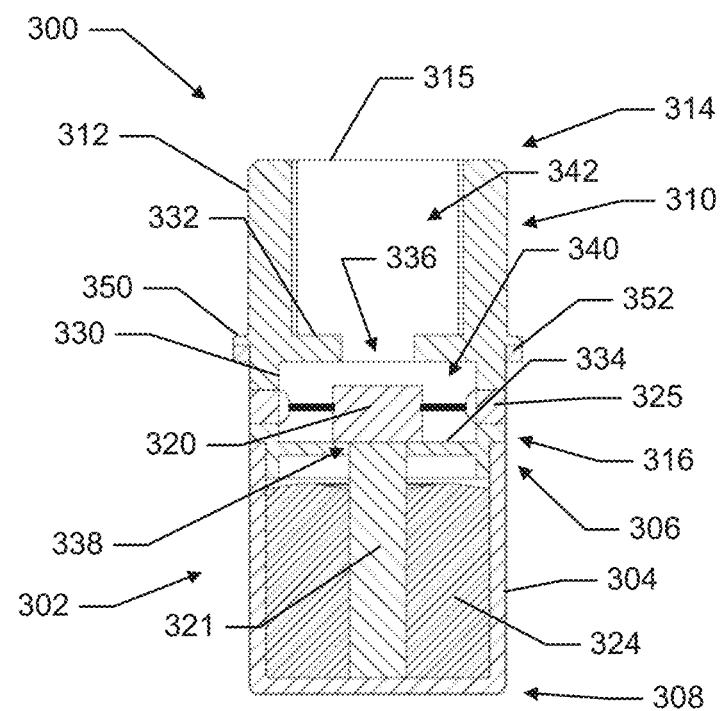
Figure 4:
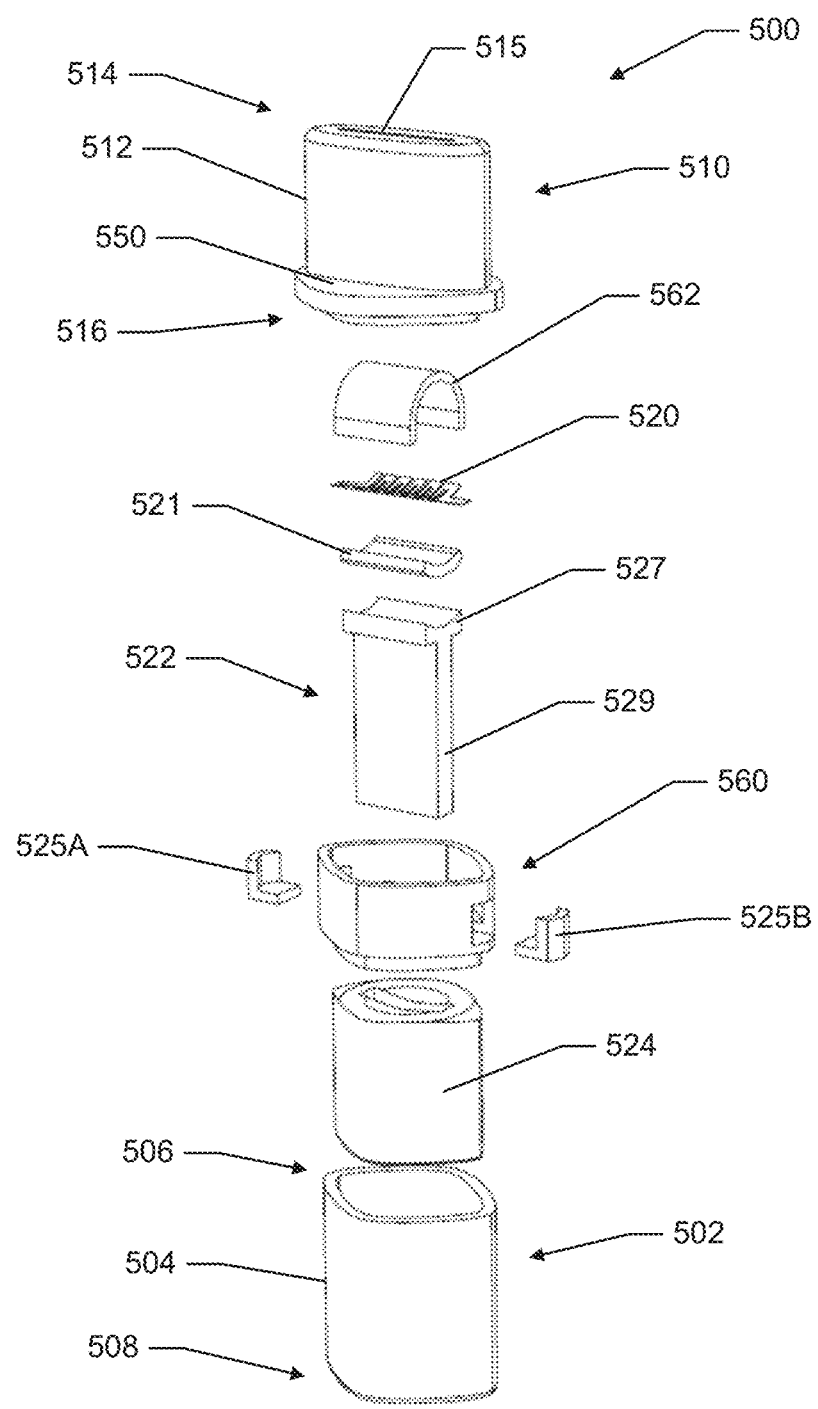
Figure 5A:
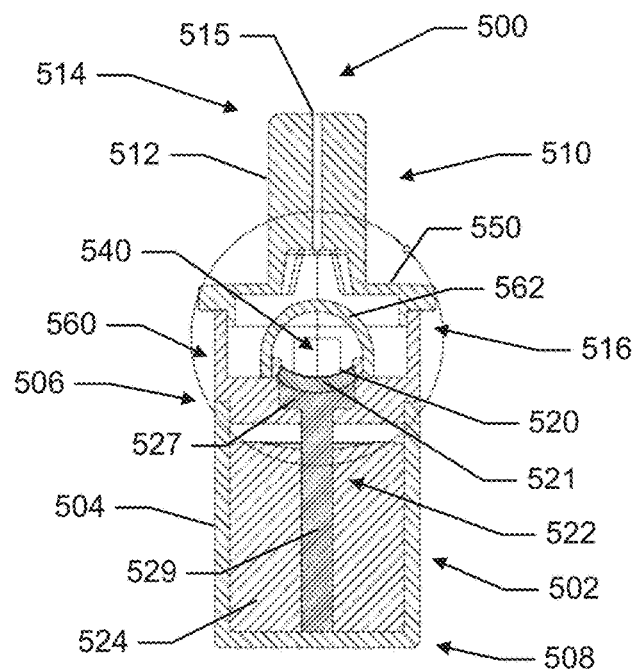
Figure 5B:
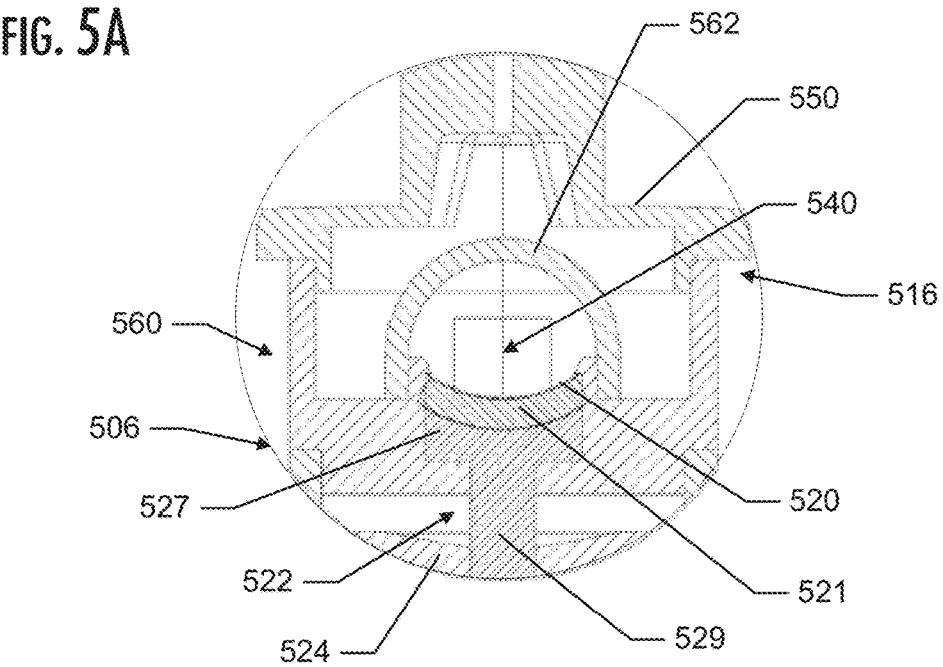
Figure 6:
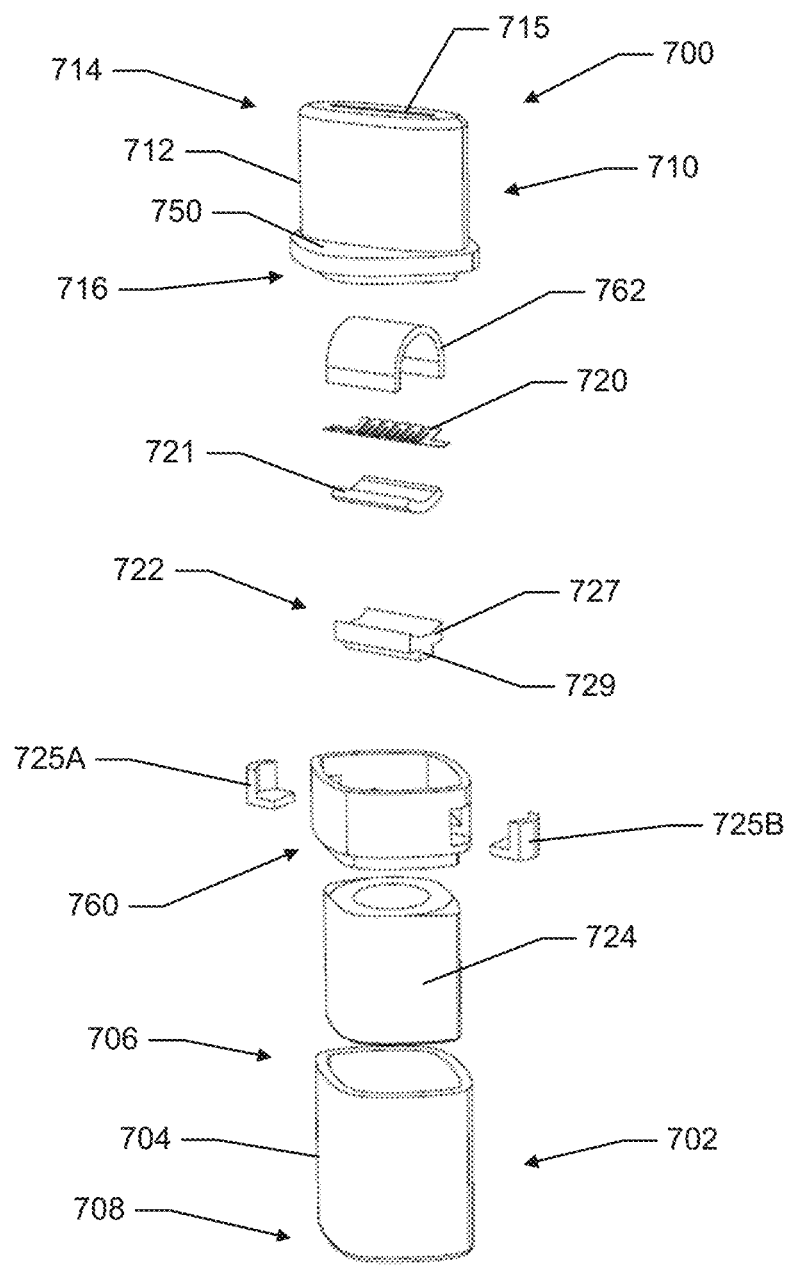
Figure 7A:
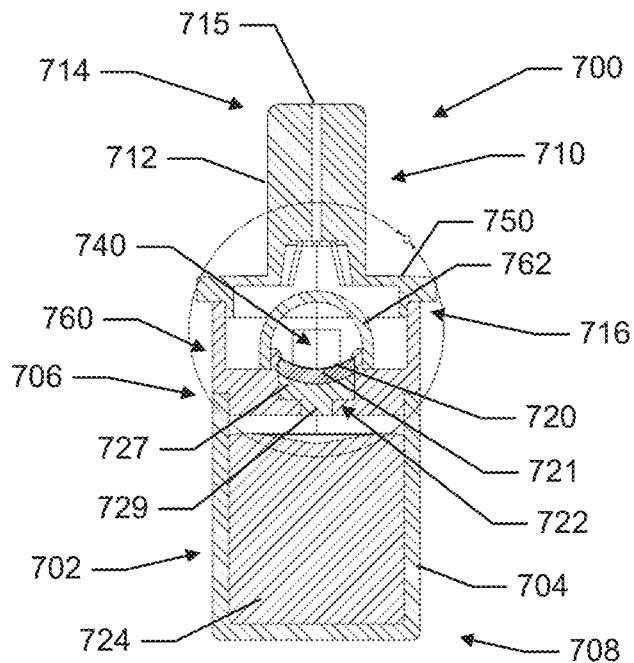
Figure 7B:
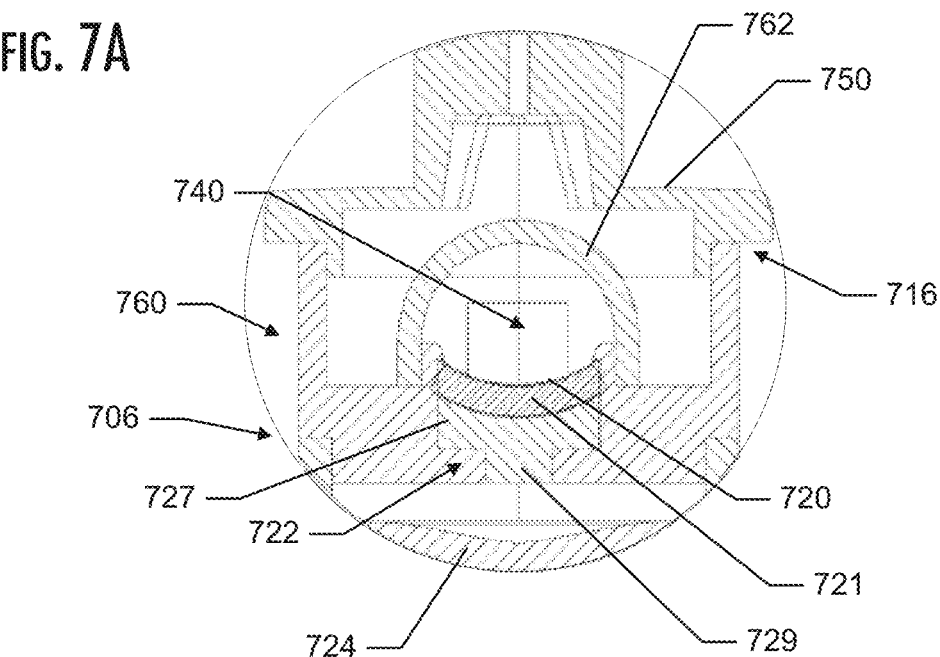
Figure 8:
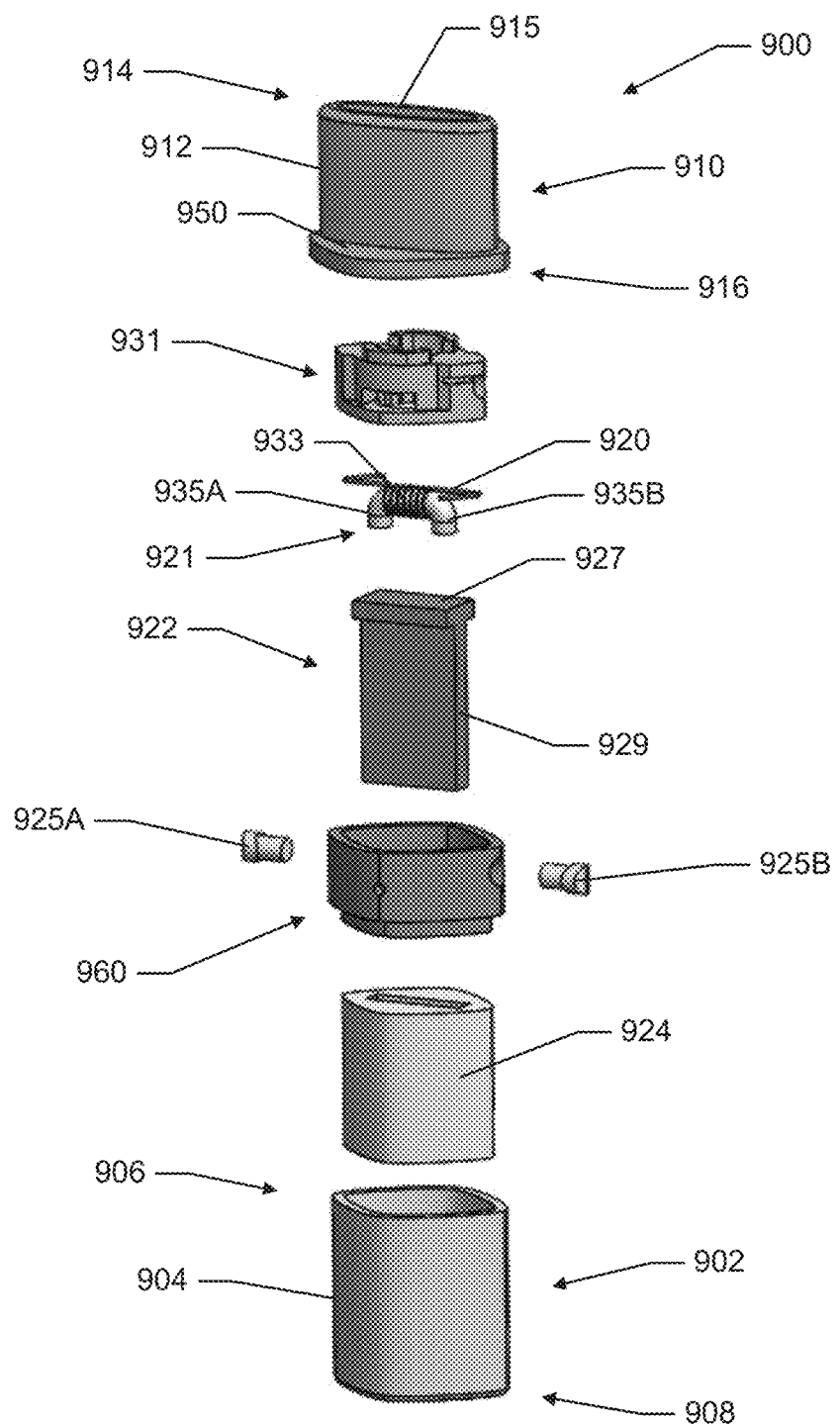
Figure 9:
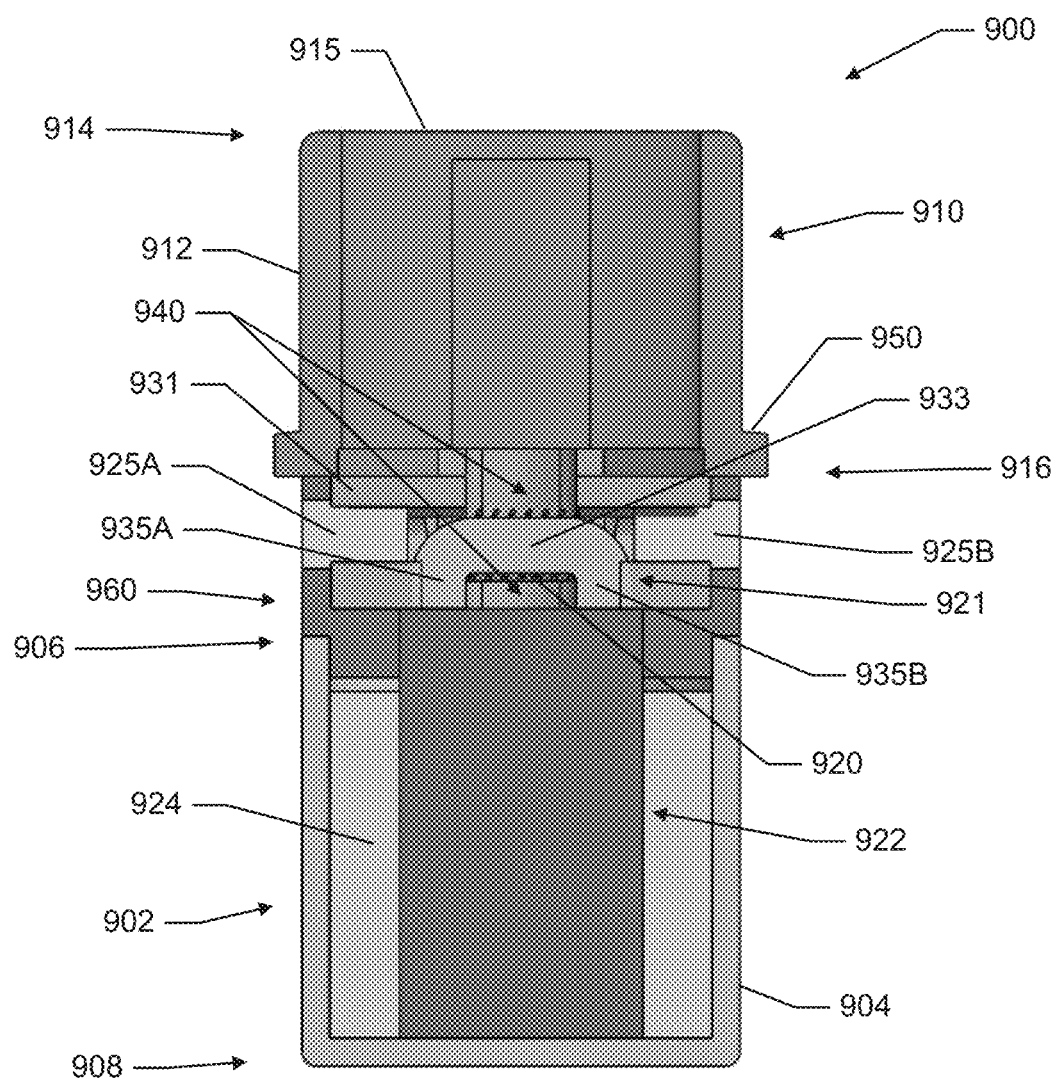
Figure 10:
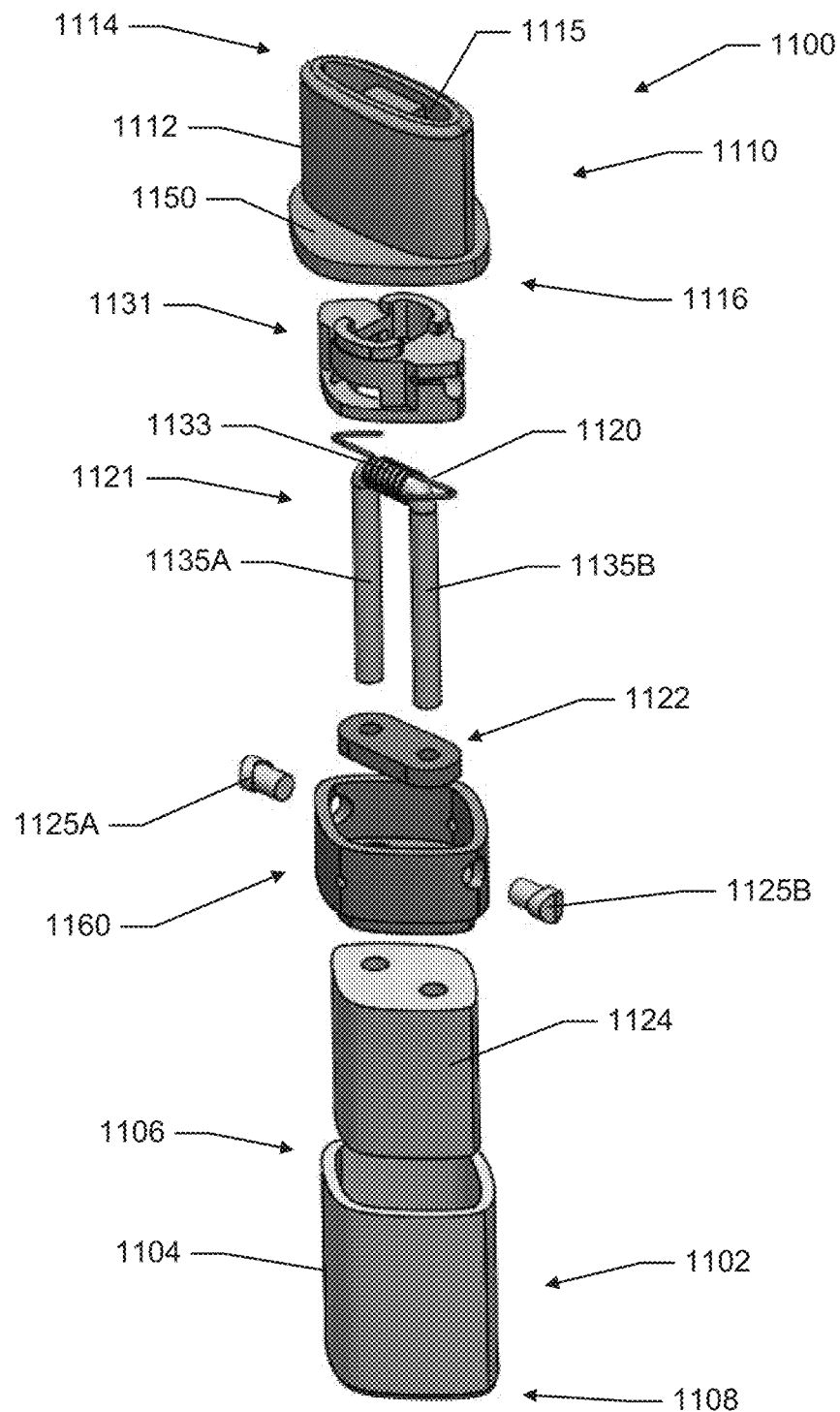
Figure 11:
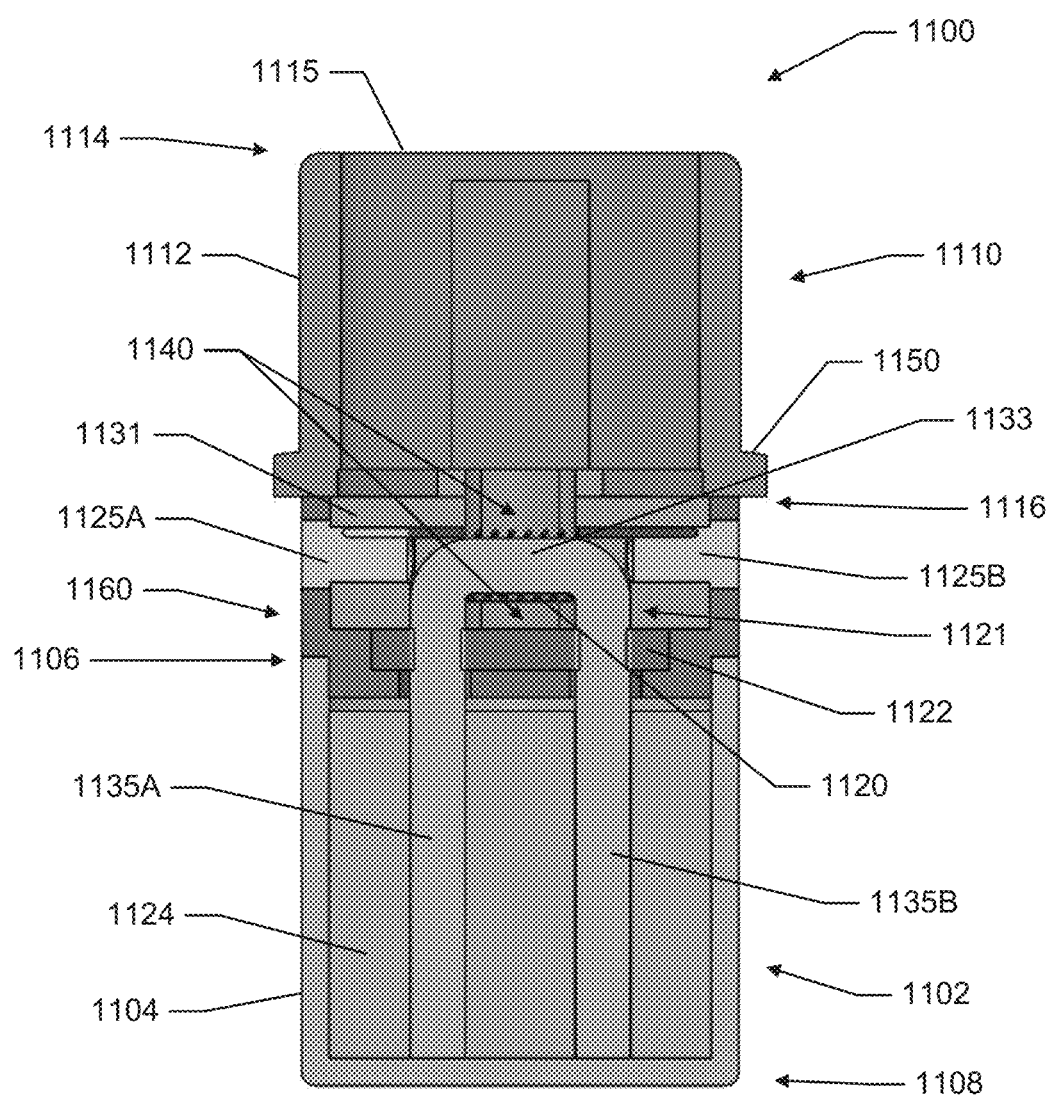
Figure 12:
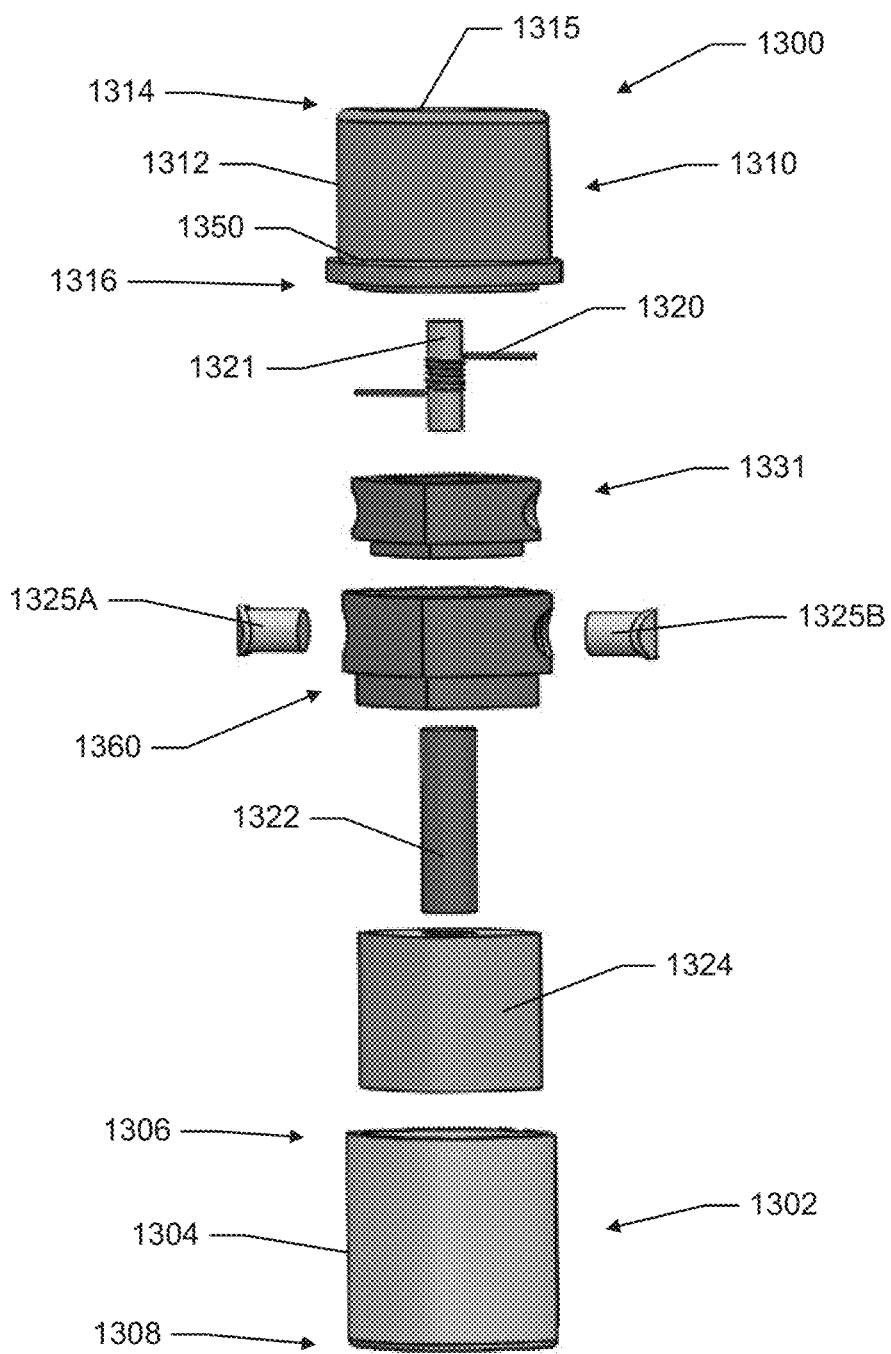
Figure 13:
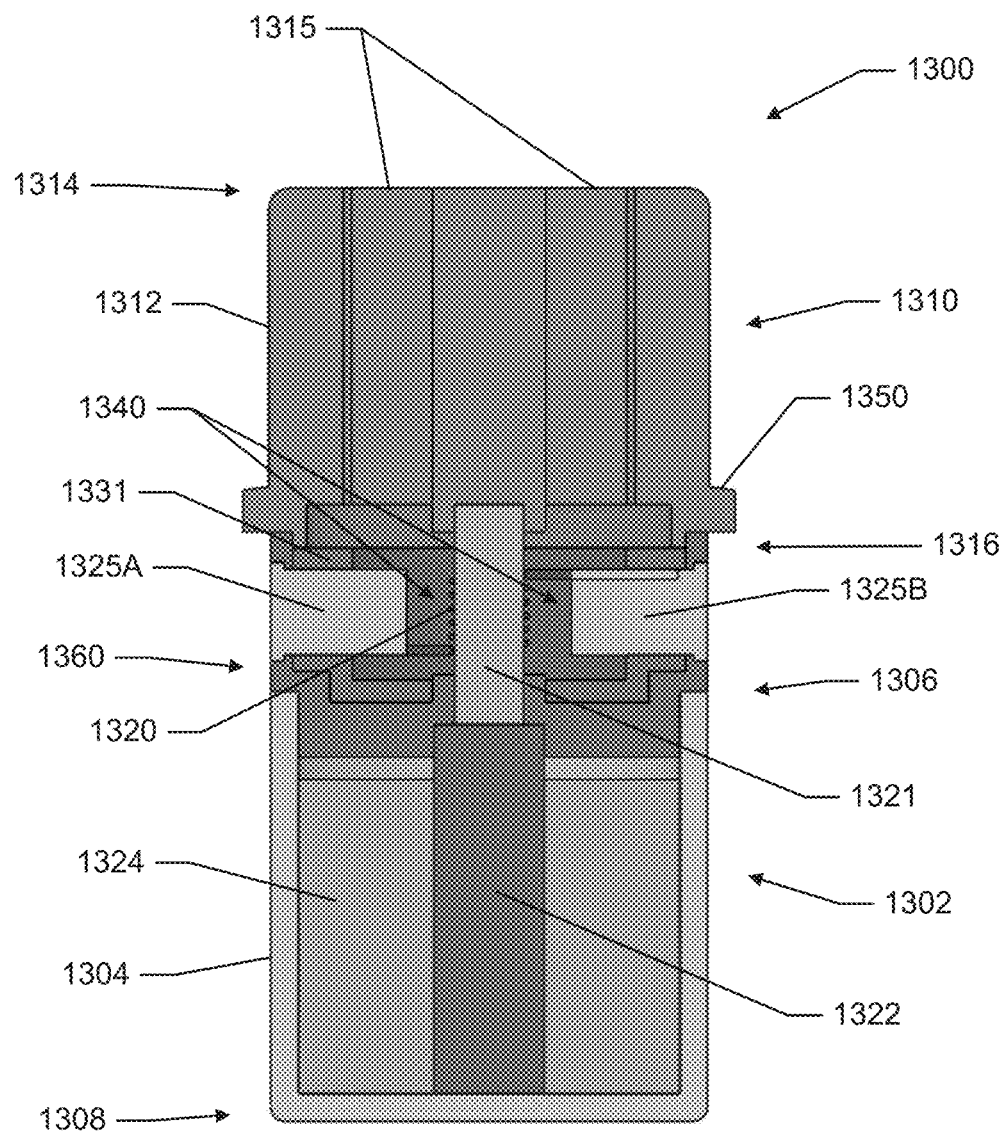
Figure 14:
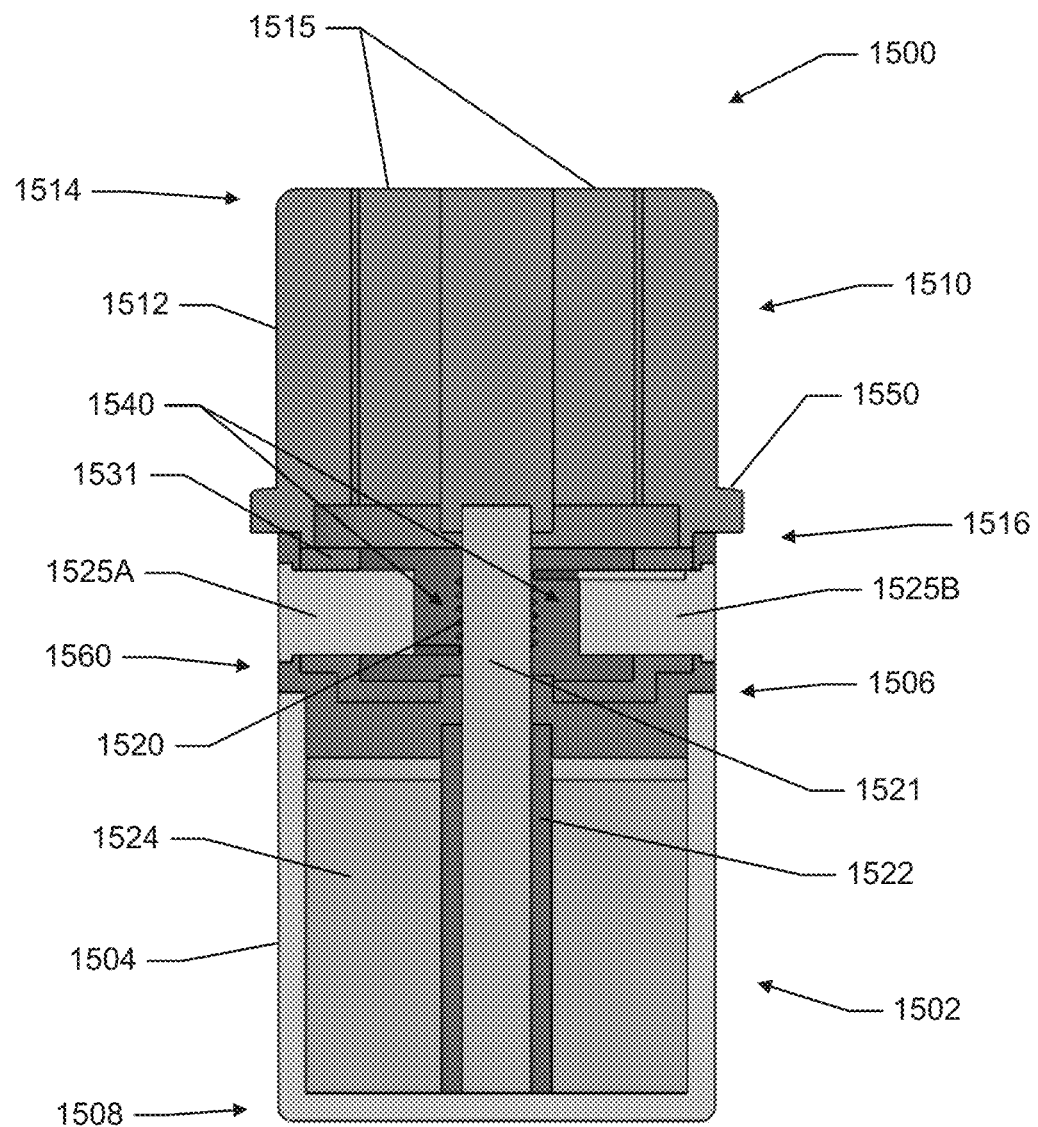
Figure 15:
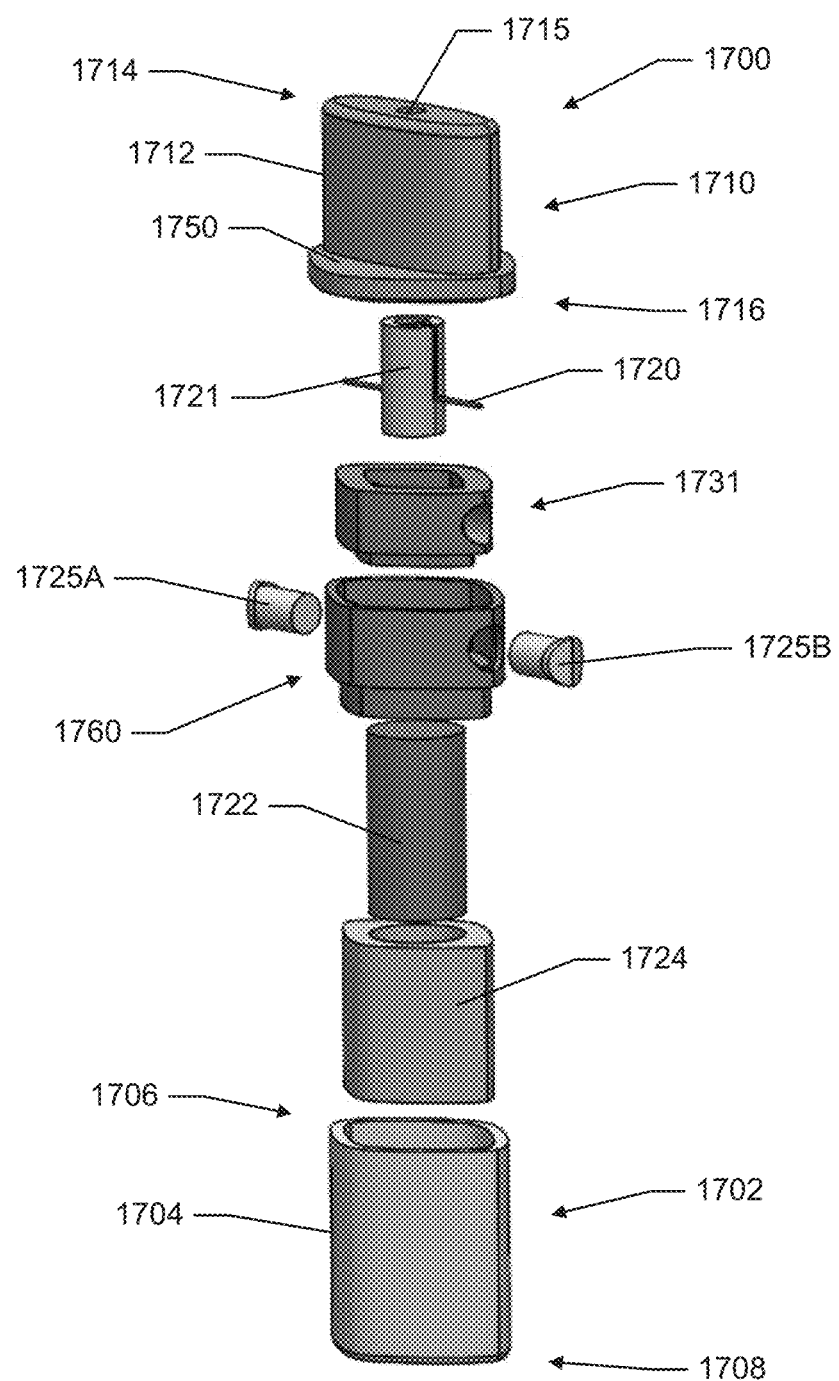
Figure 16:
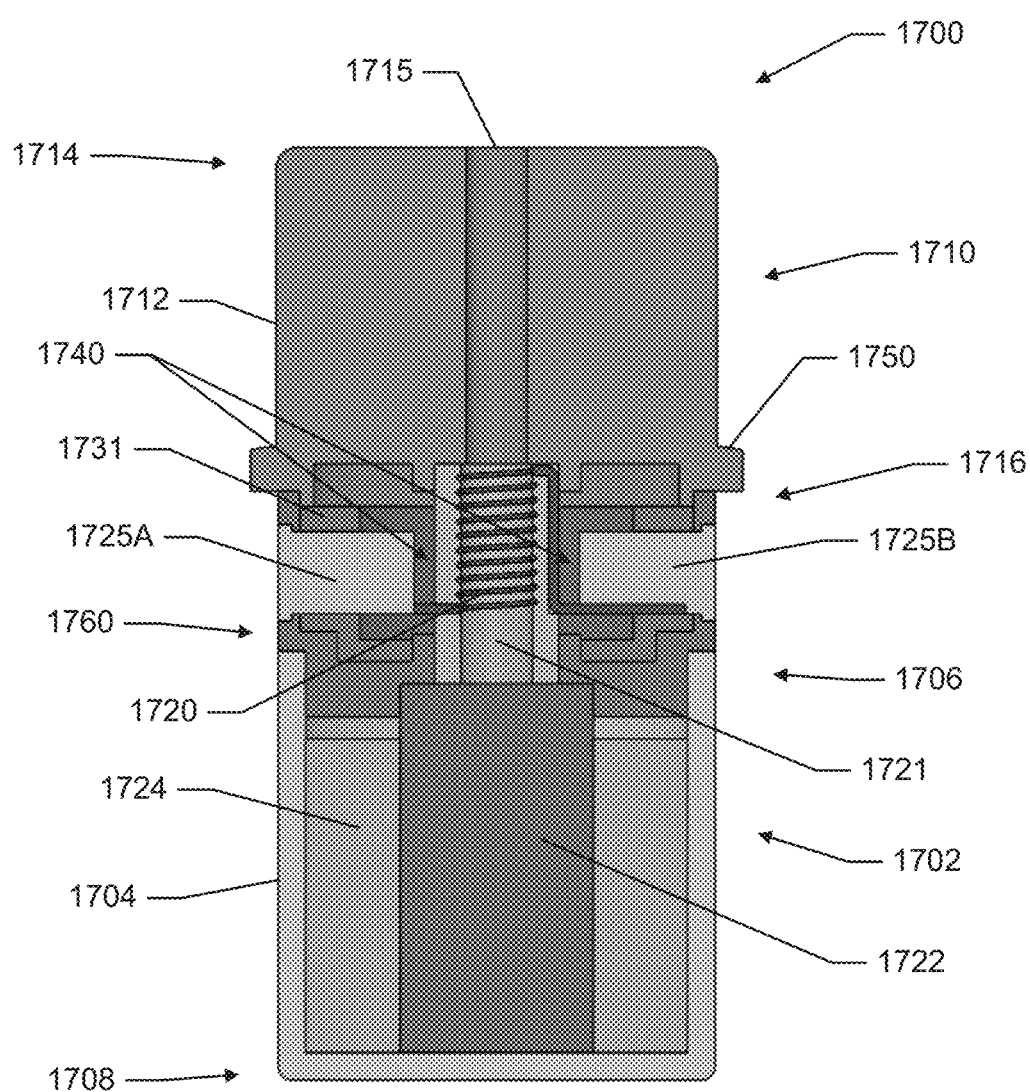
Figure 17:
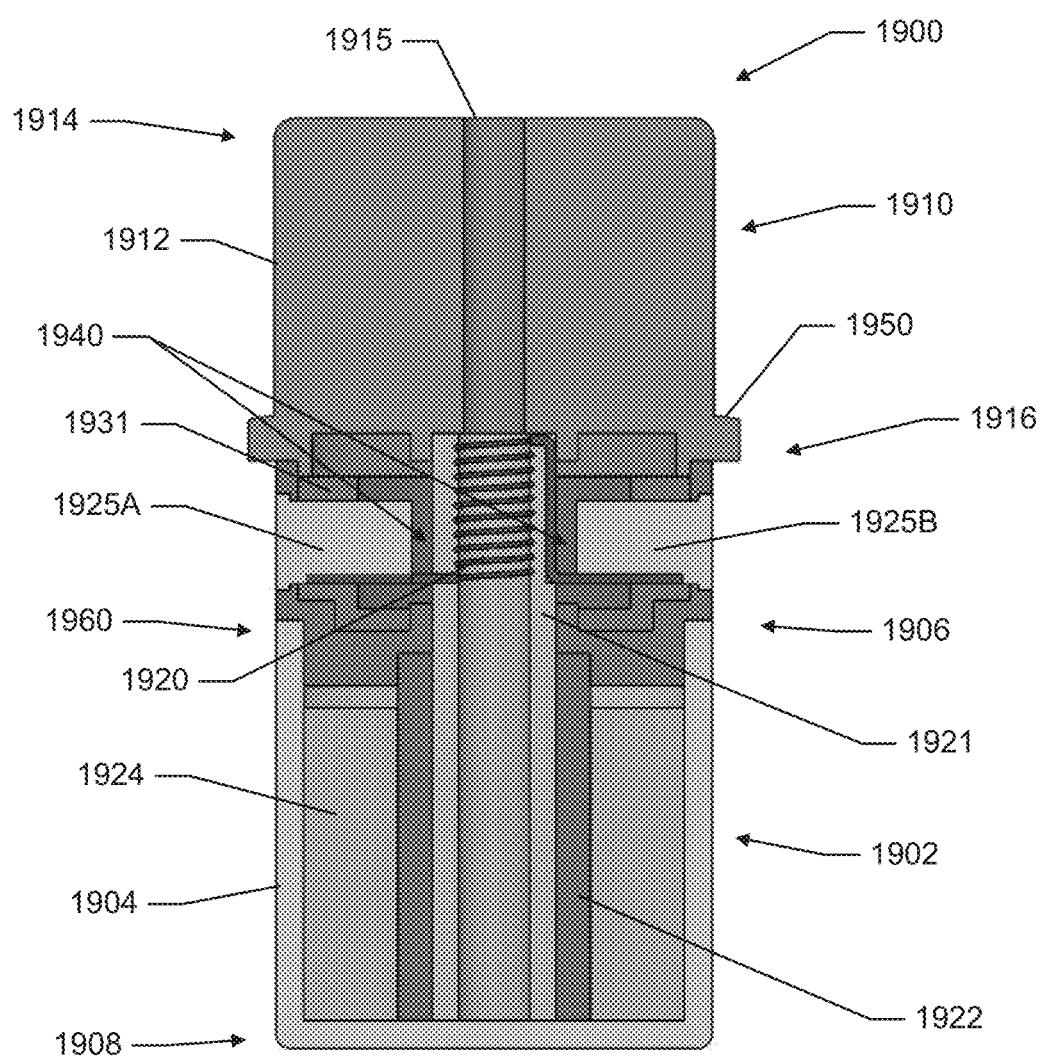
Figure 18:
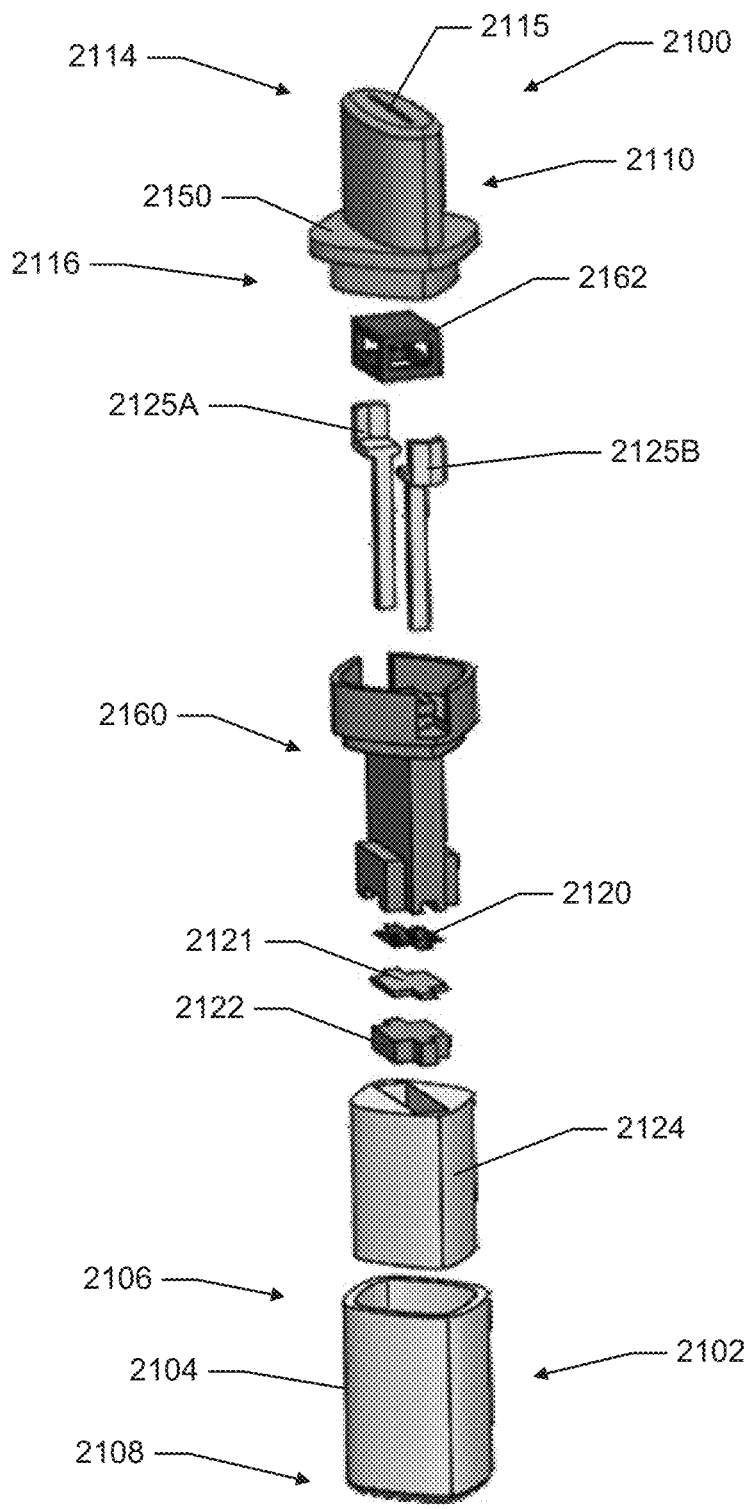
Figure 19:
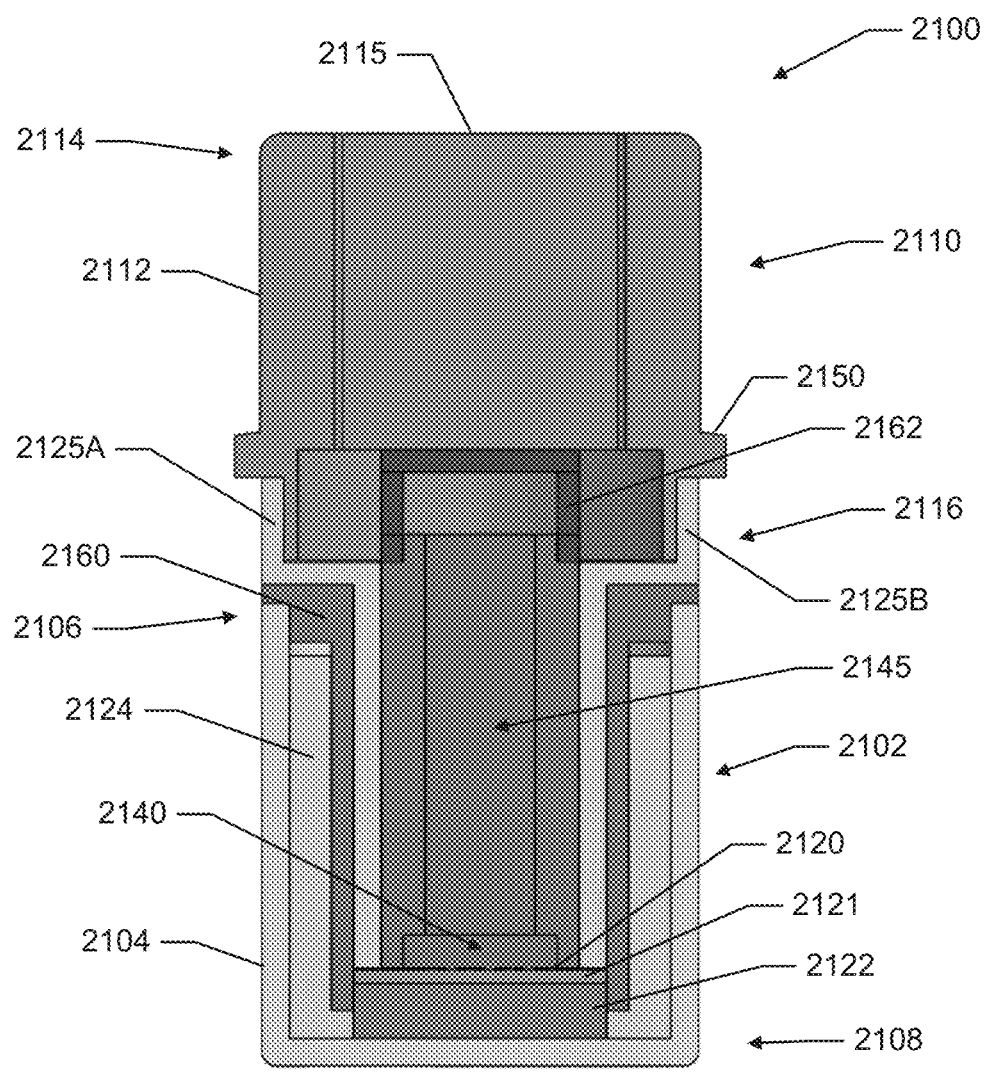
Figure 20:
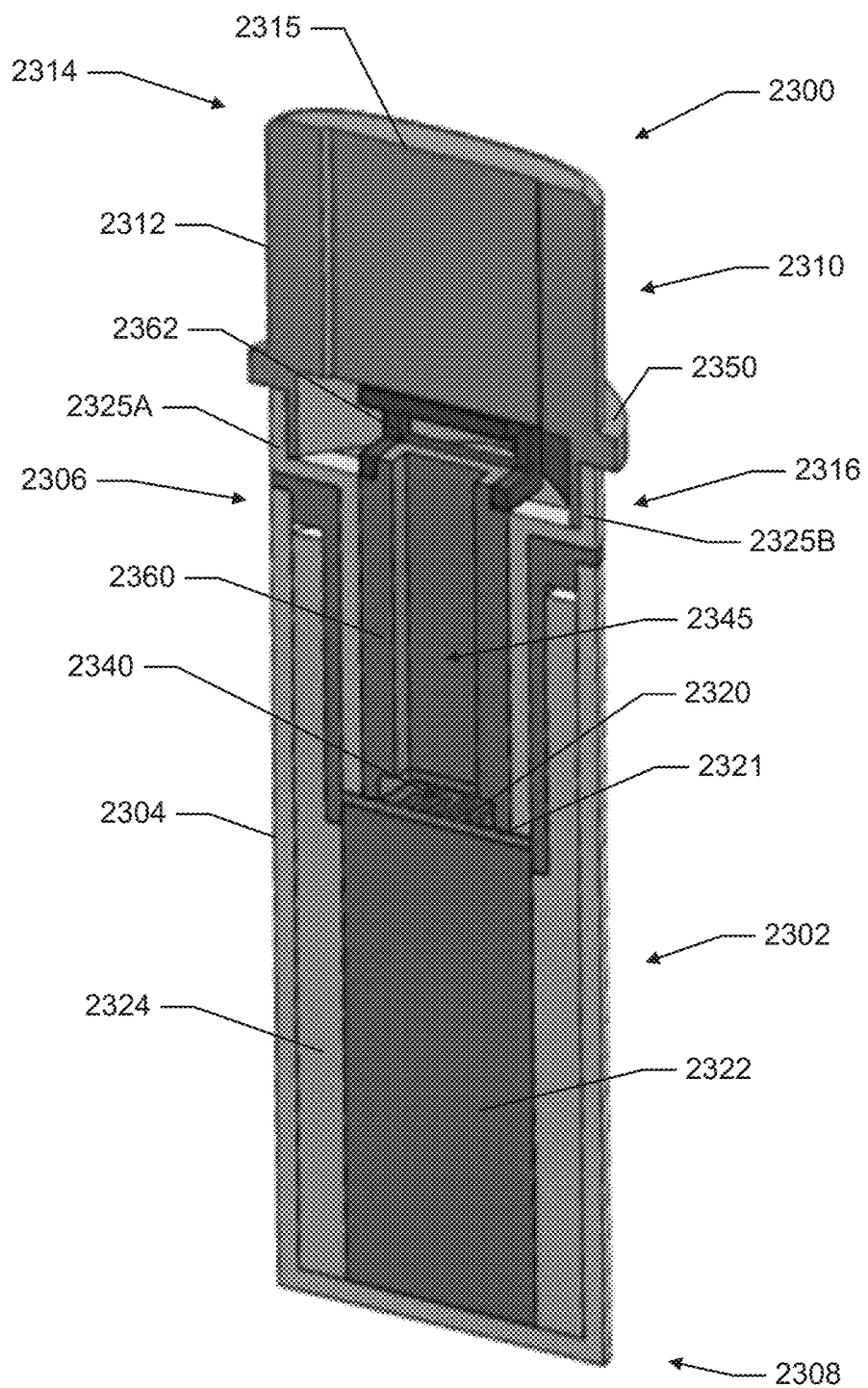
Figure 21:
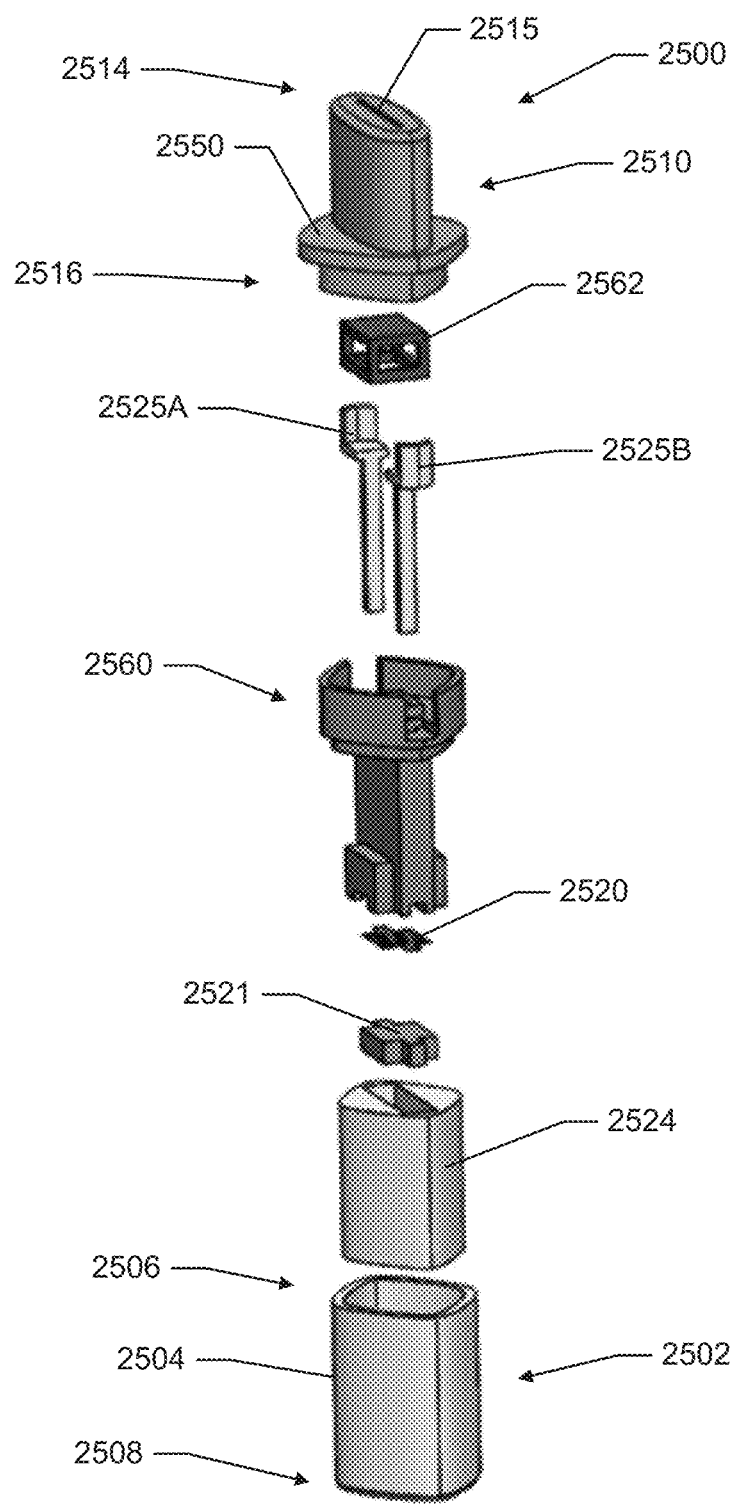
Figure 22:
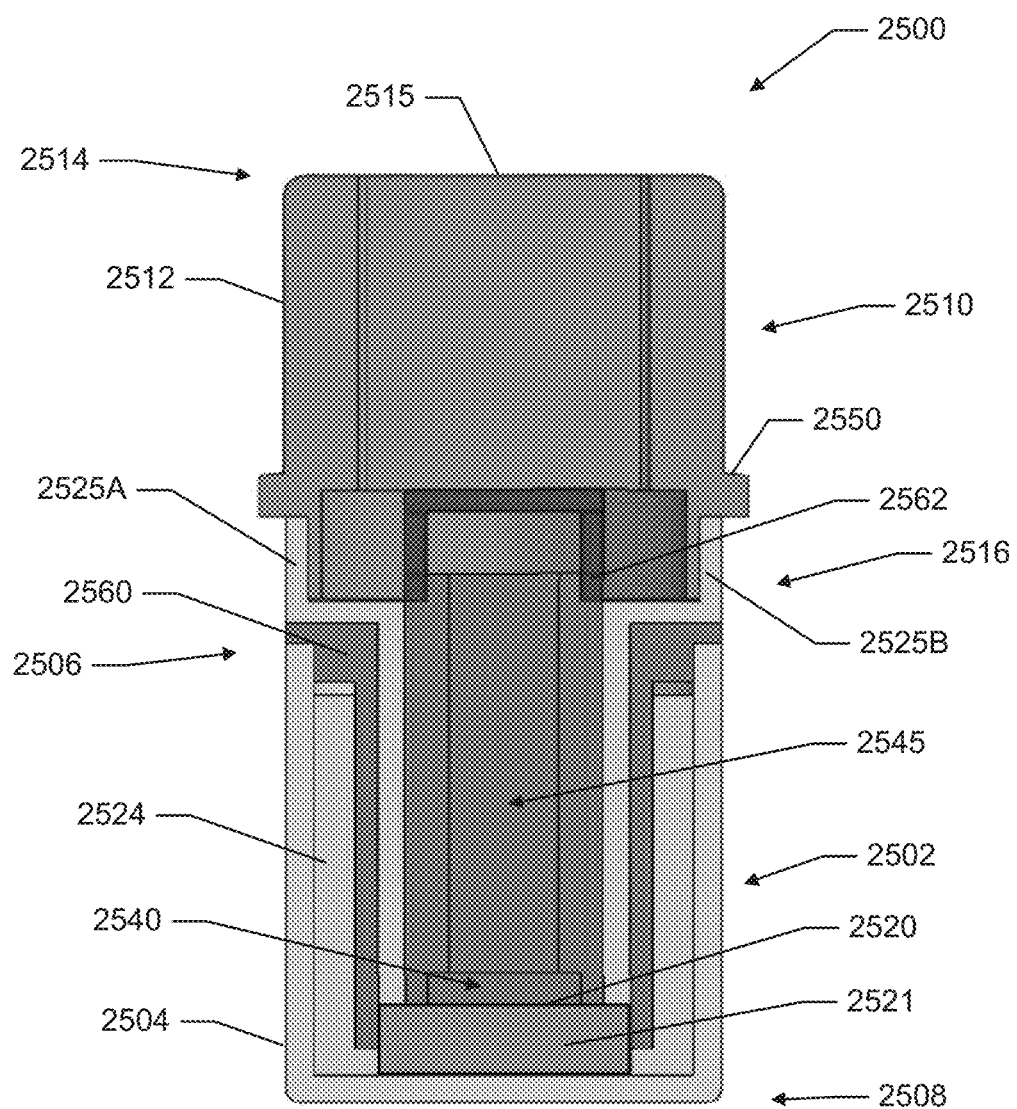
Figure 23:
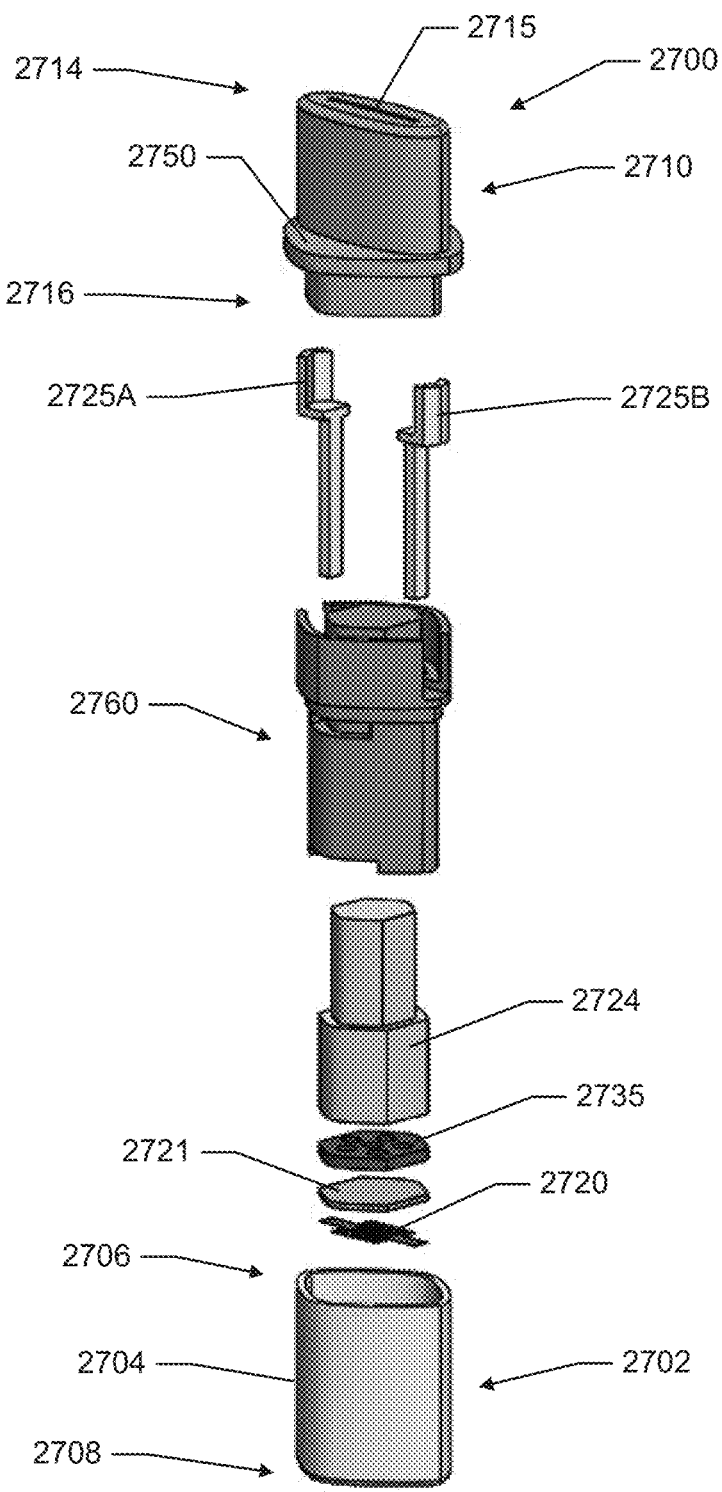
Figure 24:
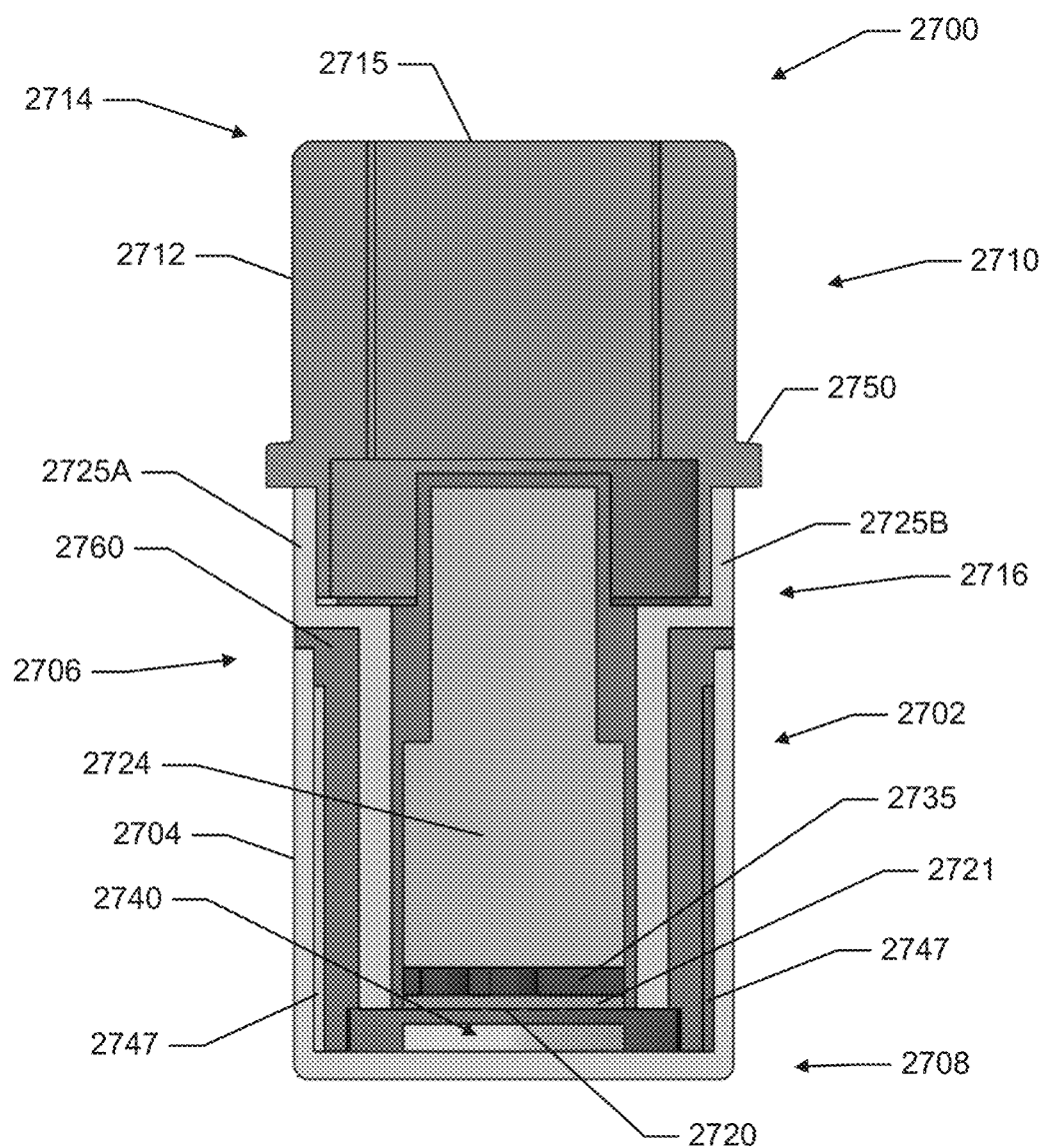
Figure 25:
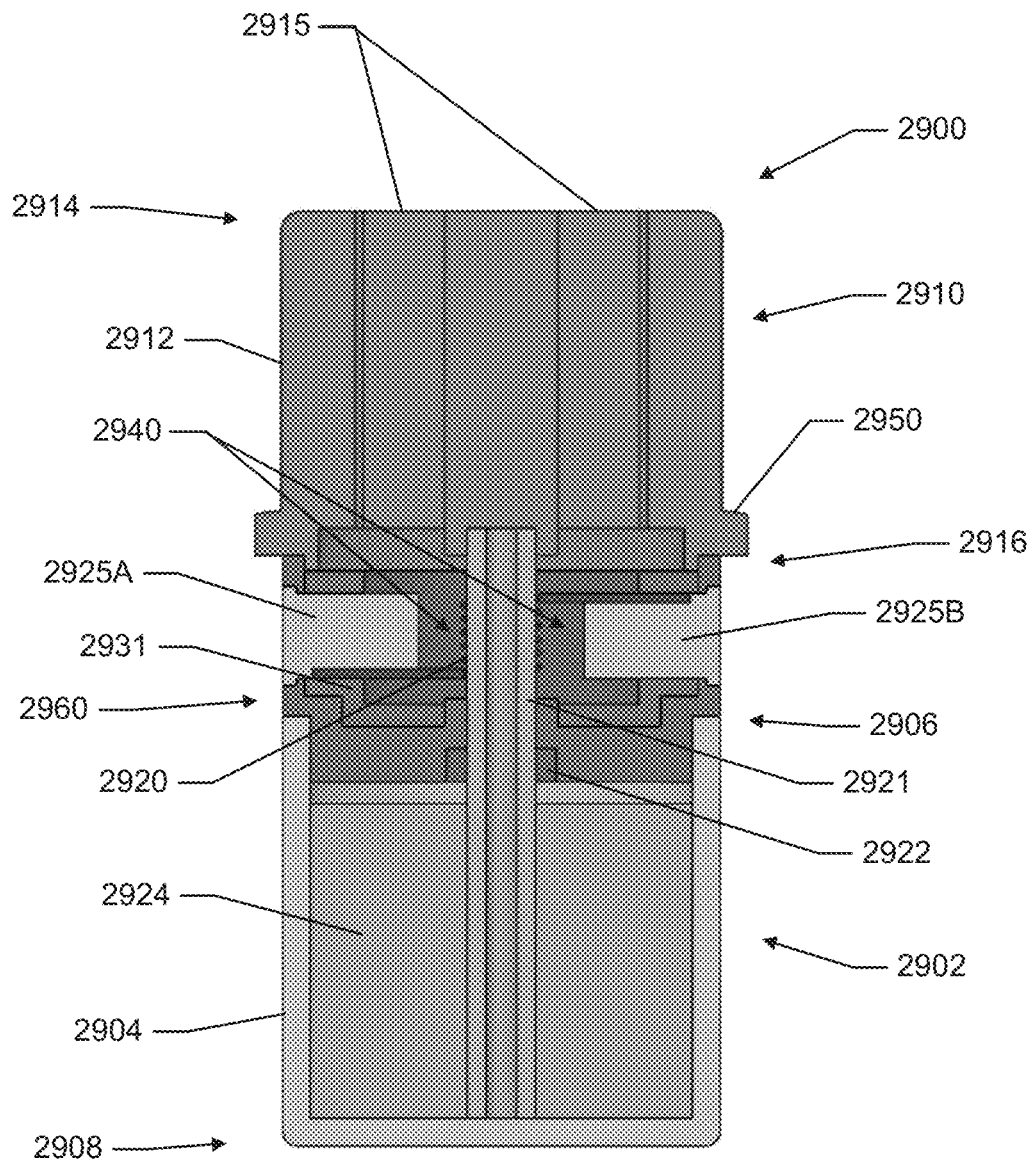
Figure 26:
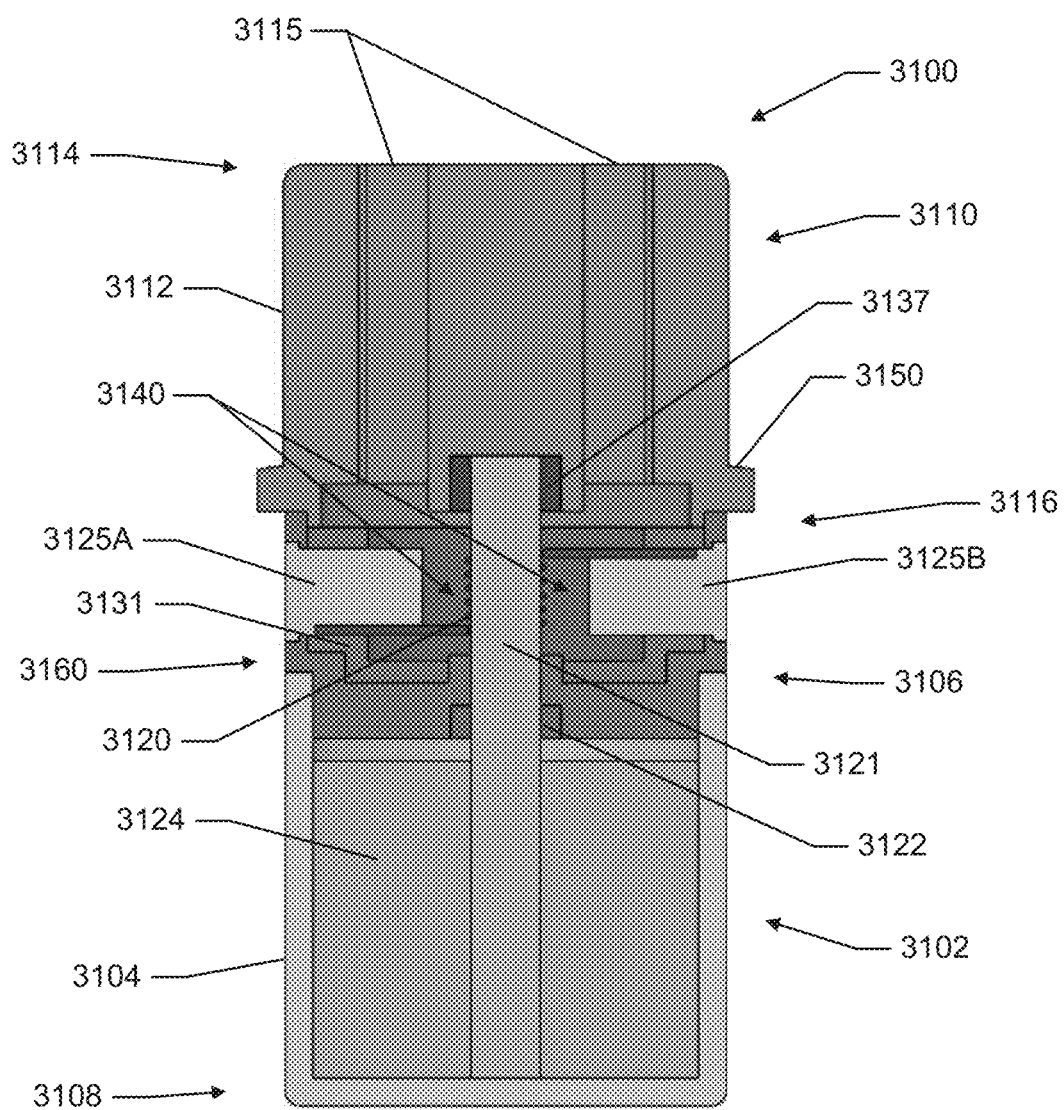
Figure 27:
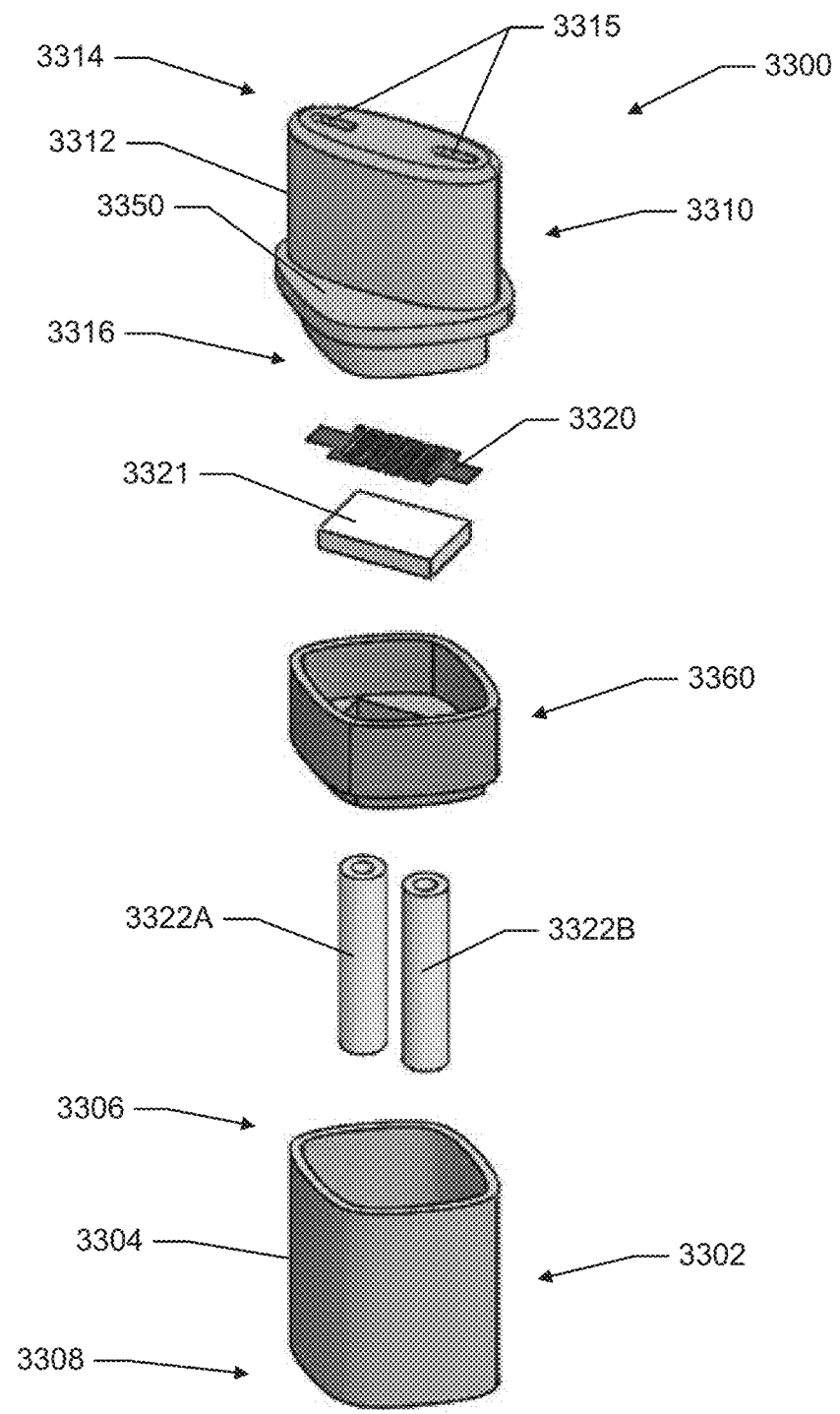
Figure 28:
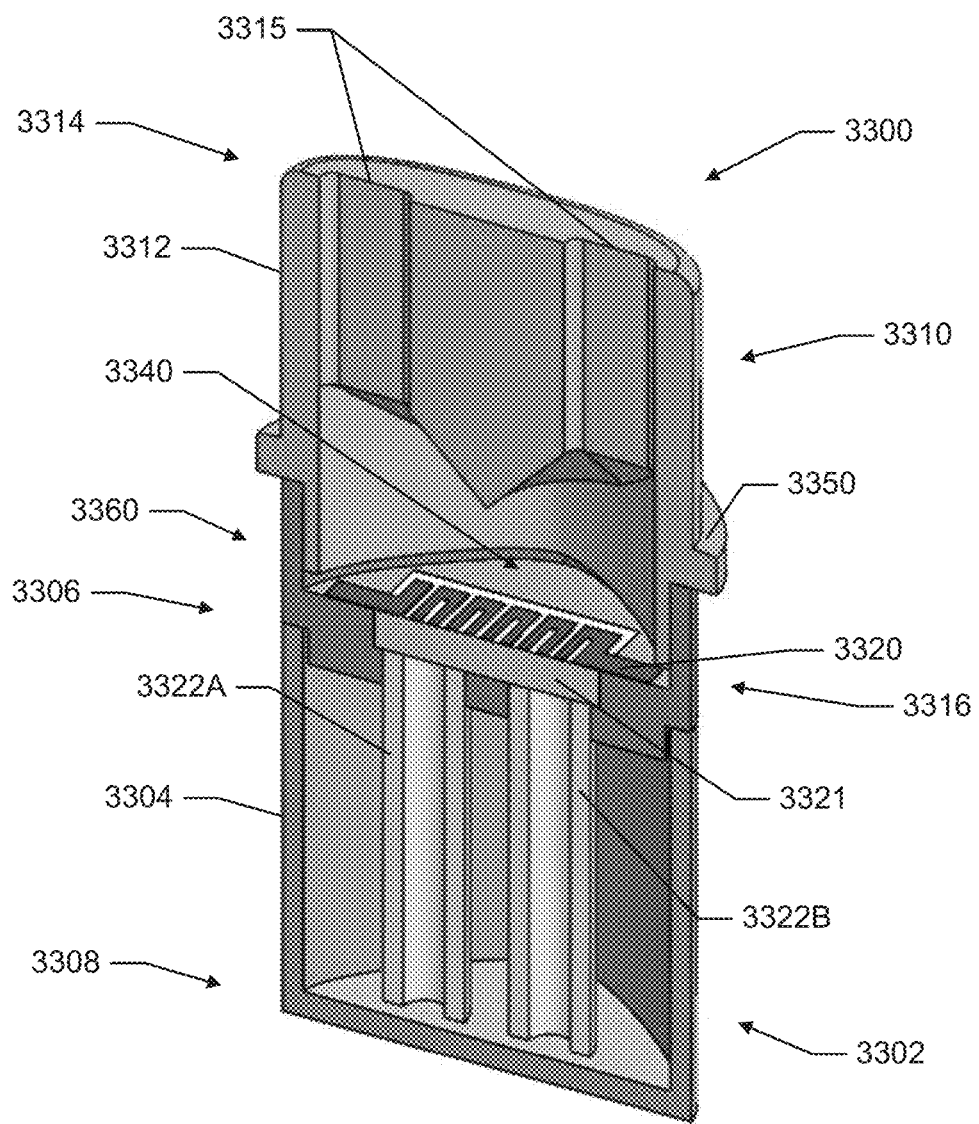
Figure 29:
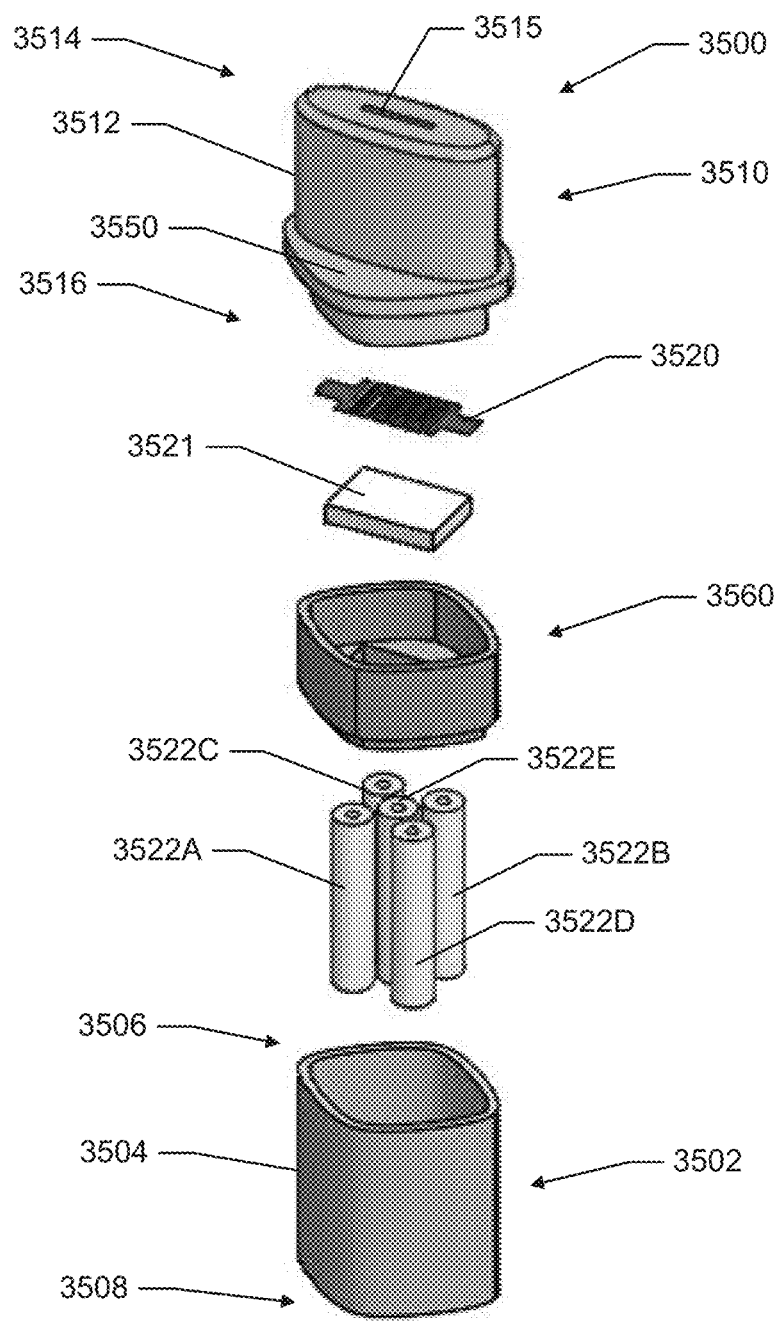
Figure 30:
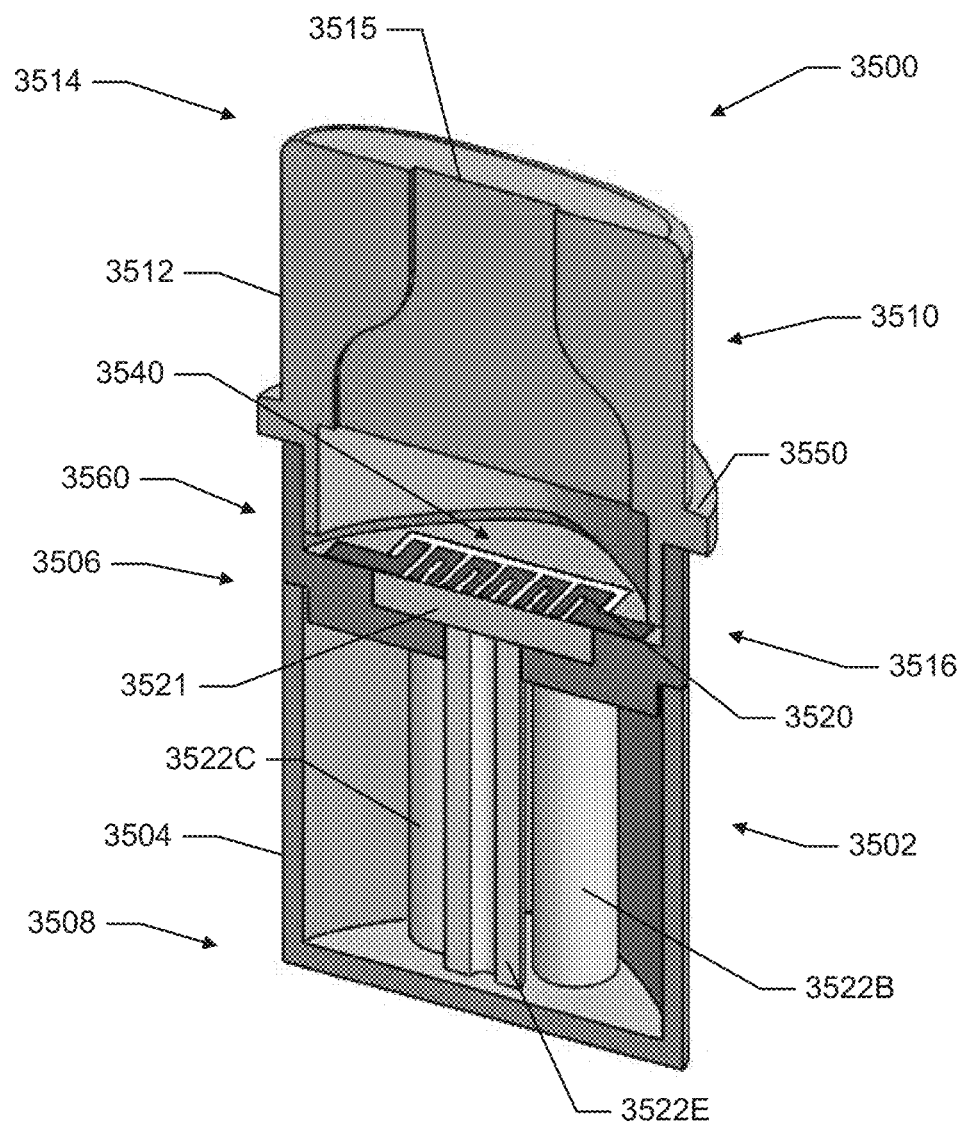
Figure 31:
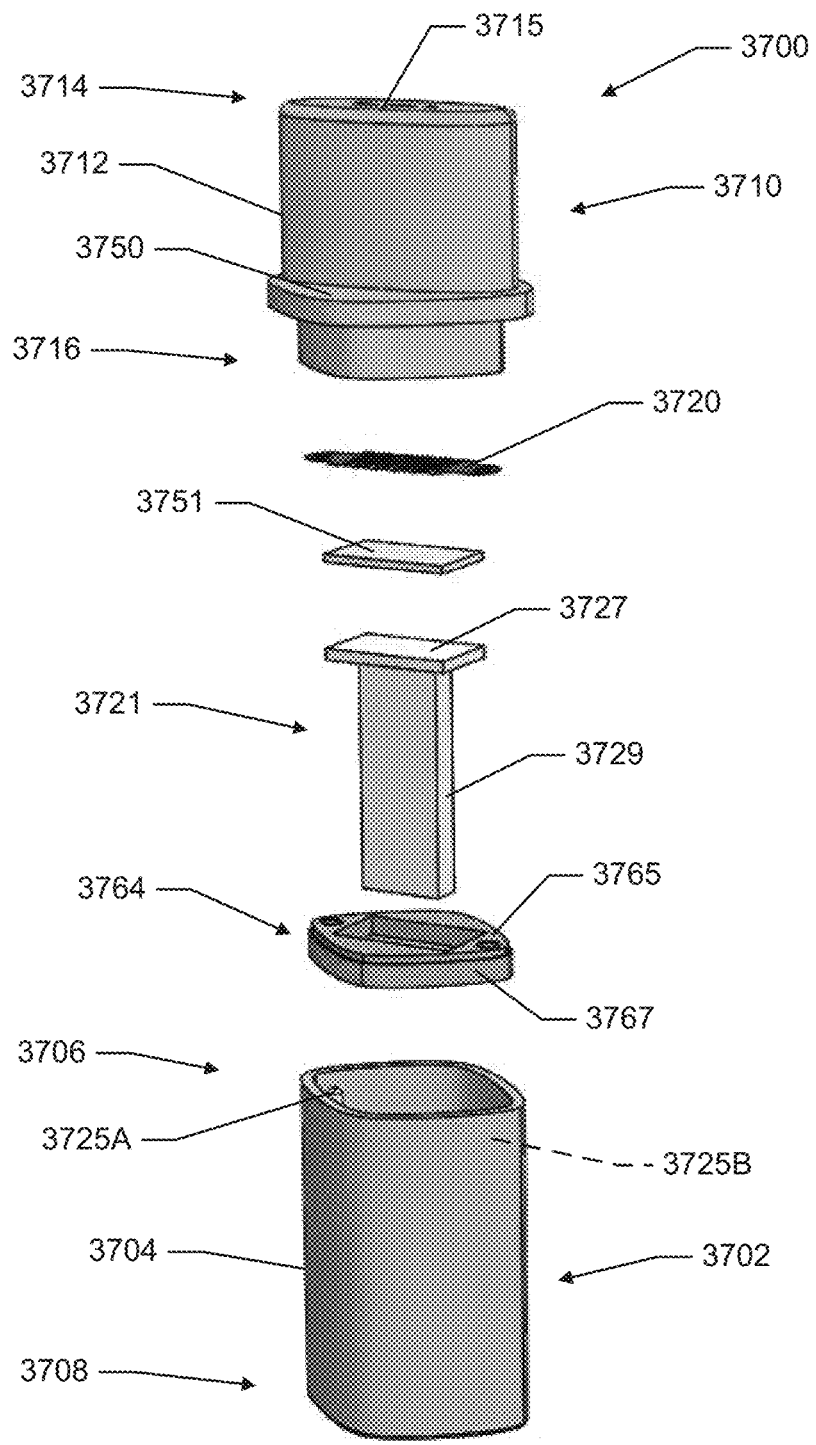
Figure 32:
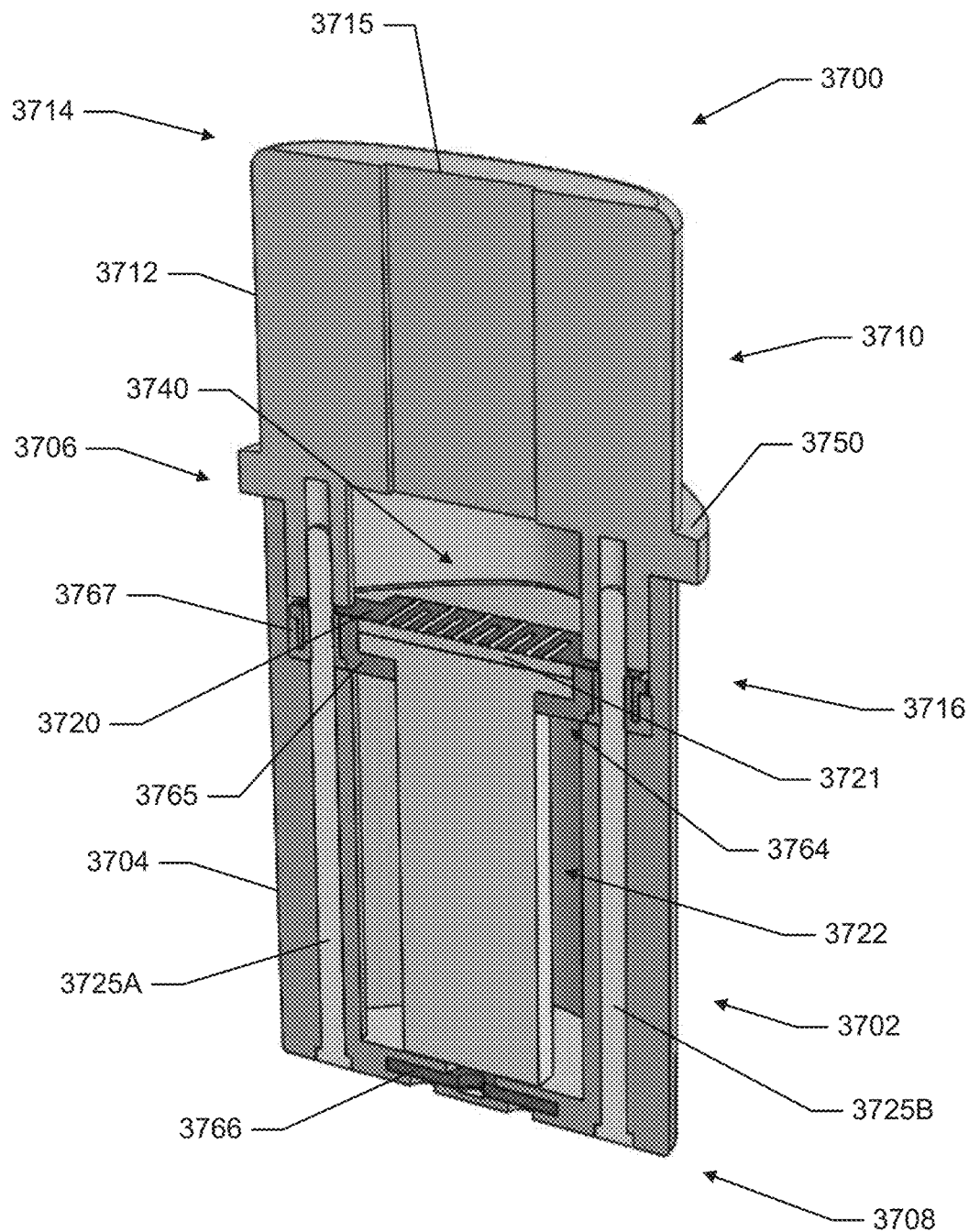
Figure 33:
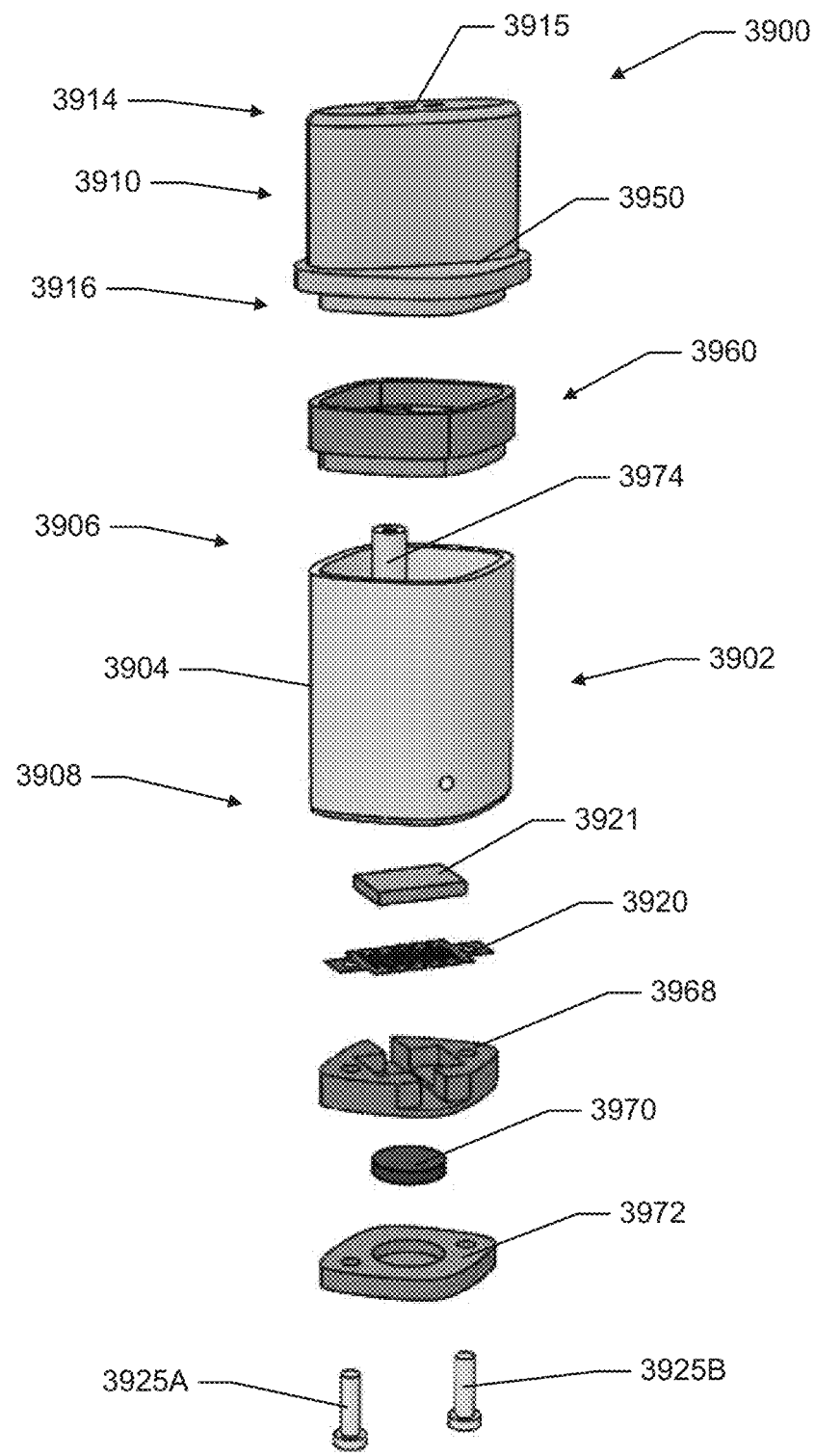
Figure 34:
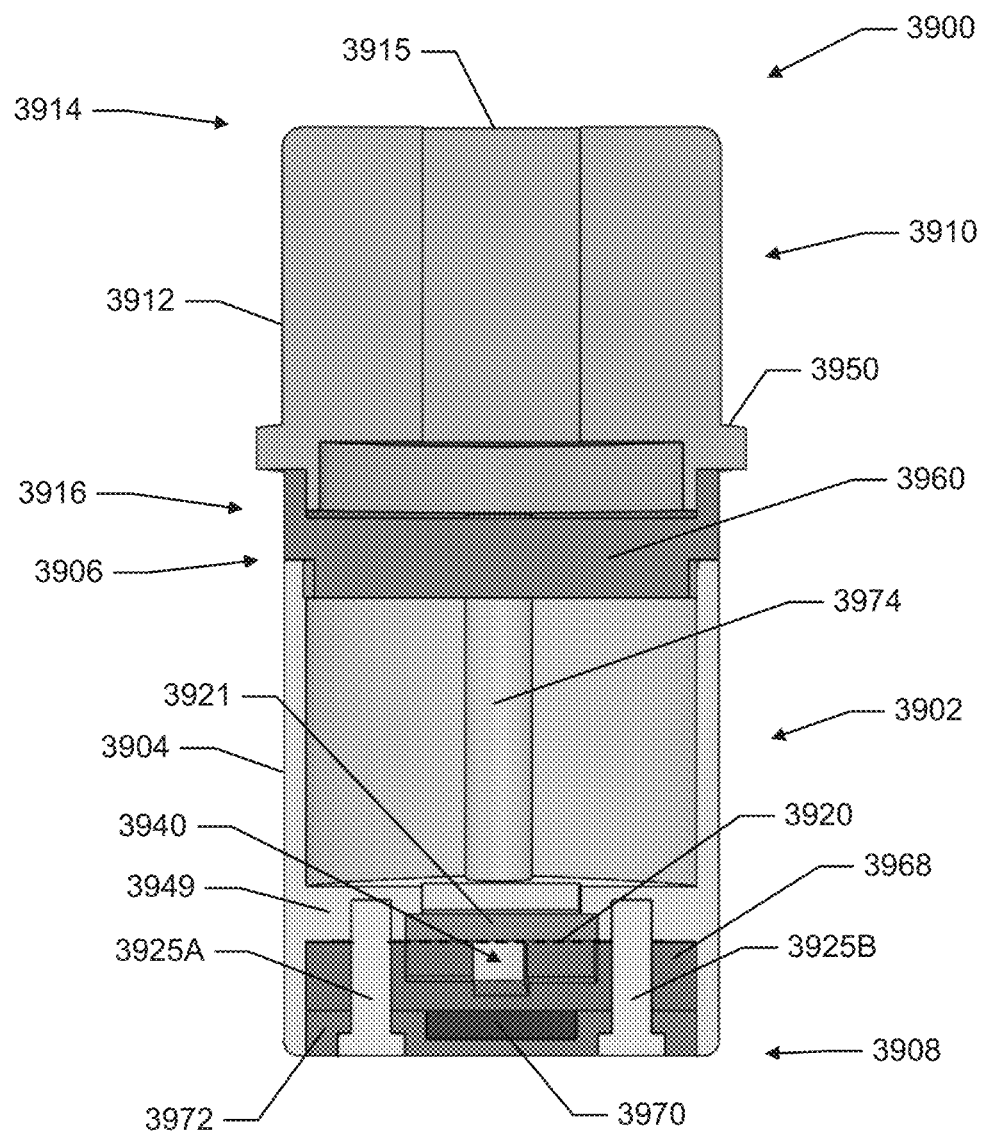
Figure 35:
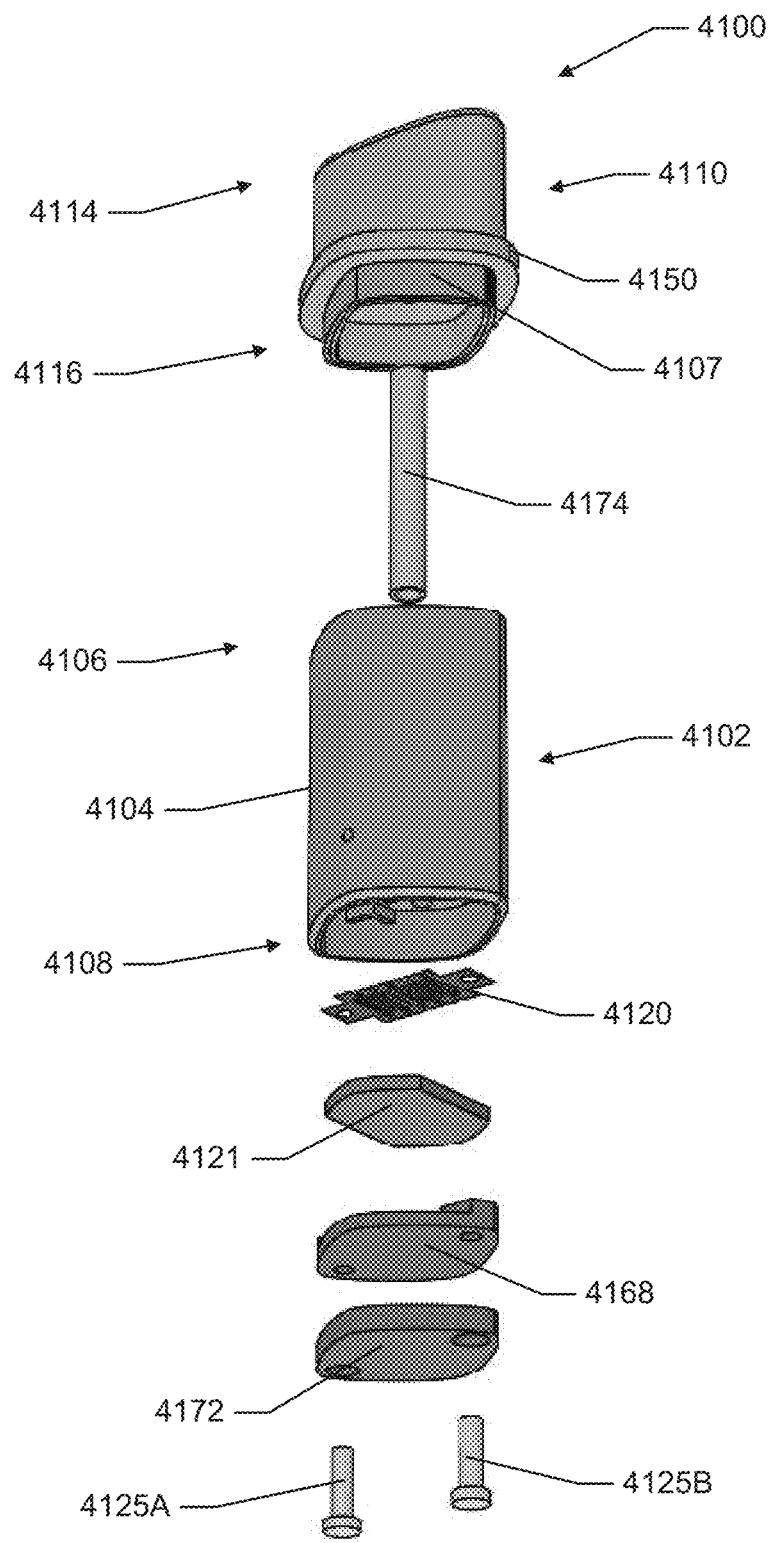
Figure 36:
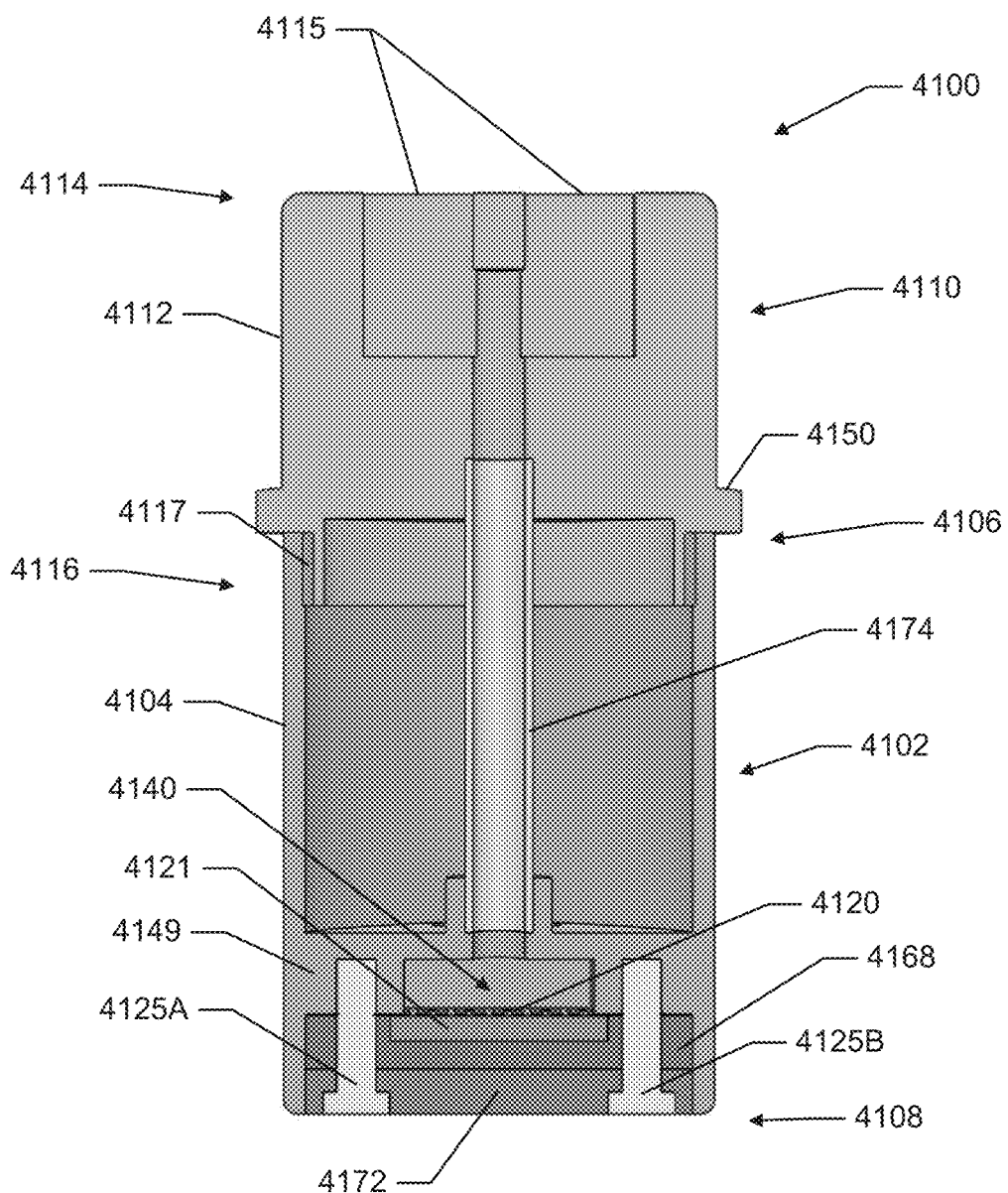
Figure 37:
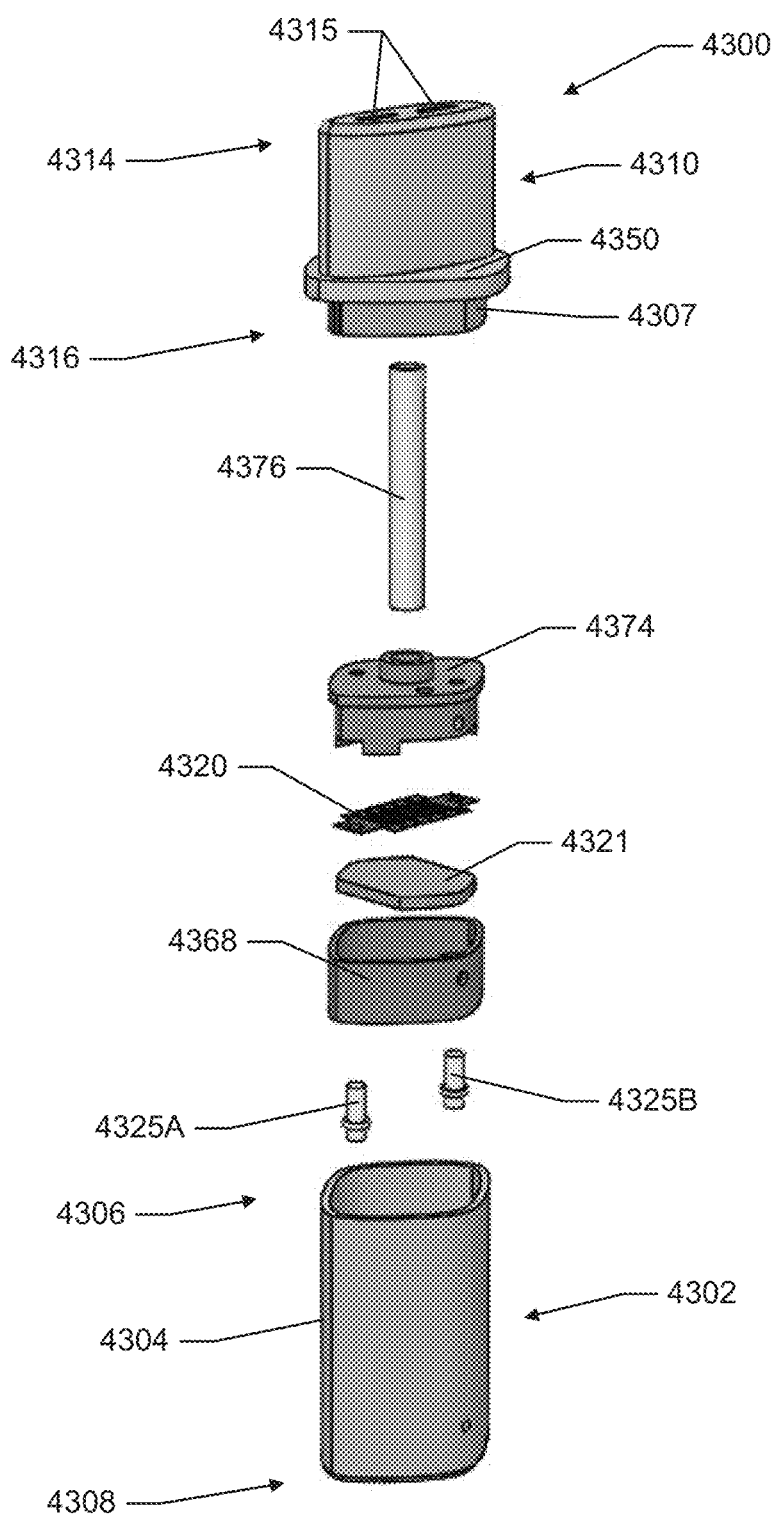
Figure 38:
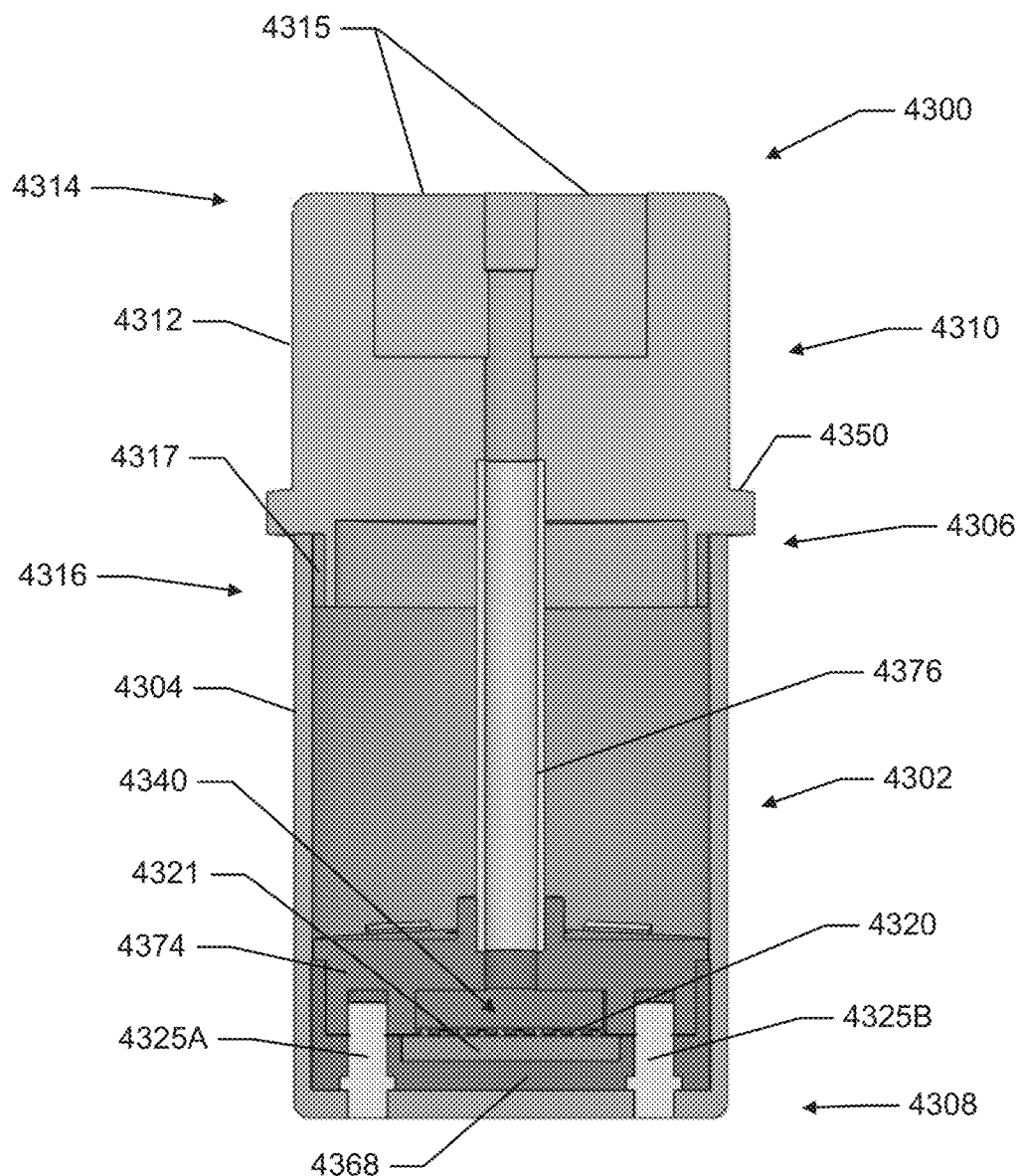
Figure 39:
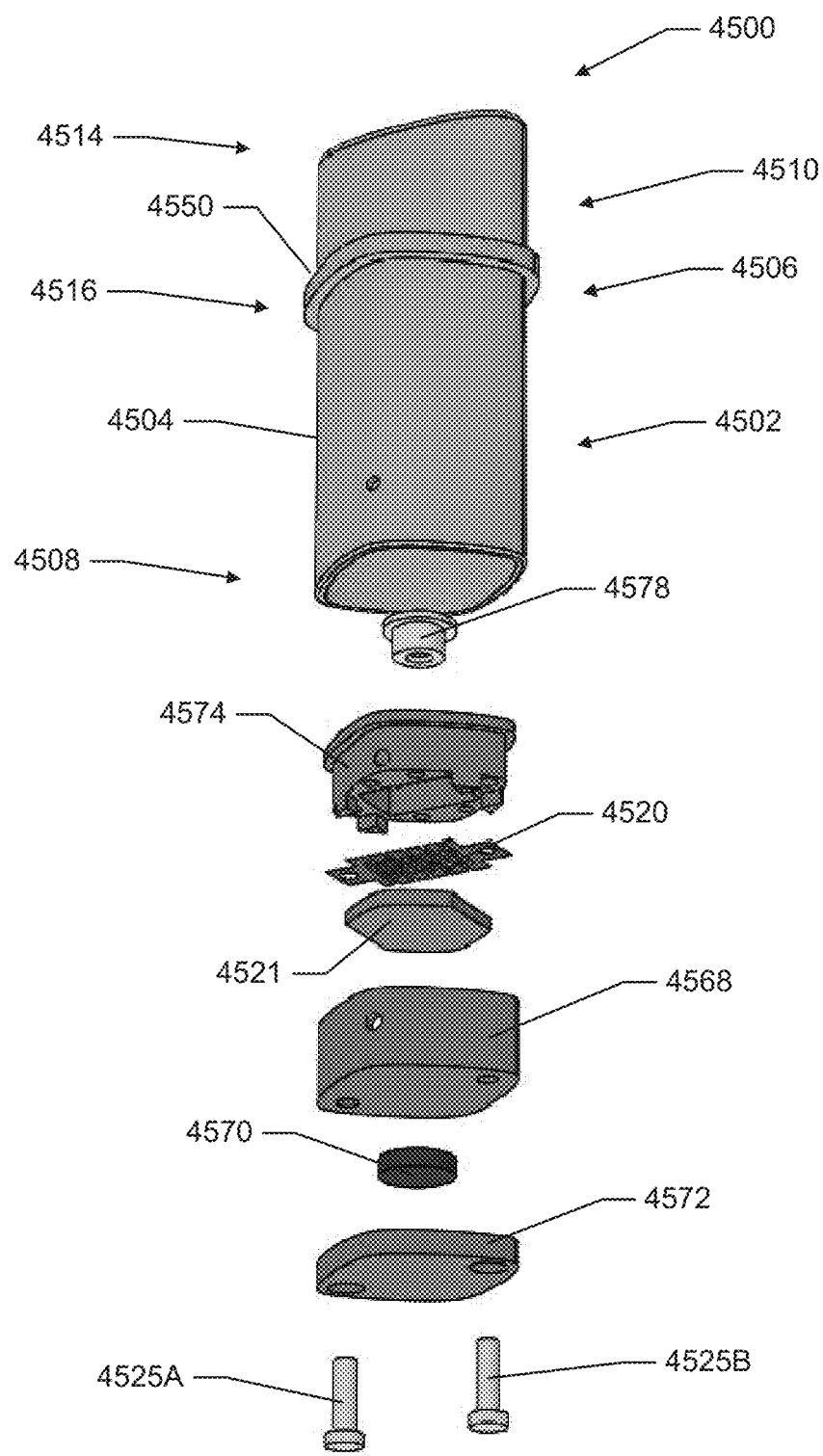
Figure 40:
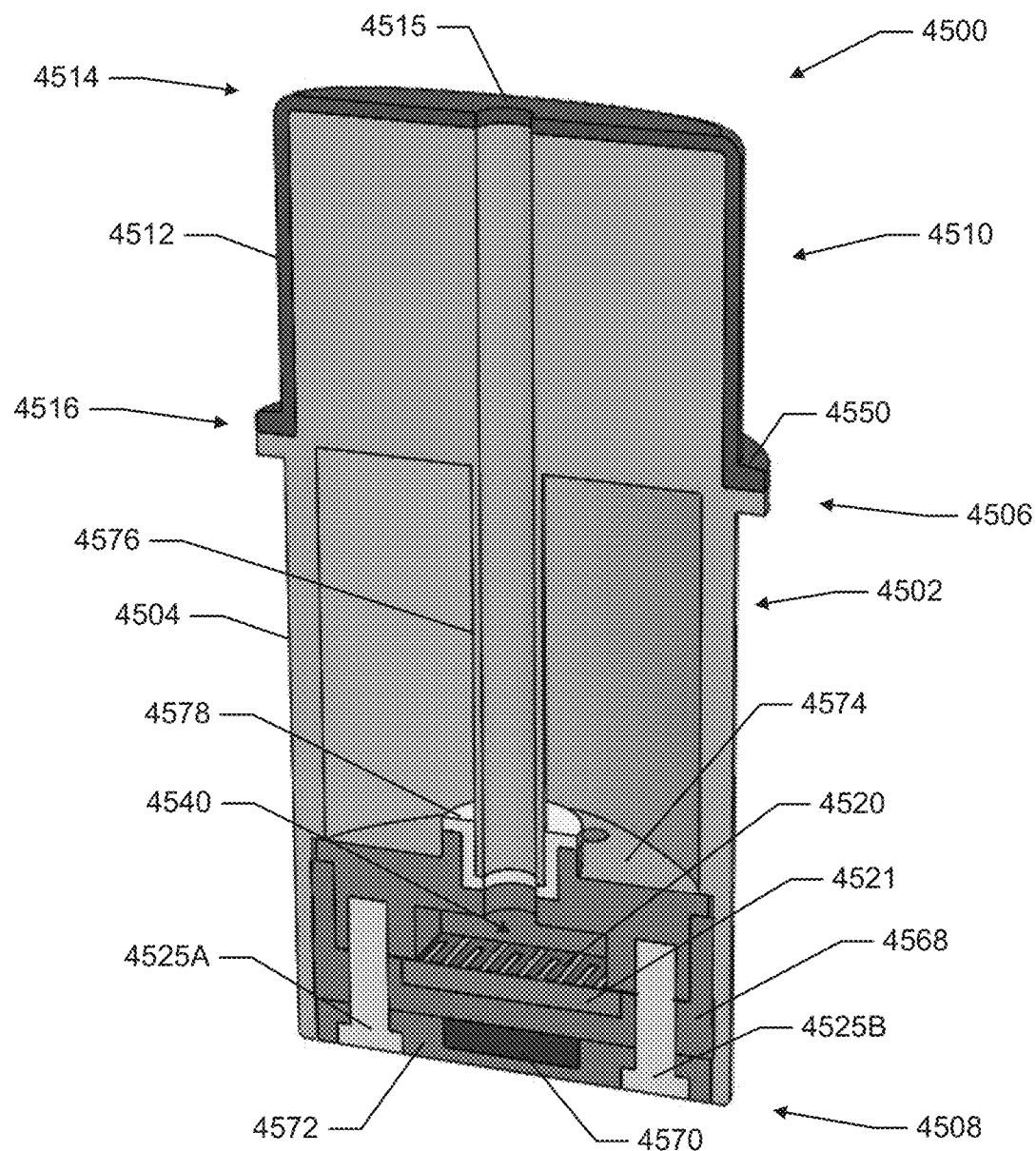
Figure 41:
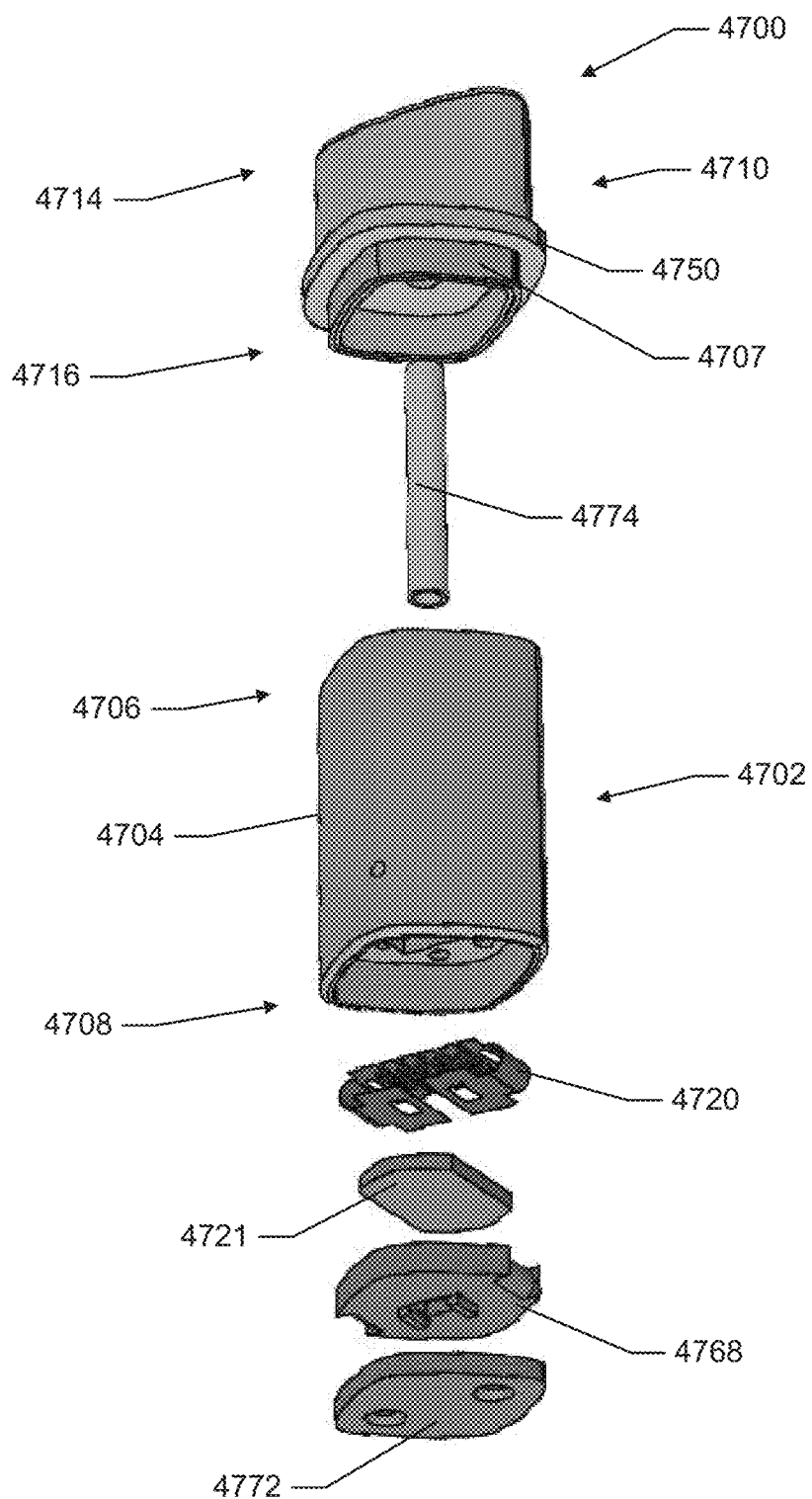
Figure 42:
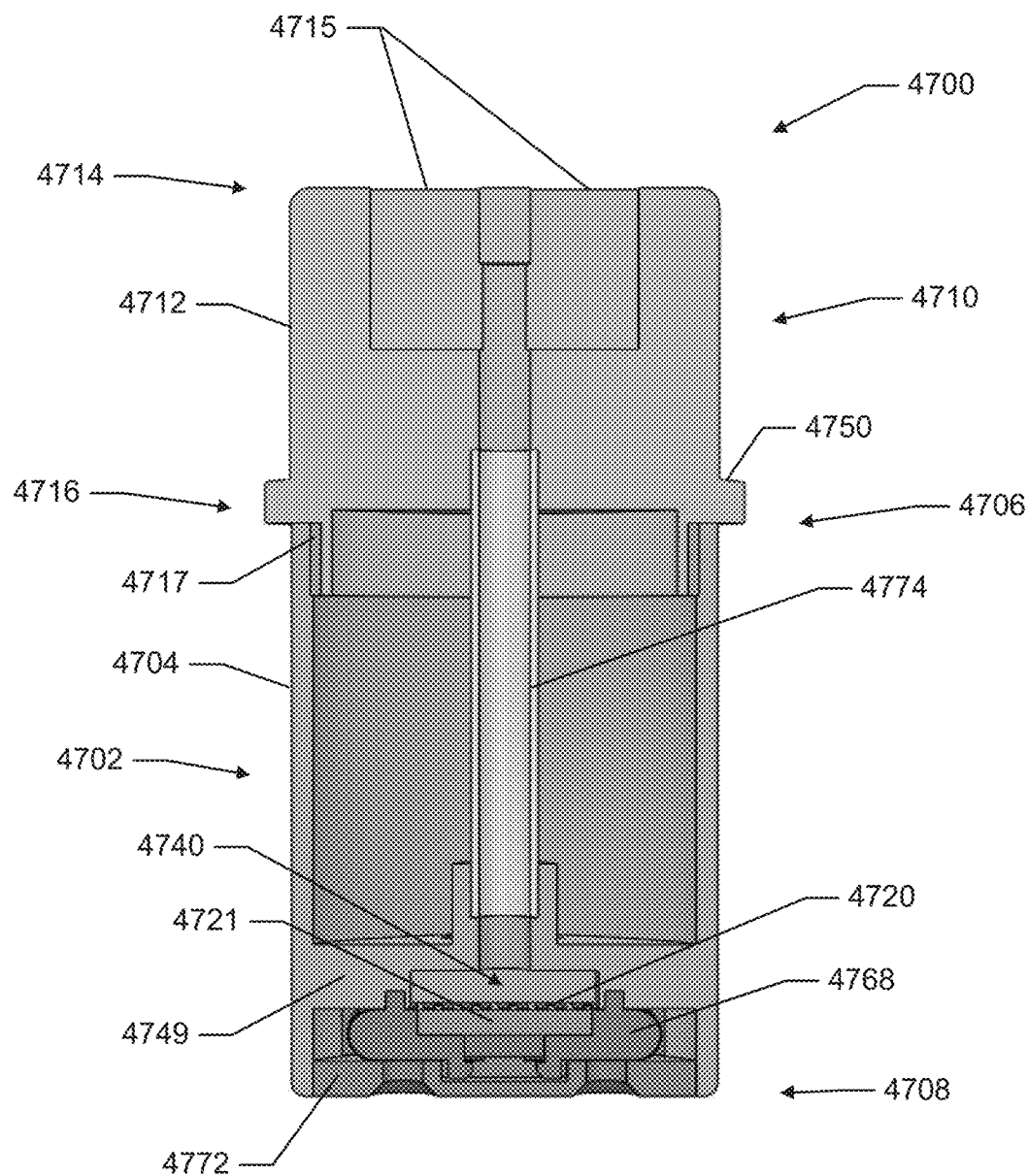
Figure 43:
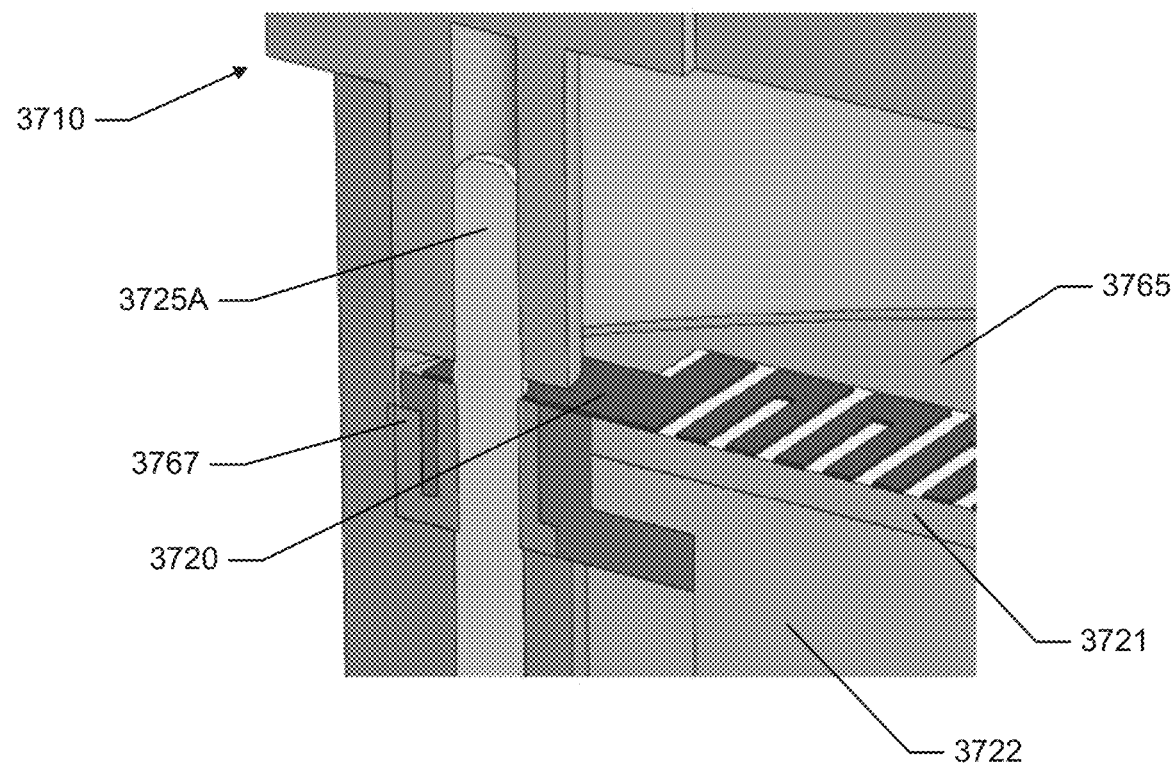
Figure 44:
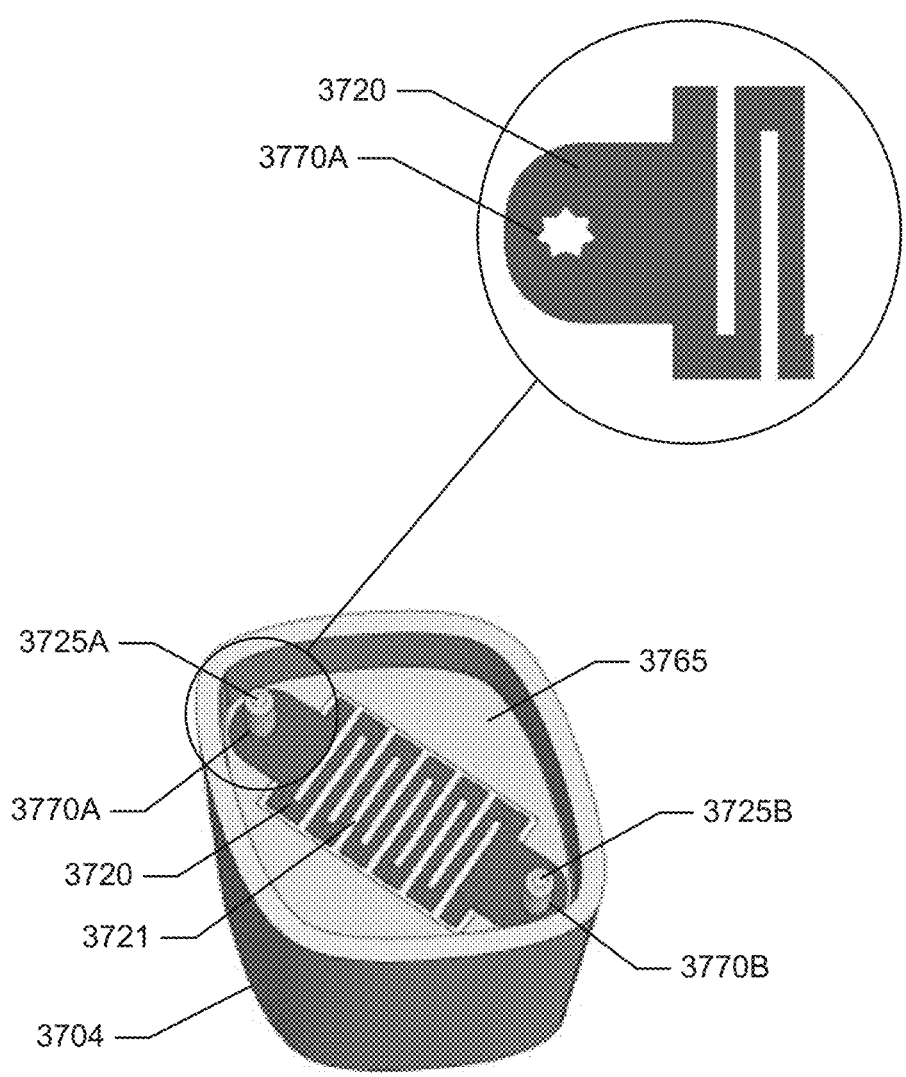
Figure 45:
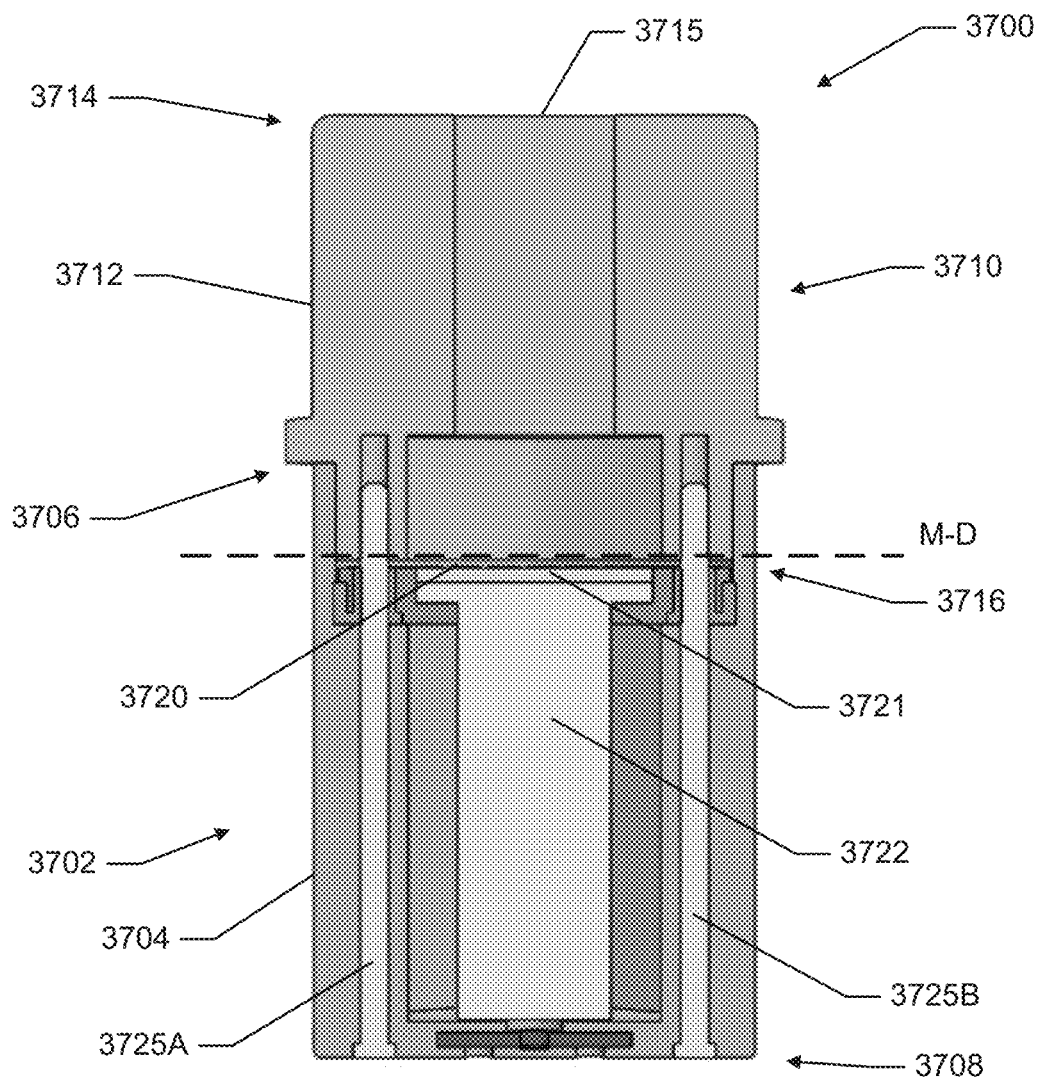

Having thus described the disclosure in the foregoing general terms, reference will now be made to the accompanying drawings, which are not necessarily drawn to scale, and wherein:

FIG. 1 illustrates a perspective view of an aerosol delivery device according to an example implementation of the present disclosure;

FIG. 2 illustrates a partial front cross-section view of the control device of the aerosol delivery device illustrated in FIG. 1 according to an example implementation of the present disclosure;

FIG. 3A illustrates a perspective view of a cartridge according to an example implementation of the present disclosure;

FIG. 3B illustrates a partial front cross-section view of a cartridge according to an example implementation of the present disclosure;

FIG. 4 illustrates an exploded perspective view of a cartridge according to an example implementation of the present disclosure;

FIG. 5A illustrates a partial side cross-section view of a cartridge according to an example implementation of the present disclosure;

FIG. 5B illustrates a partial close-up side cross-section view of a cartridge according to an example implementation of the present disclosure;

FIG. 6 illustrates an exploded perspective view of a cartridge according to an example implementation of the present disclosure;

FIG. 7A illustrates a partial side cross-section view of a cartridge according to an example implementation of the present disclosure;

FIG. 7B illustrates a partial close-up side cross-section view of a cartridge according to an example implementation of the present disclosure;

FIG. 8 illustrates an exploded perspective view of a cartridge according to an example implementation of the present disclosure;

FIG. 9 illustrates a partial front cross-section view of a cartridge according to an example implementation of the present disclosure;

FIG. 10 illustrates an exploded perspective view of a cartridge according to an example implementation of the present disclosure;

FIG. 11 illustrates a partial front cross-section view of a cartridge according to an example implementation of the present disclosure;

FIG. 12 illustrates an exploded perspective view of a cartridge according to an example implementation of the present disclosure;

FIG. 13 illustrates a partial front cross-section view of a cartridge according to an example implementation of the present disclosure;

FIG. 14 illustrates a partial front cross-section view of a cartridge according to an example implementation of the present disclosure;

FIG. 15 illustrates an exploded perspective view of a cartridge according to an example implementation of the present disclosure;

FIG. 16 illustrates a partial front cross-section view of a cartridge according to an example implementation of the present disclosure;

FIG. 17 illustrates a partial front cross-section view of a cartridge according to an example implementation of the present disclosure;

FIG. 18 illustrates an exploded perspective view of a cartridge according to an example implementation of the present disclosure;

FIG. 19 illustrates a partial front cross-section view of a cartridge according to an example implementation of the present disclosure;

FIG. 20 illustrates a partial perspective cross-section view of a cartridge according to an example implementation of the present disclosure;

FIG. 21 illustrates an exploded perspective view of a cartridge according to an example implementation of the present disclosure;

FIG. 22 illustrates a partial front cross-section view of a cartridge according to an example implementation of the present disclosure;

FIG. 23 illustrates an exploded perspective view of a cartridge according to an example implementation of the present disclosure;

FIG. 24 illustrates a partial front cross-section view of a cartridge according to an example implementation of the present disclosure;

FIG. 25 illustrates a partial front cross-section view of a cartridge according to an example implementation of the present disclosure;

FIG. 26 illustrates a partial front cross-section view of a cartridge according to an example implementation of the present disclosure;

FIG. 27 illustrates an exploded perspective view of a cartridge according to an example implementation of the present disclosure;

FIG. 28 illustrates a partial perspective cross-section view of a cartridge, according to an example implementation of the present disclosure;

FIG. 29 illustrates an exploded perspective view of a cartridge according to an example implementation of the present disclosure;

FIG. 30 illustrates a partial perspective cross-section view of a cartridge according to an example implementation of the present disclosure;

FIG. 31 illustrates an exploded perspective view of a cartridge according to an example implementation of the present disclosure;

FIG. 32 illustrates a partial perspective cross-section view of a cartridge according to an example implementation of the present disclosure;

FIG. 33 illustrates an exploded perspective view of a cartridge according to an example implementation of the present disclosure;

FIG. 34 illustrates a partial front cross-section view of a cartridge according to an example implementation of the present disclosure;

FIG. 35 illustrates an exploded perspective view of a cartridge according to an example implementation of the present disclosure;

FIG. 36 illustrates a partial front cross-section view of a cartridge according to an example implementation of the present disclosure;

FIG. 37 illustrates an exploded perspective view of a cartridge according to an example implementation of the present disclosure;

FIG. 38 illustrates a partial front cross-section view of a cartridge according to an example implementation of the present disclosure;

FIG. 39 illustrates an exploded perspective view of a cartridge according to an example implementation of the present disclosure;

FIG. 40 illustrates a partial perspective cross-section view of a cartridge according to an example implementation of the present disclosure;

FIG. 41 illustrates an exploded perspective view of a cartridge according to an example implementation of the present disclosure;

FIG. 42 illustrates a partial front cross-section view of a cartridge according to an example implementation of the present disclosure;

FIG. 43 illustrates a partial perspective cross-section view of a portion of a cartridge according to an example implementation of the present disclosure;

FIG. 44 illustrates a partial perspective view of a portion of a cartridge according to an example implementation of the present disclosure; and FIG. 45 illustrates a partial front cross-section view of a cartridge according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize (e.g., atomize, aerosolize, etc.) a material (preferably without combusting the material to any significant degree and/or without significant chemical alteration of the material) to form an inhalable substance; and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of an aerosol precursor composition. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol delivery device of the present disclosure can hold and use the device much like a smoker employs a traditional type of smoking article, draw on one end of the device for inhalation of aerosol produced by the device, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for aerosol generation, such as by controlling electrical current flow the power source to other components of the article—e.g., a microcontroller or microprocessor), an atomizing member (e.g., a piezoelectric vibration element or a heating member such as, for example, an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat or other energy, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure relates to aerosol delivery devices and cartridges for aerosol delivery devices that include one or more components configured for vaporizing a liquid composition and one or more components configured to deliver liquid to the one or more components configured for vaporizing the liquid. In various implementations, the one or more vaporizing components and the one or more liquid transport components may be positioned in various locations within the cartridge.

An example implementation of an aerosol delivery device 100 of the present disclosure is shown in FIG. 1. As illustrated, the aerosol delivery device 100 includes a control device 200 and a removable cartridge 300. Although only one cartridge is shown in the depicted implementation, it should be understood that, in various implementations, the aerosol delivery device 100 may comprise an interchangeable system. For example, in one or more implementations, a single control device may usable with a plurality of different cartridges. Likewise, in one or more implementations, a single cartridge may be usable with a plurality of different control devices.

In various implementations, the control device 200 includes an outer housing 202 that defines an outer wall 204, which includes a distal end 206 and a proximal end 208. The aerosol delivery device 100 of the depicted implementation also includes an indication window 240 defined in the outer housing 202. It should be noted, however, that in some implementations there may not be an indication window. FIG. 2 illustrates a partial cross-section of the control device 200 of the aerosol delivery device 100 of FIG. 1. As shown in the figure, the control device 200 also includes an inner frame 215 that includes a cartridge receiving chamber 212 defined by an inner frame wall 214. The control device 200 further includes a battery 216 positioned within the outer housing 202 and also includes an external connection element 218. In the depicted implementation, the external connection element 218 is positioned at the distal end 206 of the outer housing 202. The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., the disclosure of which is incorporated herein by reference.

In various implementations, the control device 200 may also include a light source 230 and at least one aperture 232 (see FIG. 1) defined in the outer wall 204 of the control device 200 and through which light from the light source 230 may be visible. In some implementations, the light source 230 may comprise, for example, at least one light emitting diode (LED) capable of providing one or more colors of light. In some implementations, the light source may be configured to illuminate in only one color, while in other implementations, the light source may be configured to illuminate in variety of different colors. In still other implementations, the light source may be configured to provide white light. As illustrated in FIG. 2, the light source 230 may be positioned directly on a control component 234 (such as, for example a printed circuit board (PCB)) on which further control components (e.g., a microcontroller and/or memory components) may be included. In various implementations, the aperture 232 may be provided in any desired shape and may particularly be positioned near the distal end 206 of the control device 200. In some implementations, the aperture 232 may be completely open or may be filled, such as with a light guide material, or may be covered with a transparent or translucent member (e.g., glass or plastic, or another material such as a fibrous polymer sheet material) on one or both of the inner surface and the outer surface of the outer wall 204 of the control device 200. The aerosol delivery device 100 may also include a control mechanism for controlling the amount of electric power to the atomizing member during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

Electrical connectors 220 may be positioned in the cartridge receiving chamber 212 and, in the depicted implementation, are present in sides of the inner frame wall 214. In various implementations, the electrical connectors 220 may be operatively connected to the battery (e.g. connected to the battery directly or via the control component 234). The electrical connectors may have a variety of forms and may be positioned in various other locations of the inner frame 215. As also illustrated in FIG. 2, the proximal end 208 of the outer housing 202 includes an opening 210 that provides access to the cartridge receiving chamber 212 defined by the inner frame 215. It should be noted that for the purposes of the present disclosure, the terms "connected" and "operatively connected" should be interpreted broadly so as to encompass components that are directly connected and/or connected via one or more additional components.

In various implementations, further indicators (e.g., a haptic feedback component, an audio feedback component, or the like) can be included in addition to or as an alternative to the light source. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that not all of the illustrated elements are required. For example, an LED may be absent or may be replaced with a different indicator, such as a vibrating indicator.

In various implementations, an airflow sensor, pressure sensor, or the like may be included in the device. For example, as illustrated in FIG. 2, the control device 200 may include a sensor 236 on the control component 234. Configurations of a printed circuit board and a pressure sensor, for example, are described in U.S. Pat. App. Pub. No. 2015/0245658 to Worm et al., the disclosure of which is incorporated herein by reference in its entirety. In various implementations, the sensor 236 may be positioned anywhere within the control device 200 so as to be subjected to airflow and/or a pressure change that can signal a draw on the device and thus cause the battery 216 to delivery power to the atomizing member in the cartridge 300. Alternatively, in the absence of an airflow sensor, the atomizing member may be activated manually, such as via a push button that may be located on the control body 200 and/or the cartridge 300. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, an input element may be included with the aerosol delivery device (and may replace or supplement an airflow or pressure sensor). The input may be included to allow a user to control functions of the device and/or for output of information to a user. Any component or combination of components may be utilized as an input for controlling the function of the device 100. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pub. 2016/0158782 to Henry et al., which is incorporated herein by reference in its entirety.

In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Although other implementations may differ, in the depicted implementation, the inner frame 215 is separate from the outer housing 202. In such a manner, the inner frame 215 defining the cartridge receiving chamber 212 may exist independently and separately from the outer housing 202. An opening of the chamber may coincide with an opening at the proximal end 208 of the outer housing 202. Thus, in the depicted implementation, the inner frame wall 214 may be a completely different element that is attached to the outer housing 202; however, in other implementations the inner frame wall and the outer housing may be continuously formed. In either case, the sidewalls forming the inner frame wall are present interior to and separated from the outer housing.

In various implementations, the outer housing 202 may be formed of any suitable material, such as a metal, plastic, ceramic, glass, or the like. In some implementations, the inner frame 215 may be formed of a different material than that used to form the outer housing 202. For example, in some implementations the outer housing may comprise a metal material, and the inner frame may comprise a plastic material. In other implementations, the same materials may be used. Choice of materials as noted above may also extend to the outer housing for any further control device(s) that are included in the device. For example, in some implementations the housing and the inner frame may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof). In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

An example implementation of a cartridge 300 for use in an aerosol delivery device of the present disclosure is shown in FIGS. 3A and 3B. In particular, FIG. 3A is a perspective view of a cartridge according to example implementations of the present disclosure, and FIG. 3B is a partial cross-section view of the cartridge illustrated in FIG. 3. As shown in FIGS. 3A and 3B, the cartridge 300 includes a tank portion 302 that is defined by an outer tank wall 304 that includes a proximal end 306 and a distal end 308, which is closed. As such, the tank portion 302 may be characterized in that the tank wall 304 is a sidewall that is continuous around the tank, and the distal end 308 defines a bottom wall. The tank portion 302 is also configured to contain a liquid composition 324 for vaporization (e.g., an e-liquid or aerosol precursor composition), which may be configured as otherwise described herein. The cartridge 300 also includes a mouthpiece portion 310 that is defined by an outer mouthpiece wall 312 that includes a proximal end 314 with an exit portal 315 defined therein, and a distal end 316 that engages the proximal end 306 of the tank portion 302.

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the liquid composition, sometime referred to as an aerosol precursor composition or a vapor precursor composition or "e-liquid", may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference. Other aerosol precursors that may be employed include the aerosol precursors that have been incorporated in VUSE® products by R. J. Reynolds Vapor Company, the BLU™ products by Fontem Ventures B. V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating device provides acceptable sensory and desirable performance characteristics. For example, it is highly preferred that sufficient amounts of aerosol forming material (e.g., glycerin and/or propylene glycol), be employed to provide for the generation of a visible mainstream aerosol that in many regards resembles the appearance of tobacco smoke. The amount of aerosol precursor within the aerosol generating system may be dependent upon factors such as the number of puffs desired. In one or more embodiments, about 1 ml or more, about 2 ml or more, about 5 ml or more, or about 10 ml or more of the aerosol precursor composition may be included.

In some implementations, the liquid composition 324 may include one or more flavorants. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

In various implementations, the overall cartridge 300 and/or the mouthpiece portion 310 and/or the tank portion 302 may separately be defined in relation to a longitudinal axis (L), a first transverse axis (T1) that is perpendicular to the longitudinal axis, and a second transverse axis (T2) that is perpendicular to the longitudinal axis and is perpendicular to the first transverse axis. As shown in FIG. 3B, the cartridge 300 further includes an atomizing member configured to vaporize the liquid composition. In the depicted implementation, the atomizing member comprises a heating member 320. Although the atomizing member of the depicted implementation comprises a heating member configured to heat the liquid composition to vaporize the composition to form an aerosol, in other implementations, the atomizing member may comprise any device, element, or assembly configured to vaporize (e.g., atomize, aerosolize, etc.) the liquid composition to form an aerosol, including, for example, atomizing nozzle devices, and piezoelectric devices, such as devices that are configured to cause the liquid composition to undergo vibration (e.g., ultrasonic vibration) that vaporizes the composition to form an aerosol. In various implementations, such devices may utilize electrical power from the power source for the production of the aerosol. Some examples of piezoelectric vibration devices are described in U.S. Pat. App. Pub. No. 2013/0319404 to Amir et al., which is incorporated herein by reference in its entirety.

The cartridge further includes a liquid transport element 321, at least a portion of which is positioned proximate (e.g., directly adjacent, adjacent, in close proximity to, or in relatively close proximity to) the heating member 320. The liquid transport element 321 of the depicted implementation extends between the heating member 320 and the liquid composition 324 contained within the tank portion 302. In the depicted implementation, at least a portion of the heating member 320 is located above the proximal end 306 of the tank portion 302. For the purposes of the present disclosure, it should be understood that the term "above" in this particular context should be interpreted as meaning toward the proximal end 314 of the mouthpiece portion 310 in direction substantially along the longitudinal axis (L), as shown in FIG. 3B.

In various implementations, the heating member 320 and liquid transport element 321 may be configured as separate elements that are fluidly connected or may be configured as a combined element. Moreover, the heating member 320 and the liquid transport element 321 may be formed of any construction as otherwise described herein. The cartridge 300 also includes one or more electrical contacts 325 that are configured to electrically connect the heating member 320 with the battery 216 and/or control component 234 of the control device 200. It should be noted that in some implementations, a heating member and a liquid transport element may be combined into a single component. For example, in some implementations a heating member may be integrated into a liquid transport element. Some examples of such components are described in U.S. Pat. No. 8,833,364 to Buchberger and U.S. Pat. App. Pub. No. 2017/0203057 to Buchberger, each of which is incorporated herein by reference in its entirety.

In various implementations, the liquid transport element 321 may be formed of one or more materials configured for transport of a liquid, such as by capillary action. In some implementations, for example, a liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element 321 thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. App. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element 321 may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. App. Pub. No. 2014/0123989 to LaMothe, the disclosures of which are incorporated herein by reference in their entireties. In some implementations, the porous monolith may form a substantially solid (e.g., non-hollow) wick.

In various implementations, the heating member 320 may comprise one or more different materials configured to produce heat when electrical current is applied therethrough. In some implementations, the heating member 320 may be a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum (Mo(Si, Al)$_2$), titanium, platinum, silver, palladium, alloys of silver and palladium, graphite and graphite-based materials (e.g., carbon-based foams and yarns). In further implementations, the heating member 320 may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heating member 320 in particular may be configured to be substantially flat. Some examples of such heaters are described in U.S. Pat. App. Pub. No. 2016/0345633 to DePiano et al., which is incorporated herein by reference in its entirety.

In the depicted implementation, the outer tank wall 304 is configured to be one of at least partially transparent or translucent so that the liquid composition 324 contained therein is visible externally. As such, in some implementations, the entire outer tank wall 304 may be transparent or translucent. Alternatively, in some implementations, only a single side, or a portion (or portions) of one or more sides, of the outer tank wall 304 may be transparent or translucent while the remaining portions of the outer tank wall may be substantially opaque. In some embodiments, the outer tank wall 304 or a portion thereof may be substantially opaque, and a strip (e.g., about 1 mm wide to about 20 mm wide or about 2 mm wide to about 18 mm wide or about 5 mm wide to about 15 mm wide) extending from the proximal end 306 of the tank portion 302 to the distal end 308 of the tank may be transparent or translucent. In further implementations, the outer tank wall 304 may be colored. In some implementations, the color can be configured so that the liquid composition 324 within the tank portion 302 is still visible, such as by using a transparent or translucent outer tank wall. In other implementations, the tank wall can be configured so that the outer tank wall 304 has a substantially opaque color.

In some implementations, the control device 200 may be configured so that at least a portion of the tank portion 302 is visible when the cartridge 300 is engaged with the control device 200. As noted above, in some implementations, at least a portion of the outer tank wall 304 may be configured to be one of at least partially transparent or translucent so that the liquid composition 324 contained therein is visible externally, and the outer wall 204 of the control device 200 may be configured to include an indication window 240 (see FIGS. 1 and 2) through which a portion of the outer tank wall 304 and any liquid composition 324 present in the tank portion 302 can be visible when the cartridge 300 is engaged with the control device 200.

In one or more implementations, the cartridge 300 may be configured such that the mouthpiece wall 312 includes a flange positioned between the proximal end 314 and the distal end 316 thereof. For example, referring to FIGS. 3A and 3B, the mouthpiece 310 includes a flange 350 that extends circumferentially from the mouthpiece wall 312 around substantially the entirety of the mouthpiece 310. In some implementations, the distance that the flange 350 extends from the mouthpiece wall 310 can be substantially uniform around the entire circumference of the mouthpiece 310. In other implementations (such as the depicted implementation) the distance that the flange 350 extends from the mouthpiece wall 312 may vary at one or more points around the circumference of the mouthpiece 310. Still other implementations may not include a flange.

In various implementations, the electrical contacts 325, when present in the mouthpiece wall 312, may be positioned longitudinally between the flange 350 and the distal end 316 of the mouthpiece portion 310. Further, in some implementations, the flange 350 may be substantially in line with the interior upper wall 332. As such, the flange 350 may be substantially parallel with and/or may be substantially in the same horizontal plane with the interior upper wall 332. In some implementations, the flange 350 may be positioned above the vaporization chamber 340 and above the heating member 320 along the longitudinal axis (L) of the mouthpiece portion 310.

In various implementations, the flange 350 may interact with a corresponding lip on the control device 200 to ensure proper connection of the cartridge 300 with the control device 200. For example, referring to FIG. 2, the control device 200 may be configured so that the opening 210 at the proximal end 208 thereof includes a recess with a first inwardly projecting lip 221. The recess thus may comprise a rim wall 222 that is substantially parallel with the longitudinal axis of the device 100. The rim wall 222 may extend downwardly from the proximal end 208 a short distance, which distance may substantially correspond to a thickness of the flange 350 of the cartridge 300 and/or the thickness of a further element that may be present adjacent the flange. For example, in some implementations, the rim wall 222 forming the downwardly extending recess may have a height (i.e., as measured from a top surface of the inwardly projecting lip 221 to the first device proximal end 208) of about 1 mm to about 8 mm, about 1 mm to about 6 mm, or about 1 mm to about 5 mm. The inwardly projecting lip 221 may have a width (i.e., the distance the lip extends inward from the rim wall 222 to a terminal end) of about 1 mm to about 8 mm, about 1 mm to about 6 mm, or about 1 mm to about 5 mm. In some implementations, the inwardly projecting lip 221 may have a substantially constant width around the entire circumference of the opening 210. In other embodiments, the inwardly extending lip 221 may be discontinuous and thus may be formed of one or a plurality of inwardly extending lips spaced around the opening 210. In various implementations, the flange 350 of the mouthpiece portion 310 is configured to be at least partially received within the recess formed by the rim wall 222 so as to contact the inwardly projecting lip 221. As such, a bottom surface of the flange 350 may be substantially in contact with the inwardly projecting lip 221, and an outer edge of the flange may be substantially adjacent the rim wall 222.

In some implementations, the flange 350 and/or the inwardly projecting lip 221 may be configured to bias the cartridge 300 into connection with the control device 200. For example, a magnetic connection may be utilized. As illustrated in FIG. 3B, the cartridge 300 may include a magnet 352 positioned adjacent a bottom surface of the first flange 350. In various implementations, the magnet 352 may extend substantially completely around the circumference of the mouthpiece portion 310 or may be discontinuous so as to be configured as one or a plurality of discrete magnets. In various implementations, the magnet 352 may be adhered to the mouthpiece wall 312, may be adhered to the flange 350, or may be adhered to both the mouthpiece wall 312 and the flange 350. The inwardly projecting lip 221 may be formed of a metal or other material to which the magnet 352 will be attracted by magnetic force. In further implementations, the magnet 352 may be positioned on the control device 200. Specifically, the magnet 352 may be adhered to the inwardly extending lip 221. In such implementations, the flange 350 may be formed of a metal or other material to which the magnet 352 will be attracted by magnetic force. In further implementations, a magnet may be present on the cartridge 300 as well as the control device 200. As such, a magnet present adjacent the lower surface of the flange 350 on the cartridge 300 may be attracted by magnetic force to a magnet present adjacent the upper surface of the inwardly projecting lip 221 on the control device 200. When a magnet is present on the mouthpiece portion 310, it is preferable that the combined thickness of the magnet and the flange 350 is substantially identical to the height of the rim wall 222 on the control device 200 so that an upper surface of flange is substantially flush with the proximal end 208 of the device when the cartridge and the device are engaged.

In various implementations, the aerosol delivery device 100 and/or the control device 200 of the aerosol delivery device 100 may further include an external connector configured for electrical contact with each of the device external connection element (e.g., device external connection element 218). The external connector may include a first connector end and a second connector end interconnected by a union, which may be, for example, a cord of variable length. In various implementations, the first connector end may be configured for electrical and, optionally, mechanical connection with the control device. In particular, the first connector end may include an inset wall that can be received within a well present at the distal end 206 of the control device 200. The external connector may include a plurality of electrical pins interior to the inset wall configured for making a charging and/or information transferring connection with the device external connection element 218. In some implementations, the control device 200 may include a mechanical connector (e.g., a mechanical connector 242) adjacent the control device external connection element 218. In some implementations, the mechanical connector 242 may be a magnet or a metal (or like element) that is adapted for magnetic attraction to a magnet. The first connector end of the external connection may then likewise include a mechanical connection element that may be positioned between the inset wall and the electrical pins. In various implementations, the mechanical connection element may be a magnet or a metal (or like element) that is adapted for magnetic attraction to a magnet. The second connector end may be configured for connection to a computer or similar electronic device or for connection to a power source. For example, the second connector end may have a Universal Serial Bus (USB) connection; however, a different connection may also be provided and/or an adapter may likewise be included (e.g., a USB/AC adapter). For example, an adaptor including a USB connector at one end and a power unit connector at an opposing end is disclosed in U.S. Pat. App. Pub. No. 2014/0261495 to Novak et al., which is incorporated herein by reference.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, the mouthpiece portion 310 of the cartridge 300 may be configured for engagement with the tank portion 302. For example, as illustrated in FIG. 3B, the distal end 316 of the mouthpiece portion 310 may include a rim wall 330 that is at least partially inset from the outer mouthpiece wall 312. The rim wall 330 may be configured to engage an interior of the proximal end 306 of the outer tank wall 304. In some implementations, the rim wall 330 may have a length of about 1 mm to about 20 mm, about 2 mm to about 18 mm, or about 5 mm to about 15 mm, although other configurations are possible. In some implementations, the rim wall 330 may engage the outer tank wall 304 via a friction fit alone, or the rim wall may be substantially permanently attached to the outer tank wall, such as through welding or gluing via one or more adhesives.

In some implementations, the mouthpiece portion 310 may define an open interior space through which formed vapor may combine with air to form an aerosol for output through the exit portal 315 of the mouthpiece portion 310. In one or more implementations, the mouthpiece 310 may include one or more further interior walls that can be arranged to define one or more compartments within the mouthpiece. For example, the mouthpiece may include an interior upper wall between the proximal end and the distal end of the mouthpiece and also include an interior lower wall between the interior upper wall and the proximal end of the mouthpiece. More particularly, as seen in FIG. 3B, the mouthpiece portion 310 may include an interior upper wall 332 between the proximal end 314 and the distal end 316 of the mouthpiece portion 310. Further, the mouthpiece portion 310 may include an interior lower wall 334 between the interior upper wall 332 and the distal end 316 of the mouthpiece portion 310.

In various implementations, two or more walls in the mouthpiece may be configured to define a vaporization chamber within which the heating member 320 may be positioned. As shown in FIG. 3B, the outer mouthpiece wall 312, the interior upper wall 332, and the interior lower wall 334 define a vaporization chamber 340 wherein the heating member 320 is positioned. In some implementations, the one or more electrical contacts 325 may be positioned within the portion of the outer mouthpiece wall 312 defining the vaporization chamber 340; however, it is understood that one or more electrical leads may extend from the heating member 320 to one or more electrical contacts positioned at a different portion of the outer mouthpiece wall or positioned in the outer tank wall 304. One or more walls of the mouthpiece may also include one or more openings for passage therethrough of one or more further elements of the cartridge 300 or passage of formed vapor/aerosol. For example, the interior upper wall 332 may include a vapor opening 336 through which vapor formed in the vaporization chamber 340 may pass toward the first exit portal 315. In some implementations, the vapor opening 336 in the interior upper wall 332 may be substantially centrally located therein and may be substantially aligned with the heating member 320 along a longitudinal axis of the cartridge 300. As a further example, the interior lower wall 334 may include a wick aperture 338 through which the first liquid transport element 321 (e.g., a wick) can pass between the heating member 320 and the liquid composition 324 in the tank portion 302.

In various implementations, two or more walls in the mouthpiece may be configured to define a cooling chamber within which formed aerosol can be allowed to expand and/or cool before passing through the exit portal. As shown in FIG. 3B, for example, the outer mouthpiece wall 312 and the interior upper wall 332 define a cooling chamber 342 that receives formed vapor/aerosol from the vaporization chamber 340. As such, the vapor/aerosol formed by the heating member 320 passes from the vaporization chamber 340 through the vapor opening 336 and into the cooling chamber 342. In some implementations, the vaporization chamber 340 and the cooling chamber 342 may be configured to have a defined relative volume ratio. For example, in some implementations, the volume ratio of the vaporization chamber 340 to the cooling chamber 342 can be about 2:1 to about 1:4, about 1:1 to about 1:4, or about 1:1.5 to about 1:3, although other configurations are possible.

If desired, the mouthpiece 310 may also include one or more elements configured to reduce or prevent leakage of condensed liquids therefrom. For example, in some implementations, all or a part of the interior of the mouthpiece wall 312 and/or the interior upper wall 332 defining the cooling chamber 342 may be formed from or include an absorptive or adsorptive material configured to hold liquid. Alternatively or additionally, all or a part of the interior of the mouthpiece wall 312 and/or the interior upper wall 332 defining the cooling chamber 342 may be configured to direct liquid back toward the vaporization chamber 340, such as through the addition of microchannels or the like.

In some implementations, the overall cartridge 300 and/or the mouthpiece 310 thus may be defined in relation to a total length along the longitudinal axis (L), a total width along the first transverse axis (T1), and a total depth along the second longitudinal axis (T2). The length may be greater than the width, which in turn may be greater than the depth. The distance that the flange 350 extends away from the mouthpiece wall 312 may be greater along the second transverse axis (T2) than along the first transverse axis (T1). Thus, in some implementations, the total distance between opposing outer edges of the flange 350 across the mouthpiece 310 along the first transverse axis (T1) may be greater than the total distance between opposing edges of the flange across the mouthpiece along the second transverse axis (T2); the total distance between opposing outer edges of the flange 350 across the mouthpiece 310 along the first transverse axis (T1) may be substantially equal to the total distance between opposing edges of the flange across the mouthpiece along the second transverse axis (T2); or the total distance between opposing outer edges of the flange 350 across the mouthpiece 310 along the first transverse axis (T1) may be less than the total distance between opposing edges of the flange across the mouthpiece along the second transverse axis (T2). In particular implementations, a distance (d2) between the mouthpiece wall 312 and an outer edge of the flange 350 as measured along the second transverse axis (T2) may be greater than a distance between the mouthpiece wall and an outer edge of the flange as measured along the first transverse axis (T1). Said distances particularly may be as measured at about a midpoint of each of the first transverse axis (T1) and the second transverse axis (T2).

In the depicted implementation, one or more of the mouthpiece portion 310 and the tank portion 302 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. In the depicted implementation, the mouthpiece portion 310 is configured to be joined to the tank portion 302 via a press or snap-fit connection; however, in other implementations, other attachment methods are possible (e.g., via adhesives, heat staking/welding, ultrasonic welding, etc.) or any combination thereof.

FIGS. 4, 5A, and 5B illustrate a cartridge in accordance with another implementation of the present disclosure. In particular, FIG. 4 illustrates an exploded perspective view of a cartridge 500 according to an example implementation of the present disclosure, FIG. 5A illustrates a partial cross-section view of the cartridge 500, and FIG. 5B illustrates a partial close-up cross-section view of the cartridge 500. In various implementations, a portion of the cartridge 500 is configured to be removably coupled with a cartridge receiving chamber of a corresponding control device. In many aspects, the cartridge 500 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to FIG. 4, the cartridge 500 of the depicted implementation includes a tank portion 502 that is defined by an outer tank wall 504 that includes a proximal end 506 and a distal end 508. As such, the tank portion 502 may be characterized in that the tank wall 504 is a sidewall that is continuous around the tank, and the distal end 508 defines a bottom wall. The tank portion 502 is also configured to contain a liquid composition 524 configured for vaporization (e.g., an e-liquid or aerosol precursor composition, as described above). The cartridge 500 also includes a mouthpiece portion 510 that is defined by an outer mouthpiece wall 512 that includes a distal end 516 and a proximal end 514 with an exit portal 515 defined therein. In the depicted implementation, the cartridge 500 also includes a collar portion 560 that is positioned between the mouthpiece portion 510 and the tank portion 502. In the depicted implementation, the collar portion 560 is configured to be joined to the mouthpiece portion 510 and the tank portion 502 via a press or snap-fit connection; however, in other implementations, other attachment methods are possible (e.g., via adhesives, heat staking/welding, ultrasonic welding, etc.) or any combination thereof.

In some implementations, the outer tank wall 504 may be configured to be one of at least partially transparent or translucent so that the liquid composition 524 contained therein is visible externally. As such, in some implementations, the entire outer tank wall 504 may be transparent or translucent. Alternatively, in some implementations, only a single side, or a portion (or portions) of one or more sides, of the outer tank wall 504 may be transparent or translucent while the remaining portions of the outer tank wall may be substantially opaque. In some embodiments, the outer tank wall 504 or a portion thereof may be substantially opaque, and a strip extending from the proximal end 506 of the tank 502 to the distal end 508 of the tank may be transparent or translucent. In further implementations, the outer tank wall 504 may be colored. In some implementations, the color can be configured so that the liquid composition 524 within the tank 502 is still visible, such by using a transparent or translucent outer tank wall. In other implementations, the tank wall can be configured so that the outer tank wall 504 has a substantially opaque color.

In the depicted implementation, one or more of the mouthpiece portion 502, the collar portion 560, and the tank portion 502 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in FIG. 4, the cartridge 500 further includes a heating member 520 and a pair of electrical contacts 525A, 525B that are configured to electrically connect the heating member 520 with the battery and/or control component of a control device. In the depicted implementation, the contacts 525A, 525B are located on opposite sides of the cartridge 500 and are configured to be attached to the collar portion 560. Although in the depicted implementation the contacts 525A, 525B are configured to be attached to the collar portion 560 via a press-fit or snap fit attachment, in other implementations other forms of attachment are possible, including, for example, via an adhesive or via an insert molding process. In the depicted implementation, the electrical contacts 525A, 525B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 520 may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum $(Mo(Si, Al))_2$, titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the hating member 520 may be integrated with the first liquid transport element 521. Other types of heating members (e.g., laser diodes, microheaters, etc.) may also be utilized, as noted above.

The cartridge 500 of the depicted implementation also includes a pair of liquid transport elements. In particular, the cartridge 500 includes a first liquid transport element 521, and a second liquid transport element 522. In the depicted implementation, at least a portion of the first liquid transport element 521 is configured to be located proximate the heating member 520. In addition, the second liquid transport element 522 of the depicted implementation is configured to extend between the first liquid transport element 521 and the liquid composition 524 contained within the tank 502 such that the second liquid transport element 522 is configured to transport liquid to the first liquid transport element 521. In the depicted implementation, the second liquid transport element 522 has a T-shape with a transverse portion 527 that intersects a longitudinal portion 529. Although other configurations are possible, in the depicted implementation, the length of the longitudinal portion 529 is longer than the length of the transverse portion 527.

As shown in FIGS. 5A and 5B, the first liquid transport element 521 and the heating member 520 are located in the collar portion 560 of the cartridge 500. When installed in the cartridge, the heating member 520 of the depicted implementation has a curved or bowed shape. In addition, when installed in the cartridge the first liquid transport element 521 of the depicted implementation also has curved or bowed shape. In particular, the heating member 520 of the depicted implementation comprises a flat heating element that, when installed in the cartridge 500, has a curved or bowed shape corresponding to (e.g., similar or approximately the same as) the curved shape of the top surface of the first liquid transport element 521 (or, in some implementations, vice versa). In such a manner, the heating member 520 in the installed position contacts a top surface of the first liquid transport element 521. In the depicted implementation, the curved form of the flat heating member 520 may provide a large ratio of cross-sectional flow area to flow path length through the first liquid transport element 521. When installed, the curvature of the heating member 520 may provide a compressive force against the first liquid transport element 521. The installed curvature of the heating member 520 may also bias deflection of the heating member 520 that may occur with thermal expansion towards the first liquid transport element 521, thus helping to maintain thermal contact between the heating member 520 and the first liquid transport element 521. Furthermore, when installed in the cartridge 500 the transverse portion 527 of the second liquid transport element 522 also has a curved or bowed shape corresponding to (e.g., similar to or approximately the same as) the curvature of the bottom surface of the first liquid transport element 521. In such a manner, a top surface of the transverse portion 527 of the second liquid transport element 522 contacts a bottom surface of the first liquid transport element 521. As such, one or more of these features may provide increased performance with respect to delivery of the liquid composition to the first liquid transport element 521.

In various implementations, one or both of the first liquid transport element 521 and the second liquid transport element 522 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 521 comprises a fibrous material and the second liquid transport element 522 comprises a semi-rigid material. In the depicted implementation, the second liquid transport element 522 is configured to be press-fit into the collar portion 560, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. App. Pub. No. 2014/0123989 to LaMothe, the disclosures of which are incorporated herein by reference in their entireties. In some implementations, the porous monolith may form a substantially solid (e.g., non-hollow) wick.

In the depicted implementation, the cartridge 500 further includes a hood feature 562 (which in the depicted implementation is a curved hood feature), a portion of which is configured to be located above (e.g., downstream from) the heating member 520 and within the collar portion 560. In the depicted implementation, the hood feature 562 is configured to direct aerosol, collect condensation, and/or shield against liquid and high temperatures from directly exiting the cartridge 500. In the depicted implementation, the hood feature 562 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, the hood feature may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. The hood feature 562 of the depicted implementation has curvature that opposes the curvature of the heating member 520. For example, in the depicted implementation the heating member 520 has a concave curvature (with respect to the mouthpiece end of the longitudinal axis shown in FIG. 3A), whereas the hood feature 562 has a convex curvature. In the depicted implementation, the heating member 520 and the hood feature 562 define at least a portion of a vaporization chamber 540. As noted above, aerosol is generated in the vaporization chamber 540 when the heating member 520 heats at least a portion of the liquid composition contained in the first liquid transport element 521. As such, when a user draws on the aerosol delivery device, aerosol from the vaporization chamber 540 may be diverted by the hood feature 562 and delivered to the user via the exit portal 515 of the mouthpiece portion 510.

FIGS. 6, 7A, and 7B illustrate a cartridge in accordance with another implementation of the present disclosure. In particular, FIG. 6 illustrates an exploded perspective view of a cartridge 700 according to an example implementation of the present disclosure, FIG. 7A illustrates a partial cross-section view of the cartridge 700, and FIG. 7B illustrates a partial close-up cross-section view of the cartridge 700. In various implementations, a portion of the cartridge 700 is configured to be removably coupled with a cartridge receiving chamber of a corresponding control device. In many aspects, the cartridge 700 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 700 of the depicted implementation includes a tank portion 702 that is defined by an outer tank wall 704 that includes a proximal end 706 and a distal end 708. As such, the tank portion 702 may be characterized in that the tank wall 704 is a sidewall that is continuous around the tank, and the distal end 708 defines a bottom wall. The tank portion 702 is also configured to contain a liquid composition 724 configured for vaporization (e.g., an e-liquid or aerosol precursor composition, as described above). The cartridge 700 also includes a mouthpiece portion 710 that is defined by an outer mouthpiece wall 712 that includes a distal end 716 and a proximal end 714 with an exit portal 715 defined therein. In the depicted implementation, the cartridge 700 also includes a collar portion 760 that is positioned between the mouthpiece portion 710 and the tank portion 702. In the depicted implementation, the collar portion 760 is configured to be joined to the mouthpiece portion 710 and the tank portion 702 via a press or snap-fit connection; however, in other implementations, other attachment methods are possible (e.g., via adhesives, heat staking/welding, ultrasonic welding, etc.) or any combination thereof.

In some implementations, the outer tank wall 704 may be configured to be one of at least partially transparent or translucent so that the liquid composition 724 contained therein is visible externally. As such, in some implementations, the entire outer tank wall 704 may be transparent or translucent. Alternatively, in some implementations, only a single side, or a portion (or portions) of one or more sides, of the outer tank wall 704 may be transparent or translucent while the remaining portions of the outer tank wall may be substantially opaque. In some embodiments, the outer tank wall 704 or a portion thereof may be substantially opaque, and a strip extending from the proximal end 706 of the tank 702 to the distal end 708 of the tank may be transparent or translucent. In further implementations, the outer tank wall 704 may be colored. In some implementations, the color can be configured so that the liquid composition 724 within the tank 702 is still visible, such by using a transparent or translucent outer tank wall. In other implementations, the tank wall can be configured so that the outer tank wall 704 has a substantially opaque color.

In the depicted implementation, one or more of the mouthpiece portion 710, the collar portion 760, and the tank portion 702 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in FIG. 6, the cartridge 700 further includes a heating member 720 and a pair of electrical contacts 725A, 725B that are configured to electrically connect the heating member 720 with the battery and/or control component of a control device. In the depicted implementation, the contacts 725A, 725B are located on opposite sides of the cartridge 700 and are configured to be attached to the collar portion 760. Although in the depicted implementation the contacts 725A, 725B are configured to be attached to the collar portion 760 via a press-fit or snap fit attachment, in other implementations other forms of attachment are possible, including, for example, via an adhesive or via an insert molding process. In the depicted implementation, the electrical contacts 725A, 725B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 720 may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 720 may be integrated with the first liquid transport element 721. Other types of heating members may also be utilized, as noted above.

The cartridge 700 of the depicted implementation also includes a pair of liquid transport elements. In particular, the cartridge 700 includes a first liquid transport element 721, and a second liquid transport element 722. In the depicted implementation, at least a portion of the first liquid transport element 721 is configured to be located proximate the heating member 720. In addition, the second liquid transport element 722 of the depicted implementation is configured to extend between the first liquid transport element 721 and the liquid composition 724 contained within the tank 702 such that the second liquid transport element 722 is configured to transport liquid to the first liquid transport element 721. In the depicted implementation, the second liquid transport element 722 has a T-shape with a transverse portion 727 that intersects a longitudinal portion 729. Although other configurations are possible, in the depicted implementation, the length of the transverse portion 727 is longer than the length of the longitudinal portion 729.

As shown in FIGS. 7A and 7B, the first liquid transport element 721, the second liquid transport element 722, and the heating member 720 are located in the collar portion 760 of the cartridge 700. When installed in the cartridge, the heating member 720 of the depicted implementation has a curved or bowed shape. In addition, when installed in the cartridge the first liquid transport element 721 of the depicted implementation also has curved or bowed shape. In particular, the heating member 720 of the depicted implementation comprises a flat heating element that, when installed in the cartridge 700, has a curved or bowed shape corresponding to (e.g., similar or approximately the same as) the curved shape of the top surface of the first liquid transport element 721 (or, in some implementations, vice versa). In such a manner, the heating member 720 in the installed position contacts a top surface of the first liquid transport element 721. In the depicted implementation, the curved form of the flat heating member 720 may provide a large ratio of cross-sectional flow area to flow path length through the first liquid transport element 721. When installed, the curvature of the heating member 720 may provide a compressive force against the first liquid transport element 721. The installed curvature of the heating member 720 may also bias deflection of the heating member 720 that may occur with thermal expansion towards the first liquid transport element 721, thus helping to maintain thermal contact between the heating member 720 and the first liquid transport element 721. Furthermore, when installed in the cartridge 700 the transverse portion 727 of the second liquid transport element 722 also has a curved or bowed shape corresponding to (e.g., similar or approximately the same as) the curvature of the bottom surface of the first liquid transport element 721. In such a manner, a top surface of the transverse portion 727 of the second liquid transport element 722 contacts a bottom surface of the first liquid transport element 721. As such, one or more of these features may provide increased performance with respect to delivery of the liquid composition to the first liquid transport element 721.

In various implementations, one or both of the first liquid transport element 721 and the second liquid transport element 722 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 721 comprises a fibrous material and the second liquid transport element 722 comprises a semi-rigid material. In the depicted implementation, the second liquid transport element 722 is configured to be press-fit into the collar portion 760, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, the cartridge 700 further includes a hood feature 762 (which in the depicted implementation is a curved hood feature), a portion of which is configured to be located above the heating member 720 and within the collar portion 760. In the depicted implementation, the hood feature 762 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, the hood feature may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. The hood feature 762 of the depicted implementation has curvature that opposes the curvature of the heating member 720. For example, in the depicted implementation the heating member 720 has a concave curvature (with respect to the mouthpiece end of the longitudinal axis shown in FIG. 3A), whereas the hood feature 762 has a convex curvature. In the depicted implementation, the heating member 720 and the hood feature 762 define at least a portion of a vaporization chamber 740. As noted above, aerosol is generated in the vaporization chamber 740 when the heating member 720 heats at least a portion of the liquid composition contained in the first liquid transport element 721. In the depicted implementation, the hood feature 762 is configured to direct aerosol, collect condensation, and/or shield against liquid and high temperatures from directly exiting the cartridge 700. As such, when a user draws on the aerosol delivery device, aerosol from the vaporization chamber 740 may be delivered to the user via the exit portal 715 of the mouthpiece portion 710.

FIGS. 8 and 9 illustrate a cartridge in accordance with another implementation of the present disclosure. In particular, FIG. 8 illustrates an exploded perspective view of a cartridge 900 according to an example implementation of the present disclosure, and FIG. 9 illustrates a partial cross-section view of the cartridge 900. In various implementations, a portion of the cartridge 900 is configured to be removably coupled with a cartridge receiving chamber of a corresponding control device. In many aspects, the cartridge 900 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 900 of the depicted implementation includes a tank portion 902 that is defined by an outer tank wall 904 that includes a proximal end 906 and a distal end 908. As such, the tank portion 902 may be characterized in that the tank wall 904 is a sidewall that is continuous around the tank, and the distal end 908 defines a bottom wall. The tank portion 902 is also configured to contain a liquid composition 924 configured for vaporization (e.g., an e-liquid or aerosol precursor composition, as described above). The cartridge 900 also includes a mouthpiece portion 910 that is defined by an outer mouthpiece wall 912 that includes a distal end 916 and a proximal end 914 with an exit portal 915 defined therein. In the depicted implementation, the cartridge 900 also includes a collar portion 960 that is positioned between the mouthpiece portion 910 and the tank portion 902. In the depicted implementation, the collar portion 960 is configured to be joined to the mouthpiece portion 910 and the tank portion 902 via a press or snap-fit connection; however, in other implementations, other attachment methods are possible (e.g., via adhesives, heat staking/welding, ultrasonic welding, etc.) or any combination thereof.

In some implementations, the outer tank wall 904 may be configured to be one of at least partially transparent or translucent so that the liquid composition 924 contained therein is visible externally. As such, in some implementations, the entire outer tank wall 904 may be transparent or translucent. Alternatively, in some implementations, only a single side, or a portion (or portions) of one or more sides, of the outer tank wall 904 may be transparent or translucent while the remaining portions of the outer tank wall may be substantially opaque. In some embodiments, the outer tank wall 904 or a portion thereof may be substantially opaque, and a strip extending from the proximal end 906 of the tank 902 to the distal end 908 of the tank may be transparent or translucent. In further implementations, the outer tank wall 904 may be colored. In some implementations, the color can be configured so that the liquid composition 924 within the tank 902 is still visible, such by using a transparent or translucent outer tank wall. In other implementations, the tank wall can be configured so that the outer tank wall 904 has a substantially opaque color.

In the depicted implementation, one or more of the mouthpiece portion 910, the collar portion 960, and the tank portion 902 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figures, the cartridge 900 further includes a heating member 920 and a pair of electrical contacts 925A, 925B that are configured to electrically connect the heating member 920 with the battery and/or control component of a control device. In the depicted implementation, the contacts 925A, 925B are located on opposite sides of the cartridge 900 and are configured to be attached to the collar portion 960. Although in the depicted implementation the contacts 925A, 925B are configured to be attached to the collar portion 960 via a press-fit or snap fit attachment, in other implementations other forms of attachment are possible, including, for example, via an adhesive or via an insert molding process. In the depicted implementation, the electrical contacts 925A, 925B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 920 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heater 920 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 920 may be integrated with the first liquid transport element 921. Other types of heating members (e.g., laser diodes, microheaters, etc.) may also be utilized, as noted above.

The cartridge 900 of the depicted implementation also includes a pair of liquid transport elements. In particular, the cartridge 900 includes a first liquid transport element 921, and a second liquid transport element 922. In the depicted implementation, a portion of the heating member 920 is configured to be wrapped around a portion of the first liquid transport element 921. In the depicted implementation, the second liquid transport element 922 is configured to extend between the first liquid transport element 921 and the liquid composition 924 contained within the tank 902 such that the second liquid transport element 922 is configured to transport liquid to the first liquid transport element 921. In the depicted implementation, the second liquid transport element 922 has a T-shape with a transverse portion 927 that intersects a longitudinal portion 929. Although other configurations are possible, in the depicted implementation, the length of the longitudinal portion 929 is longer than the length of the transverse portion 927. The second liquid transport element 922 of the depicted implementation also serves to seal the collar portion 960 from the liquid composition 924.

In the depicted implementation, the cartridge 900 also includes an upper frame portion 931 that may include various features configured to retain the heating member 920 and at least a portion of the first liquid transport element 921. In the depicted implementation, the upper frame portion 931 is constructed of a thermoplastic elastomer (TPE) or a silicone material, although other materials are possible. The upper frame portion 931 of the depicted implementation is also configured to facilitate connection (such as, for example, by pressing together) the ends of the heating member 920 to the respective electrical contacts 925A, 925B. In the depicted implementation, at least a portion of one or more of the upper frame portion 931, the heating member 920, the first liquid transport element 921, and the electrical contacts 925A, 925B are contained within the collar portion 960. When installed in the cartridge, the first liquid transport element 921 has a U-shape comprising a lateral central portion 933 and two longitudinal leg portions 935A, 935B that intersect and extend downward from the central portion 933. Although other configurations are possible, in the depicted implementation, the length of the lateral central portion 933 is longer than the length of the longitudinal leg portions 935A, 935B. In the depicted implementation, respective ends of the leg portions 935A, 935B contact the top surface of the lateral portion 927 of the second liquid transport element 922. In such a manner, the second liquid transport element 922 may facilitate delivery of liquid composition 924 to the first liquid transport element 921.

In various implementations, one or both of the first liquid transport element 921 and the second liquid transport element 922 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 921 comprises a fibrous material and the second liquid transport element 922 comprises a semi-rigid material. In the depicted implementation, the second liquid transport element 922 is configured to be press-fit into the collar portion 960, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 920 is wrapped around the lateral central portion 933 of the first liquid transport element 921. In the depicted implementation, a vaporization chamber 940 is located in an area around the first liquid transport element 921 upon which the heating member 920 is wrapped, and is defined, at least in part, by the upper frame portion 931 and the second liquid transport element 922. As noted above, aerosol is generated in the vaporization chamber 940 when the heating member 920 heats at least a portion of the liquid composition contained in the first liquid transport element 921. As such, when a user draws on the aerosol delivery device, aerosol from the vaporization chamber 940 may be delivered to the user via the exit portal 915 of the mouthpiece portion 910.

FIGS. 10 and 11 illustrate a cartridge in accordance with another implementation of the present disclosure. In particular, FIG. 10 illustrates an exploded perspective view of a cartridge 1100 according to an example implementation of the present disclosure, and FIG. 11 illustrates a partial cross-section view of the cartridge 1100. In various implementations, a portion of the cartridge 1100 is configured to be removably coupled with a cartridge receiving chamber of a corresponding control device. In many aspects, the cartridge 1100 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 1100 of the depicted implementation includes a tank portion 1102 that is defined by an outer tank wall 1104 and that includes a proximal end 1106 and a distal end 1108. As such, the tank portion 1102 may be characterized in that the tank wall 1104 is a sidewall that is continuous around the tank, and the distal end 1108 defines a bottom wall. The tank portion 1102 is also configured to contain a liquid composition 1124 configured for vaporization (e.g., an e-liquid or aerosol precursor composition, as described above). The cartridge 1100 also includes a mouthpiece portion 1110 that is defined by an outer mouthpiece wall 1112 and that includes a distal end 1116 and a proximal end 1114 with an exit portal 1115 defined therein. In the depicted implementation, the cartridge 1100 also includes a collar portion 1160 that is positioned between the mouthpiece portion 1110 and the tank portion 1102. In the depicted implementation, the collar portion 1160 is configured to be joined to the mouthpiece portion 1110 and the tank portion 1102 via a press or snap-fit connection; however, in other implementations, other attachment methods are possible (e.g., via adhesives, heat staking/welding, ultrasonic welding, etc.) or any combination thereof.

In some implementations, the outer tank wall 1104 may be configured to be one of at least partially transparent or translucent so that the liquid composition 1124 contained therein is visible externally. As such, in some implementations, the entire outer tank wall 1104 may be transparent or translucent. Alternatively, in some implementations, only a single side, or a portion (or portions) of one or more sides, of the outer tank wall 1104 may be transparent or translucent while the remaining portions of the outer tank wall may be substantially opaque. In some embodiments, the outer tank wall 1104 or a portion thereof may be substantially opaque, and a strip extending from the proximal end 1106 of the tank 1102 to the distal end 1108 of the tank may be transparent or translucent. In further implementations, the outer tank wall 1104 may be colored. In some implementations, the color can be configured so that the liquid composition 1124 within the tank 1102 is still visible, such by using a transparent or translucent outer tank wall. In other implementations, the tank wall can be configured so that the outer tank wall 1104 has a substantially opaque color.

In the depicted implementation, one or more of the mouthpiece portion 1110, the collar portion 1160, and the tank portion 1102 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figures, the cartridge 1100 further includes a heating member 1120 and a pair of electrical contacts 1125A, 1125B that are configured to electrically connect the heating member 1120 with the battery and/or control component of a control device. In the depicted implementation, the contacts 1125A, 1125B are located on opposite sides of the cartridge 1100 and are configured to be attached to the collar portion 1160. Although in the depicted implementation the contacts 1125A, 1125B are configured to be attached to the collar portion 1160 via a press-fit or snap fit attachment, in other implementations other forms of attachment are possible, including, for example, via an adhesive or via an insert molding process. In the depicted implementation, the electrical contacts 1125A, 1125B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 1120 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heater 1120 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 1120 may be integrated with the first liquid transport element 1121. Other types of heating members (e.g., laser diodes, microheaters, etc.) may also be utilized, as noted above.

The cartridge 1100 of the depicted implementation also includes a pair of liquid transport elements. In particular, the cartridge 1100 includes a first liquid transport element 1121, and a second liquid transport element 1122. In the depicted implementation, a portion of the heating member 1120 is configured to be wrapped around a portion of the first liquid transport element 1121. In the depicted implementation, the second liquid transport element 1122 is configured to be disposed below the first liquid transport element 1121 and to wrap around at least a portion of the first liquid transport element 1121. In the depicted implementation, the second liquid transport element 1122 has a relatively flat shape.

In the depicted implementation, the cartridge 1100 also includes an upper frame portion 1131 that includes various features configured to retain the heating member 1120 and at least a portion of the first liquid transport element 1121. In the depicted implementation, the upper frame portion 1131 is constructed of a thermoplastic elastomer (TPE) or a silicone material, although other materials are possible. In the depicted implementation, at least a portion of one or more of the upper frame portion 1131, the heating member 1120, the first liquid transport element 1121, the second liquid transport element 1122, and the electrical contacts 1125A, 1125B are contained within the collar portion 1160. When installed in the cartridge, the first liquid transport element 1121 has a U-shape comprising a lateral central portion 1133 and two longitudinal leg portions 1135A, 1135B that extend downward from the central portion 1133. Although other configurations are possible, in the depicted implementation, the length of the longitudinal leg portions are longer than the length of the transverse central portion. In the depicted implementation, respective ends of the leg portions 1135A, 1135B extend downward into the tank portion 1102 such that they extend into the liquid composition 1124. Although other configurations are possible, in the depicted implementation the ends of the longitudinal legs 1135A, 1135B extend to (e.g., proximate) the bottom wall of the tank portion 1102.

In various implementations, one or both of the first liquid transport element 1121 and the second liquid transport element 1122 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 1121 comprises a fibrous material and the second liquid transport element 1122 comprises a semi-rigid material. In the depicted implementation, the second liquid transport element 1122 is configured to be press-fit into the collar portion 1160, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 1120 is wrapped around the lateral central portion 1133 of the first liquid transport element 1121. In the depicted implementation, a vaporization chamber 1140 is located in an area around the first liquid transport element 1121 upon which the heating member 1120 is wrapped, and is defined, at least in part, by the upper frame portion 1131 and the second liquid transport element 1122. As noted above, aerosol is generated in the vaporization chamber 1140 when the heating member 1120 heats at least a portion of the liquid composition contained in the first liquid transport element 1121. As such, when a user draws on the aerosol delivery device, aerosol from the vaporization chamber 1140 may be delivered to the user via the exit portal 1115 of the mouthpiece portion 1110.

FIGS. 12 and 13 illustrate a cartridge in accordance with another implementation of the present disclosure. In particular, FIG. 12 illustrates an exploded perspective view of a cartridge 1300 according to an example implementation of the present disclosure, and FIG. 13 illustrates a partial cross-section view of the cartridge 1300. In various implementations, a portion of the cartridge 1300 is configured to be removably coupled with a cartridge receiving chamber of a corresponding control device. In many aspects, the cartridge 1300 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 1300 of the depicted implementation includes a tank portion 1302 that is defined by an outer tank wall 1304 that includes a proximal end 1306 and a distal end 1308. As such, the tank portion 1302 may be characterized in that the tank wall 1304 is a sidewall that is continuous around the tank, and the distal end 1308 defines a bottom wall. The tank portion 1302 is also configured to contain a liquid composition 1324 configured for vaporization (e.g., an e-liquid or aerosol precursor composition, as described above). The cartridge 1300 also includes a mouthpiece portion 1310 that is defined by an outer mouthpiece wall 1312 that includes a distal end 1316 and a proximal end 1314 with one or more exit portals 1315 defined therein. In the depicted implementation, the cartridge 1300 also includes a collar portion 1360 that is positioned between the mouthpiece portion 1310 and the tank portion 1302. In the depicted implementation, the collar portion 1360 is configured to be joined to the mouthpiece portion 1310 and the tank portion 1302 via a press or snap-fit connection; however, in other implementations, other attachment methods are possible (e.g., via adhesives, heat staking/welding, ultrasonic welding, etc.) or any combination thereof.

In some implementations, the outer tank wall 1304 may be configured to be one of at least partially transparent or translucent so that the liquid composition 1324 contained therein is visible externally. As such, in some implementations, the entire outer tank wall 1304 may be transparent or translucent. Alternatively, in some implementations, only a single side, or a portion (or portions) of one or more sides, of the outer tank wall 1304 may be transparent or translucent while the remaining portions of the outer tank wall may be substantially opaque. In some embodiments, the outer tank wall 1304 or a portion thereof may be substantially opaque, and a strip extending from the proximal end 1306 of the tank 1302 to the distal end 1308 of the tank may be transparent or translucent. In further implementations, the outer tank wall 1304 may be colored. In some implementations, the color can be configured so that the liquid composition 1324 within the tank 1302 is still visible, such by using a transparent or translucent outer tank wall. In other implementations, the tank wall can be configured so that the outer tank wall 1304 has a substantially opaque color.

In the depicted implementation, one or more of the mouthpiece portion 1310, the collar portion 1360, and the tank portion 1302 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figures, the cartridge 1300 further includes a heating member 1320 and a pair of electrical contacts 1325A, 1325B that are configured to electrically connect the heating member 1320 with the battery and/or control component of a control device. In the depicted implementation, the contacts 1325A, 1325B are located on opposite sides of the cartridge 1300 and are configured to be attached to the collar portion 1360. Although in the depicted implementation the contacts 1325A, 1325B are configured to be attached to the collar portion 1360 via a press-fit or snap fit attachment, in other implementations other forms of attachment are possible, including, for example, via an adhesive or via an insert molding process. In the depicted implementation, the electrical contacts 1325A, 1325B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 1320 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heater 1320 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 1320 may be integrated with the first liquid transport element 1321. Other types of heating members (e.g., laser diodes, microheaters, etc.) may also be utilized, as noted above.

The cartridge 1300 of the depicted implementation also includes a pair of liquid transport elements. In particular, the cartridge 1300 includes a first liquid transport element 1321, and a second liquid transport element 1322. In the depicted implementation, a portion of the heating member 1320 is configured to be wrapped around a portion of the first liquid transport element 1321. In the depicted implementation, the second liquid transport element 1322 is configured to extend between the first liquid transport element 1321 and the liquid composition 1324 contained within the tank 1302 such that the second liquid transport element 1322 is configured to transport liquid to the first liquid transport element 1321. In the depicted implementation, the first and second liquid transport elements 1321, 1322 have substantially solid (e.g., non-hollow) cylindrical shapes and are substantially aligned with the longitudinal axis of the cartridge. Although other configurations are possible, in the depicted implementation, the outer diameter of the second liquid transport element 1322 is larger than the outer diameter of the first liquid transport element 1321, and the length of the second liquid transport element is longer than the length of the first liquid transport element 1321. The second liquid transport element 1322 of the depicted implementation also serves to seal the collar portion 1360 from the liquid composition 1324.

In the depicted implementation, the cartridge 1300 also includes an upper frame portion 1331 that may include various features configured to retain the heating member 1320 and at least a portion of the first liquid transport element 1321. In the depicted implementation, the upper frame portion 1331 is constructed of a thermoplastic elastomer (TPE) or a silicone material, although other materials are possible. The upper frame portion 1331 of the depicted implementation is also configured to facilitate connection (such as, for example, by pressing together) the ends of the heating member 1320 to the respective electrical contacts 1325A, 1325B. In the depicted implementation, at least a portion of one or more of the upper frame portion 1331, the heating member 1320, the first liquid transport element 1321, and the electrical contacts 1325A, 1325B are contained within the collar portion 1360. In the depicted implementation, the distal end of the first liquid transport element 1321 contacts the proximal end of the second liquid transport element 1322. In such a manner, as noted above, the second liquid transport element 1322 may facilitate delivery of liquid composition 1324 to the first liquid transport element 1321.

In various implementations, one or both of the first liquid transport element 1321 and the second liquid transport element 1322 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 1321 comprises a ceramic material and the second liquid transport element 1322 comprises a semi-rigid material. In the depicted implementation, the first liquid transport element 1321 is configured to be trapped between the mouthpiece portion 1310 and the collar portion 1360. In the depicted implementation, the first liquid transport element 1321 and the second liquid transport element 1322 are configured to be press-fit into the collar portion 1360, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 1320 is wrapped around a portion of the first liquid transport element 1321. In the depicted implementation, a vaporization chamber 1340 is located in an area around the first liquid transport element 1321 upon which the heating member 1320 is wrapped, and is defined, at least in part, by the upper frame member 1331. As noted above, aerosol is generated in the vaporization chamber 1340 when the heating member 1320 heats at least a portion of the liquid composition contained in the first liquid transport element 1321. As such, when a user draws on the aerosol delivery device, aerosol from the vaporization chamber 1340 may be delivered to the user via the exit portals 1315 of the mouthpiece portion 1310.

FIG. 14 illustrates a cartridge in accordance with another implementation of the present disclosure. In particular, FIG. 14 illustrates a partial cross-section view of a cartridge 1500 according to an example implementation of the present disclosure. In various implementations, a portion of the cartridge 1500 is configured to be removably coupled with a cartridge receiving chamber of a corresponding control device. In many aspects, the cartridge 1500 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figure, the cartridge 1500 of the depicted implementation includes a tank portion 1502 that is defined by an outer tank wall 1504 that includes a proximal end 1506 and a distal end 1508. As such, the tank portion 1502 may be characterized in that the tank wall 1504 is a sidewall that is continuous around the tank, and the distal end 1508 defines a bottom wall. The tank portion 1502 is also configured to contain a liquid composition 1524 configured for vaporization (e.g., an e-liquid or aerosol precursor composition, as described above). The cartridge 1500 also includes a mouthpiece portion 1510 that is defined by an outer mouthpiece wall 1512 that includes a distal end 1516 and a proximal end 1514 with one or more exit portals 1515 defined therein. In the depicted implementation, the cartridge 1500 also includes a collar portion 1560 that is positioned between the mouthpiece portion 1510 and the tank portion 1502. In the depicted implementation, the collar portion 1560 is configured to be joined to the mouthpiece portion 1510 and the tank portion 1502 via a press or snap-fit connection; however, in other implementations, other attachment methods are possible (e.g., via adhesives, heat staking/welding, ultrasonic welding, etc.) or any combination thereof.

In some implementations, the outer tank wall 1504 may be configured to be one of at least partially transparent or translucent so that the liquid composition 1524 contained therein is visible externally. As such, in some implementations, the entire outer tank wall 1504 may be transparent or translucent. Alternatively, in some implementations, only a single side, or a portion (or portions) of one or more sides, of the outer tank wall 1504 may be transparent or translucent while the remaining portions of the outer tank wall may be substantially opaque. In some embodiments, the outer tank wall 1504 or a portion thereof may be substantially opaque, and a strip extending from the proximal end 1506 of the tank 1502 to the distal end 1508 of the tank may be transparent or translucent. In further implementations, the outer tank wall 1504 may be colored. In some implementations, the color can be configured so that the liquid composition 1524 within the tank 1502 is still visible, such by using a transparent or translucent outer tank wall. In other implementations, the tank wall can be configured so that the outer tank wall 1504 has a substantially opaque color.

In the depicted implementation, one or more of the mouthpiece portion 1510, the collar portion 1560, and the tank portion 1502 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figure, the cartridge 1500 further includes a heating member 1520 and a pair of electrical contacts 1525A, 1525B that are configured to electrically connect the heating member 1520 with the battery and/or control component of a control device. In the depicted implementation, the contacts 1525A, 1525B are located on opposite sides of the cartridge 1500 and are configured to be attached to the collar portion 1560. Although in the depicted implementation the contacts 1525A, 1525B are configured to be attached to the collar portion 1560 via a press-fit or snap fit attachment, in other implementations other forms of attachment are possible, including, for example, via an adhesive or via an insert molding process. In the depicted implementation, the electrical contacts 1525A, 1525B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 1520 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member 1520 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 1520 may be integrated with the first liquid transport element 1521. Other types of heating members (e.g., laser diodes, microheaters, etc.) may also be utilized, as noted above.

The cartridge 1500 of the depicted implementation also includes a pair of liquid transport elements. In particular, the cartridge 1500 includes a first liquid transport element 1521, and a second liquid transport element 1522. In the depicted implementation, a portion of the heating member 1520 is configured to be wrapped around a portion of the first liquid transport element 1521. In the depicted implementation, the second liquid transport element 1522 has a substantially hollow cylindrical shape and is substantially aligned with the longitudinal axis of the cartridge. In the depicted implementation, the first liquid transport element 1521 has a substantially solid (e.g., non-hollow) cylindrical shape and is also substantially aligned with the longitudinal axis of the cartridge. In the depicted implementation, the first liquid transport element 1521 extends thorough the second liquid transport element 1522 such that both the first liquid transport element 1521 and the second liquid transport element 1522 extend to the bottom of the tank portion 1502. In the depicted implementation, the second liquid transport element 1522 is configured to surround at least a portion of the first liquid transport element 1521 and extends between the collar portion 1560 and the liquid composition 1524 contained within the tank 1502 such that the second liquid transport element 1522 is configured to transport liquid to the first liquid transport element 1521. In the depicted implementation, the outer diameter of the second liquid transport element 1522 is larger than the outer diameter of the first liquid transport element 1521 and the length of the first liquid transport 1521 element is longer than the length of the second liquid transport element 1522. The second liquid transport element 1522 of the depicted implementation also serves to seal the collar portion 1560 from the liquid composition 1524.

In the depicted implementation, the cartridge 1500 also includes an upper frame portion 1531 that may include various features configured to retain the heating member 1520 and at least a portion of the first liquid transport element 1521. In the depicted implementation, the upper frame portion 1531 is constructed of a thermoplastic elastomer (TPE) or a silicone material, although other materials are possible. The upper frame portion 1531 of the depicted implementation is also configured to facilitate connection (such as, for example, by pressing together) the ends of the heating member 1520 to the respective electrical contacts 1525A, 1525B. In the depicted implementation, at least a portion of one or more of the upper frame portion 1531, the heating member 1520, the first liquid transport element 1521, and the electrical contacts 1525A, 1525B are contained within the collar portion 1560.

In various implementations, one or both of the first liquid transport element 1521 and the second liquid transport element 1522 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 1521 comprises a ceramic material and the second liquid transport element 1522 comprises a semi-rigid material. In the depicted implementation, the first liquid transport element 1521 is configured to be trapped between the mouthpiece portion 1510 and the collar portion 1560. In the depicted implementation, the first liquid transport element 1521 and the second liquid transport element 1522 are configured to be press-fit into the collar portion 1560, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 1520 is wrapped around a portion of the first liquid transport element 1521. In the depicted implementation, a vaporization chamber 1540 is located in an area around the first liquid transport element 1521 upon which the heating member 1520 is wrapped, and is defined, at least in part, by the upper frame portion 1531. As noted above, aerosol is generated in the vaporization chamber 1540 when the heating member 1520 heats at least a portion of the liquid composition contained in the first liquid transport element 1521. As such, when a user draws on the aerosol delivery device, aerosol from the vaporization chamber 1540 may be delivered to the user via the exit portals 1515 of the mouthpiece portion 1510.

FIGS. 15 and 16 illustrate a cartridge in accordance with another implementation of the present disclosure. In particular, FIG. 15 illustrates an exploded perspective view of a cartridge 1700 according to an example implementation of the present disclosure, and FIG. 16 illustrates a partial cross-section view of the cartridge 1700. In various implementations, a portion of the cartridge 1700 is configured to be removably coupled with a cartridge receiving chamber of a corresponding control device. In many aspects, the cartridge 1700 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 1700 of the depicted implementation includes a tank portion 1702 that is defined by an outer tank wall 1704 that includes a proximal end 1706 and a distal end 1708. As such, the tank portion 1702 may be characterized in that the tank wall 1704 is a sidewall that is continuous around the tank, and the distal end 1708 defines a bottom wall. The tank portion 1702 is also configured to contain a liquid composition 1724 configured for vaporization (e.g., an e-liquid or aerosol precursor composition, as described above). The cartridge 1700 also includes a mouthpiece portion 1710 that is defined by an outer mouthpiece wall 1712 that includes a distal end 1716 and a proximal end 1714 with an exit portal 1715 defined therein. In the depicted implementation, the cartridge 1700 also includes a collar portion 1760 that is positioned between the mouthpiece portion 1710 and the tank portion 1702. In the depicted implementation, the collar portion 1760 is configured to be joined to the mouthpiece portion 1710 and the tank portion 1702 via a press or snap-fit connection; however, in other implementations, other attachment methods are possible (e.g., via adhesives, heat staking/welding, ultrasonic welding, etc.) or any combination thereof.

In some implementations, the outer tank wall 1704 may be configured to be one of at least partially transparent or translucent so that the liquid composition 1724 contained therein is visible externally. As such, in some implementations, the entire outer tank wall 1704 may be transparent or translucent. Alternatively, in some implementations, only a single side, or a portion (or portions) of one or more sides, of the outer tank wall 1704 may be transparent or translucent while the remaining portions of the outer tank wall may be substantially opaque. In some embodiments, the outer tank wall 1704 or a portion thereof may be substantially opaque, and a strip extending from the proximal end 1706 of the tank 1702 to the distal end 1708 of the tank may be transparent or translucent. In further implementations, the outer tank wall 1704 may be colored. In some implementations, the color can be configured so that the liquid composition 1724 within the tank 1702 is still visible, such by using a transparent or translucent outer tank wall. In other implementations, the tank wall can be configured so that the outer tank wall 1704 has a substantially opaque color.

In the depicted implementation, one or more of the mouthpiece portion 1710, the collar portion 1760, and the tank portion 1702 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figures, the cartridge 1700 further includes a heating member 1720 and a pair of electrical contacts 1725A, 1725B that are configured to electrically connect the heating member 1720 with the battery and/or control component of a control device. In the depicted implementation, the contacts 1725A, 1725B are located on opposite sides of the cartridge 1700 and are configured to be attached to the collar portion 1760. Although in the depicted implementation the contacts 1725A, 1725B are configured to be attached to the collar portion 1760 via a press-fit or snap fit attachment, in other implementations other forms of attachment are possible, including, for example, via an adhesive or via an insert molding process. In the depicted implementation, the electrical contacts 1725A, 1725B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 1720 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member 1720 may be formed from conductive inks, boron doped silica, and/or ceramics (e.g., positive or negative temperature coefficient ceramics). Other types of heating members (e.g., laser diodes, microheaters, etc.) may also be utilized, as noted above.

The cartridge 1700 of the depicted implementation also includes a pair of liquid transport elements. In particular, the cartridge 1700 includes a first liquid transport element 1721, and a second liquid transport element 1722. In the depicted implementation, a portion of the heating member 1720 is configured to be embedded within at least a portion of the first liquid transport element 1721. In the depicted implementation, the second liquid transport element 1722 is configured to extend between the first liquid transport element 1721 and the liquid composition 1724 contained within the tank 1702 such that the second liquid transport element 1722 is configured to transport liquid to the first liquid transport element 1721. In the depicted implementation, the first liquid transport element has a cylindrical shape and is substantially aligned with the longitudinal axis of the cartridge. In the depicted implementation, the second liquid transport element 1722 has a substantially solid cylindrical shape and is also substantially aligned with the longitudinal axis of the cartridge. Although other configurations are possible, in the depicted implementation, the outer diameter of the second liquid transport element 1722 is larger than the outer diameter of the first liquid transport element 1721 and the length of the second liquid transport element 1722 is longer than the length of the first liquid transport element 1721. The second liquid transport element 1722 of the depicted implementation also serves to seal the collar portion 1760 from the liquid composition 1724.

In the depicted implementation, the cartridge 1700 also includes an upper frame portion 1731 that may include various features configured to retain the heating member 1720 and at least a portion of the first liquid transport element 1721. In the depicted implementation, the upper frame portion 1731 is constructed of a thermoplastic elastomer (TPE) or a silicone material, although other materials are possible. The upper frame portion 1731 of the depicted implementation is also configured to facilitate connection (such as, for example, by pressing together) the ends of the heating member 1720 to the respective electrical contacts 1725A, 1725B. In the depicted implementation, at least a portion of one or more of the upper frame portion 1731, the heating member 1720, the first liquid transport element 1721, and the electrical contacts 1725A, 1725B are contained within the collar portion 1760. In the depicted implementation, the distal end of the first liquid transport element 1721 contacts the proximal end of the second liquid transport element 1722. In such a manner, the second liquid transport element 1722 may facilitate delivery of liquid composition 1724 to the first liquid transport element 1721.

In various implementations, one or both of the first liquid transport element 1721 and the second liquid transport element 1722 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 1721 comprises a ceramic material and the second liquid transport element 1722 comprises a semi-rigid material. In the depicted implementation, the first liquid transport element 1721 is configured to be trapped between the mouthpiece portion 1710 and the collar portion 1760. In the depicted implementation, the first liquid transport element 1721 and the second liquid transport element 1722 are configured to be press-fit into the collar portion 1760, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized.

Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 1720 is embedded within at least a portion of the first liquid transport element 1721. In the depicted implementation, a vaporization chamber 1740 is located in an area inside the first liquid transport element 1721 as well as an area around the first liquid transport element 1721 proximate the heating member 1720. The vaporization chamber 1740 may also be defined, at least in part, by the upper frame portion 1731. As noted above, aerosol is generated in the vaporization chamber 1740 when the heating member 1720 heats at least a portion of the liquid composition contained in the first liquid transport element 1721. As such, when a user draws on the aerosol delivery device, aerosol from the vaporization chamber 1740 may be delivered to the user via the exit portal 1715 of the mouthpiece portion 1710.

FIG. 17 illustrates a cartridge in accordance with another implementation of the present disclosure. In particular, FIG. 17 illustrates a partial cross-section view of a cartridge 1900 according to an example implementation of the present disclosure. In various implementations, a portion of the cartridge 1900 is configured to be removably coupled with a cartridge receiving chamber of a corresponding control device. In many aspects, the cartridge 1900 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to FIG. 17, the cartridge 1900 of the depicted implementation includes a tank portion 1902 that is defined by an outer tank wall 1904 that includes a proximal end 1906 and a distal end 1908. As such, the tank portion 1902 may be characterized in that the tank wall 1904 is a sidewall that is continuous around the tank, and the distal end 1908 defines a bottom wall. The tank portion 1902 is also configured to contain a liquid composition 1924 configured for vaporization (e.g., an e-liquid or aerosol precursor composition, as described above). The cartridge 1900 also includes a mouthpiece portion 1910 that is defined by an outer mouthpiece wall 1912 that includes a distal end 1916 and a proximal end 1914 with an exit portal 1915 defined therein. In the depicted implementation, the cartridge 1900 also includes a collar portion 1960 that is positioned between the mouthpiece portion 1910 and the tank portion 1902. In the depicted implementation, the collar portion 1960 is configured to be joined to the mouthpiece portion 1910 and the tank portion 1902 via a press or snap-fit connection; however, in other implementations, other attachment methods are possible (e.g., via adhesives, heat staking/welding, ultrasonic welding, etc.) or any combination thereof.

In some implementations, the outer tank wall 1904 may be configured to be one of at least partially transparent or translucent so that the liquid composition 1924 contained therein is visible externally. As such, in some implementations, the entire outer tank wall 1904 may be transparent or translucent. Alternatively, in some implementations, only a single side, or a portion (or portions) of one or more sides, of the outer tank wall 1904 may be transparent or translucent while the remaining portions of the outer tank wall may be substantially opaque. In some embodiments, the outer tank wall 1904 or a portion thereof may be substantially opaque, and a strip extending from the proximal end 1906 of the tank 1902 to the distal end 1908 of the tank may be transparent or translucent. In further implementations, the outer tank wall 1904 may be colored. In some implementations, the color can be configured so that the liquid composition 1924 within the tank 1902 is still visible, such by using a transparent or translucent outer tank wall. In other implementations, the tank wall can be configured so that the outer tank wall 1904 has a substantially opaque color.

In the depicted implementation, one or more of the mouthpiece portion 1910, the collar portion 1960, and the tank portion 1902 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figure, the cartridge 1900 further includes a heating member 1920 and a pair of electrical contacts 1925A, 1925B that are configured to electrically connect the heating member 1920 with the battery and/or control component of a control device. In the depicted implementation, the contacts 1925A, 1925B are located on opposite sides of the cartridge 1900 and are configured to be attached to the collar portion 1960. Although in the depicted implementation the contacts 1925A, 1925B are configured to be attached to the collar portion 1560 via a press-fit or snap fit attachment, in other implementations other forms of attachment are possible, including, for example, via an adhesive or via an insert molding process. In the depicted implementation, the electrical contacts 1925A, 1925B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 1920 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member 1920 may be formed from conductive inks, boron doped silica, and/or ceramics (e.g., positive or negative temperature coefficient ceramics). Other types of heating members (e.g., laser diodes, microheaters, etc.) may also be utilized, as noted above.

The cartridge 1900 of the depicted implementation also includes a pair of liquid transport elements. In particular, the cartridge 1900 includes a first liquid transport element 1921, and a second liquid transport element 1922. In the depicted implementation, a portion of the heating member 1920 is configured to be embedded within at least a portion of the first liquid transport element 1921. In the depicted implementation, the second liquid transport element 1922 has a substantially hollow cylindrical shape and is substantially aligned with the longitudinal axis of the cartridge. In the depicted implementation, the first liquid transport element 1921 extends thorough the second liquid transport element 1922 such that both the first liquid transport element 1921 and the second liquid transport element 1922 extends to the bottom of the tank portion 1902. In the depicted implementation, the second liquid transport element 1922 is configured to surround at least a portion of the first liquid transport element 1921 and extends between the collar portion 1960 and the liquid composition 1924 contained within the tank 1902 such that the second liquid transport element 1922 is configured to transport liquid to the first liquid transport element 1921. In the depicted implementation, the outer diameter of the second liquid transport element 1922 is larger than the outer diameter of the first liquid transport element 1921 and the length of the first liquid transport 1921 element is longer than the length of the second liquid transport element 1922. The second liquid transport element 1922 of the depicted implementation also serves to seal the collar portion 1960 from the liquid composition 1924.

In the depicted implementation, the cartridge 1900 also includes an upper frame portion 1931 that may include various features configured to retain the heating member 1920 and at least a portion of the first liquid transport element 1921. In the depicted implementation, the upper frame portion 1931 is constructed of a thermoplastic elastomer (TPE) or a silicone material, although other materials are possible. The upper frame portion 1931 of the depicted implementation is also configured to facilitate connection (such as, for example, by pressing together) the ends of the heating member 1920 to the respective electrical contacts 1925A, 1925B. In the depicted implementation, at least a portion of one or more of the upper frame portion 1931, the heating member 1920, the first liquid transport element 1921, and the electrical contacts 1925A, 1925B are contained within the collar portion 1960.

In various implementations, one or both of the first liquid transport element 1921 and the second liquid transport element 1922 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 1921 comprises a ceramic material and the second liquid transport element 1922 comprises a semi-rigid material. In the depicted implementation, the first liquid transport element 1921 is configured to be trapped between the mouthpiece portion 1910 and the collar portion 1960. In the depicted implementation, the first liquid transport element 1921 and the second liquid transport element 1922 are configured to be press-fit into the collar portion 1960, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 1920 is embedded within at least a portion of the first liquid transport element 1921. In the depicted implementation, a vaporization chamber 1940 is located in an area inside the first liquid transport element 1921 as well as an area around the first liquid transport element 1921 proximate the heating member 1920. The vaporization chamber 1740 may also be defined, at least in part, by the upper frame portion 1931. As noted above, aerosol is generated in the vaporization chamber 1940 when the heating member 1920 heats at least a portion of the liquid composition contained in the first liquid transport element 1921. As such, when a user draws on the aerosol delivery device, aerosol from the vaporization chamber 1940 may be delivered to the user via the exit portal 1915 of the mouthpiece portion 1910.

FIGS. 18 and 19 illustrate a cartridge in accordance with another implementation of the present disclosure. In particular, FIG. 18 illustrates an exploded perspective view of a cartridge 2100 according to an example implementation of the present disclosure, and FIG. 19 illustrates a partial cross-section view of the cartridge 2100. In various implementations, a portion of the cartridge 2100 is configured to be removably coupled with a cartridge receiving chamber of a corresponding control device. In many aspects, the cartridge 2100 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 2100 of the depicted implementation includes a tank portion 2102 that is defined by an outer tank wall 2104 that includes a proximal end 2106 and a distal end 2108. As such, the tank portion 2102 may be characterized in that the tank wall 2104 is a sidewall that is continuous around the tank, and the distal end 2108 defines a bottom wall. The tank portion 2102 is also configured to contain a liquid composition 2124 configured for vaporization (e.g., an e-liquid or aerosol precursor composition, as described above). The cartridge 2100 also includes a mouthpiece portion 2110 that is defined by an outer mouthpiece wall 2112 that includes a distal end 2116 and a proximal end 2114 with an exit portal 2115 defined therein. In the depicted implementation, the cartridge 2100 also includes a collar portion 2160, at least a portion of which is positioned between the mouthpiece portion 2110 and the tank portion 2102. In the depicted implementation, the collar portion 2160 is configured to be joined to the mouthpiece portion 2110 and the tank portion 2102 via a press or snap-fit connection; however, in other implementations, other attachment methods are possible (e.g., via adhesives, heat staking/welding, ultrasonic welding, etc.) or any combination thereof.

In some implementations, the outer tank wall 2104 may be configured to be one of at least partially transparent or translucent so that the liquid composition 2124 contained therein is visible externally. As such, in some implementations, the entire outer tank wall 2104 may be transparent or translucent. Alternatively, in some implementations, only a single side, or a portion (or portions) of one or more sides, of the outer tank wall 2104 may be transparent or translucent while the remaining portions of the outer tank wall may be substantially opaque. In some embodiments, the outer tank wall 2104 or a portion thereof may be substantially opaque, and a strip extending from the proximal end 2106 of the tank 2102 to the distal end 2108 of the tank may be transparent or translucent. In further implementations, the outer tank wall 2104 may be colored. In some implementations, the color can be configured so that the liquid composition 2124 within the tank 2102 is still visible, such by using a transparent or translucent outer tank wall. In other implementations, the tank wall can be configured so that the outer tank wall 2104 has a substantially opaque color.

In the depicted implementation, one or more of the mouthpiece portion 2110, the collar portion 2160, and the tank portion 2102 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 2100 further includes a heating member 2120 and a pair of electrical contacts 2125A, 2125B that are configured to electrically connect the heating member 2120 with the battery and/or control component of a control device. In the depicted implementation, the contacts 2125A, 2125B are located on opposite sides of the cartridge 2100 and are configured to be attached to the collar portion 2160. Although in the depicted implementation the contacts 2125A, 2125B are configured to be attached to the collar portion 2160 via a press-fit or snap fit attachment, in other implementations other forms of attachment are possible, including, for example, via an adhesive or via an insert molding process. In the depicted implementation, the heating member 2120 is located proximate the distal end 2108 of the tank portion 2102. As such, the electrical contacts 2125A, 2125B extend downward such that corresponding ends thereof contact the heating member 2120. In various implementations, the heating member 2120 may be retained by the collar portion 2160 via a press-fit or snap fit attachment, although other forms of attachment are possible, including, for example, via an adhesive or via an insert molding process or being trapped by the collar portion 2160 against the bottom of the tank portion 2102 (e.g., being trapped between the collar portion 2160, one or more liquid transport elements, and the bottom of the tank portion 2102). In the depicted implementation, the electrical contacts 2125A, 2125B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 2120 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 2120 may be integrated with the first liquid transport element 2121. Other types of heating members may also be utilized, as noted above.

The cartridge 2100 of the depicted implementation also includes a pair of liquid transport elements. In particular, the cartridge 2100 includes a first liquid transport element 2121, and a second liquid transport element 2122. In the depicted implementation, at least a portion of the first liquid transport element 2121 is configured to be located proximate the heating member 2120. In addition, the second liquid transport element 2122 of the depicted implementation is configured to extend between the first liquid transport element 2121 and the bottom of the tank portion 2102 such that the second liquid transport element 2122 is configured to transport liquid to the first liquid transport element 2121. In the depicted implementation, the first and second liquid transport elements 2121, 2122 have a flat shape, with the first liquid transport element 2121 being disposed below the heating member 2120 and the second liquid transport element 2122 being disposed below the first liquid transport element 2121.

As shown in the figures, the collar portion 2160 of the depicted implementation extends downward such that a portion of the collar portion 2160 is located proximate the distal end 2108 of the tank portion 2102 and is configured to retain the heating member 2120, the first liquid transport element 2121, and at least a portion of the second liquid transport element 2122. In the depicted implementation, the heating member 2120 in the installed position contacts a top surface of the first liquid transport element 2121, and a top surface of the second liquid transport element 2122 contacts a bottom surface of the first liquid transport element 2121. As such, one or more of these features may provide increased performance with respect to delivery of the liquid composition to the first liquid transport element 2121.

In various implementations, one or both of the first liquid transport element 2121 and the second liquid transport element 2122 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, the cartridge 2100 further includes a hood feature 2162, which is configured to be located proximate the distal end 2116 of the mouthpiece portion 2110. In the depicted implementation, the hood feature 2162 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, the hood feature may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. The hood feature 2162 of the depicted implementation has a block shape with a solid top surface and openings defined in the bottom and side surfaces. In the depicted implementation, a vaporization chamber 2140 is located above the heating member 2120, and is defined, at least in part, by the collar portion 2160. The collar portion 2160 of the depicted implementation also defines a vapor channel 2145 that originates proximate the vaporization chamber 2140 and extends upward, leading to the hood feature 2162. As noted above, aerosol is generated in the vaporization chamber 2140 when the heating member 2120 heats at least a portion of the liquid composition contained in the first liquid transport element 2121. In the depicted implementation, the hood feature 2162 is configured to direct aerosol, collect condensation, and/or shield against liquid and high temperatures from directly exiting the cartridge 2100. As such, when a user draws on the aerosol delivery device, aerosol from the vaporization chamber 2140 may travel through the vapor channel 2145, be diverted by the hood feature 2162, and be delivered to the user via the exit portal 2115 of the mouthpiece portion 2110.

FIG. 20 illustrates a cartridge in accordance with another implementation of the present disclosure. In particular, FIG. 20 illustrates a partial cross-section view of a cartridge 2300. In various implementations, a portion of the cartridge 2300 is configured to be removably coupled with a cartridge receiving chamber of a corresponding control device. In many aspects, the cartridge 2300 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 2300 of the depicted implementation includes a tank portion 2302 that is defined by an outer tank wall 2304 that includes a proximal end 2306 and a distal end 2308. As such, the tank portion 2302 may be characterized in that the tank wall 2304 is a sidewall that is continuous around the tank, and the distal end 2308 defines a bottom wall. The tank portion 2302 is also configured to contain a liquid composition 2324 configured for vaporization (e.g., an e-liquid or aerosol precursor composition, as described above). The cartridge 2300 also includes a mouthpiece portion 2310 that is defined by an outer mouthpiece wall 2312 that includes a distal end 2316 and a proximal end 2314 with an exit portal 2315 defined therein. In the depicted implementation, the cartridge 2300 also includes a collar portion 2360, at least a portion of which is positioned between the mouthpiece portion 2310 and the tank portion 2302. In the depicted implementation, the collar portion 2360 is configured to be joined to the mouthpiece portion 2310 and the tank portion 2302 via a press or snap-fit connection; however, in other implementations, other attachment methods are possible (e.g., via adhesives, heat staking/welding, ultrasonic welding, etc.) or any combination thereof.

In some implementations, the outer tank wall 2304 may be configured to be one of at least partially transparent or translucent so that the liquid composition 2324 contained therein is visible externally. As such, in some implementations, the entire outer tank wall 2304 may be transparent or translucent. Alternatively, in some implementations, only a single side, or a portion (or portions) of one or more sides, of the outer tank wall 2304 may be transparent or translucent while the remaining portions of the outer tank wall may be substantially opaque. In some embodiments, the outer tank wall 2304 or a portion thereof may be substantially opaque, and a strip extending from the proximal end 2306 of the tank 2302 to the distal end 2308 of the tank may be transparent or translucent. In further implementations, the outer tank wall 2304 may be colored. In some implementations, the color can be configured so that the liquid composition 2324 within the tank 2302 is still visible, such by using a transparent or translucent outer tank wall. In other implementations, the tank wall can be configured so that the outer tank wall 2304 has a substantially opaque color.

In the depicted implementation, one or more of the mouthpiece portion 2310, the collar portion 2360, and the tank portion 2302 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 2300 further includes a heating member 2320 and a pair of electrical contacts 2325A, 2325B that are configured to electrically connect the heating member 2320 with the battery and/or control component of a control device. In the depicted implementation, the contacts 2325A, 2325B are located on opposite sides of the cartridge 2300 and are configured to be attached to the collar portion 2360. Although in the depicted implementation the contacts 2325A, 2325B are configured to be attached to the collar portion 2360 via a press-fit or snap fit attachment, in other implementations other forms of attachment are possible, including, for example, via an adhesive or via an insert molding process. In the depicted implementation, the heating member 2320 is located proximate the distal end 2308 of the tank portion 2302. As such, the electrical contacts 2325A, 2325B extend downward such that the corresponding ends thereof contact the heating member 2320. In various implementations, the heating member 2320 may be retained by the collar portion 2360 via a press-fit or snap fit attachment, although other forms of attachment are possible, including, for example, via an adhesive or via an insert molding process or being trapped by the collar portion 2360 against the bottom of the tank portion 2302 (e.g., being trapped between the collar portion 2360, one or more liquid transport elements, and the bottom of the tank portion 2302). In the depicted implementation, the electrical contacts 2325A, 2325B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 2320 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 2320 may be integrated with the first liquid transport element 2321. Other types of heating members may also be utilized, as noted above.

The cartridge 2300 of the depicted implementation also includes a pair of liquid transport elements. In particular, the cartridge 2300 includes a first liquid transport element 2321, and a second liquid transport element 2322. In the depicted implementation, at least a portion of the first liquid transport element 2321 is configured to be located proximate the heating member 2320. In addition, the second liquid transport element 2322 of the depicted implementation is configured to extend between the first liquid transport element 2321 and the bottom of the tank portion 2302 such that the second liquid transport element 2322 is configured to transport liquid to the first liquid transport element 2321. In the depicted implementation, the first liquid transport element 2321 has a flat shape, with the first liquid transport element 2321 being disposed below the heating member 2320 and the second liquid transport element 2322 being disposed below the first liquid transport element 2321.

As shown in the figures, the collar portion 2360 of the depicted implementation extends downward such that a portion of the collar portion 2360 is located between the proximal end 2306 and the distal end 2308 of the tank portion 2302. In the depicted implementation, the collar portion 2360 is configured to retain the heating member 2320, the first liquid transport element 2321, and at least a portion of the second liquid transport element 2322. In the depicted implementation, the heating member 2320 is located between the proximal end 2306 and the distal end 2308 of the tank portion 2302, and in particular, in the middle third portion along the length of the tank portion 2302. In the depicted implementation, the heating member 2320 in the installed position contacts a top surface of the first liquid transport element 2321, and a top surface of the second liquid transport element 2322 contacts a bottom surface of the first liquid transport element 2321. As such, one or more of these features may provide increased performance with respect to delivery of the liquid composition to the first liquid transport element 2321.

In various implementations, one or both of the first liquid transport element 2321 and the second liquid transport element 2322 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, the cartridge 2300 further includes a hood feature 2362, which is configured to be located in the bottom of the mouthpiece portion 2310. In the depicted implementation, the hood feature 2362 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, the hood feature may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. The hood feature 2362 of the depicted implementation has a block shape with a solid top surface and openings defined in the bottom and side surfaces. In the depicted implementation, a vaporization chamber 2340 is located above the heating member 2320, and is defined, at least in part, by the collar portion 2360. In the depicted implementation, the collar portion 2360 defines a vapor channel 2345 that originates proximate the vaporization chamber 2340 and extends upward, leading to the hood feature 2362. As noted above, aerosol is generated in the vaporization chamber 2340 when the heating member 2320 heats at least a portion of the liquid composition contained in the first liquid transport element 2321. In the depicted implementation, the hood feature 2362 is configured to direct aerosol, collect condensation, and/or shield against liquid and high temperatures from directly exiting the cartridge 2300. As such, when a user draws on the aerosol delivery device, aerosol from the vaporization chamber 2340 may travel through the vapor channel 2345, be diverted by the hood feature 2362, and be delivered to the user via the exit portal 2315 of the mouthpiece portion 2310.

FIGS. 21 and 22 illustrate a cartridge in accordance with another implementation of the present disclosure. In particular, FIG. 21 illustrates an exploded perspective view of a cartridge 2500 according to an example implementation of the present disclosure, and FIG. 22 illustrates a partial cross-section view of the cartridge 2500. In various implementations, a portion of the cartridge 2500 is configured to be removably coupled with a cartridge receiving chamber of a corresponding control device. In many aspects, the cartridge 2500 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 2500 of the depicted implementation includes a tank portion 2502 that is defined by an outer tank wall 2504 that includes a proximal end 2506 and a distal end 2508. As such, the tank portion 2502 may be characterized in that the tank wall 2504 is a sidewall that is continuous around the tank, and the distal end 2508 defines a bottom wall. The tank portion 2502 is also configured to contain a liquid composition 2524 configured for vaporization (e.g., an e-liquid or aerosol precursor composition, as described above). The cartridge 2500 also includes a mouthpiece portion 2510 that is defined by an outer mouthpiece wall 2512 that includes a distal end 2516 and a proximal end 2514 with an exit portal 2515 defined therein. In the depicted implementation, the cartridge 2500 also includes a collar portion 2560, at least a portion of which is positioned between the mouthpiece portion 2510 and the tank portion 2502. In the depicted implementation, the collar portion 2560 is configured to be joined to the mouthpiece portion 2510 and the tank portion 2502 via a press or snap-fit connection; however, in other implementations, other attachment methods are possible (e.g., via adhesives, heat staking/welding, ultrasonic welding, etc.) or any combination thereof.

In some implementations, the outer tank wall 2504 may be configured to be one of at least partially transparent or translucent so that the liquid composition 2524 contained therein is visible externally. As such, in some implementations, the entire outer tank wall 2504 may be transparent or translucent. Alternatively, in some implementations, only a single side, or a portion (or portions) of one or more sides, of the outer tank wall 2504 may be transparent or translucent while the remaining portions of the outer tank wall may be substantially opaque. In some embodiments, the outer tank wall 2504 or a portion thereof may be substantially opaque, and a strip extending from the proximal end 2506 of the tank 2502 to the distal end 2508 of the tank may be transparent or translucent. In further implementations, the outer tank wall 2504 may be colored. In some implementations, the color can be configured so that the liquid composition 2524 within the tank 2502 is still visible, such by using a transparent or translucent outer tank wall. In other implementations, the tank wall can be configured so that the outer tank wall 2504 has a substantially opaque color.

In the depicted implementation, one or more of the mouthpiece portion 2510, the collar portion 2560, and the tank portion 2502 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 2500 further includes a heating member 2520 and a pair of electrical contacts 2525A, 2525B that are configured to electrically connect the heating member 2520 with the battery and/or control component of a control device. In the depicted implementation, the contacts 2525A, 2525B are located on opposite sides of the cartridge 2500 and are configured to be attached to the collar portion 2560. Although in the depicted implementation the contacts 2525A, 2525B are configured to be attached to the collar portion 2560 via a press-fit or snap fit attachment, in other implementations other forms of attachment are possible, including, for example, via an adhesive or via an insert molding process. In the depicted implementation, the heating member 2520 is located proximate the distal end 2508 of the tank portion 2502. As such, the electrical contacts 2525A, 2525B extend downward such that the corresponding ends thereof contact the heating member 2520. In various implementations, the heating member 2520 may be retained by the collar portion 2560 via a press-fit or snap fit attachment, although other forms of attachment are possible, including, for example, via an adhesive or via an insert molding process or being trapped by the collar portion 2560 against the bottom of the tank portion 2502. In the depicted implementation, the electrical contacts 2525A, 2525B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 2520 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 2520 may be integrated with the liquid transport element 2521. Other types of heating members may also be utilized, as noted above.

The cartridge 2500 of the depicted implementation also includes a liquid transport element 2521. In the depicted implementation, at least a portion of the liquid transport element 2521 is configured to be located proximate the heating member 2520. In the depicted implementation, the liquid transport element 2521 is disposed below the heating member 2520 and extends between the heating member 2520 and the bottom of the tank portion 2502. As shown in the figures, the collar portion 2560 of the depicted implementation extends downward such that a portion of the collar portion 2560 is located proximate the distal end 2508 of the tank portion 2502 and is configured to retain the heating member 2520 and at least a portion of the liquid transport element 2521. In the depicted implementation, the heating member 2520 in the installed position contacts a top surface of the liquid transport element 2521.

In various implementations, the liquid transport element 2521 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, the cartridge 2500 further includes a hood feature 2562, which is configured to be located in the bottom of the mouthpiece portion 2510. In the depicted implementation, the hood feature 2562 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, the hood feature may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. The hood feature 2562 of the depicted implementation has a block shape with a solid top surface and openings defined in the bottom and side surfaces. In the depicted implementation, a vaporization chamber 2540 is located above the heating member 2520, and is defined, at least in part, by the collar portion 2560. In the depicted implementation, the collar portion 2560 also defines a vapor channel 2545 that originates proximate the vaporization chamber 2540 and extends upward, leading to the hood feature 2562. As noted above, aerosol is generated in the vaporization chamber 2540 when the heating member 2520 heats at least a portion of the liquid composition contained in the liquid transport element 2521. In the depicted implementation, the hood feature 2562 is configured to direct aerosol, collect condensation, and/or shield against liquid and high temperatures from directly exiting the cartridge 2500. As such, when a user draws on the aerosol delivery device, aerosol from the vaporization chamber 2540 may travel through the vapor channel 2545, be diverted by the hood feature 2562, and be delivered to the user via the exit portal 2515 of the mouthpiece portion 2510.

FIGS. 23 and 24 illustrate a cartridge in accordance with another implementation of the present disclosure. In particular, FIG. 23 illustrates an exploded perspective view of a cartridge 2700 according to an example implementation of the present disclosure, and FIG. 24 illustrates a partial cross-section view of the cartridge 2700. In various implementations, a portion of the cartridge 2700 is configured to be removably coupled with a cartridge receiving chamber of a corresponding control device. In many aspects, the cartridge 2700 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 2700 of the depicted implementation includes a tank portion 2702 that is defined by an outer tank wall 2704 that includes a proximal end 2706 and a distal end 2708. As such, the tank portion 2702 may be characterized in that the tank wall 2704 is a sidewall that is continuous around the tank, and the distal end 2708 defines a bottom wall. The tank portion 2702 is also configured to contain a liquid composition 2724 configured for vaporization (e.g., an e-liquid or aerosol precursor composition, as described above). The cartridge 2700 also includes a mouthpiece portion 2710 that is defined by an outer mouthpiece wall 2712 that includes a distal end 2716 and a proximal end 2714 with an exit portal 2715 defined therein. In the depicted implementation, the cartridge 2700 also includes a collar portion 2760, at least a portion of which is positioned between the mouthpiece portion 2710 and the tank portion 2702. In the depicted implementation, the collar portion 2760 is configured to be joined to the mouthpiece portion 2710 and the tank portion 2702 via a press or snap-fit connection; however, in other implementations, other attachment methods are possible (e.g., via adhesives, heat staking/welding, ultrasonic welding, etc.) or any combination thereof.

In the depicted implementation, one or more of the mouthpiece portion 2710, the collar portion 2760, and the tank portion 2702 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 2700 further includes a heating member 2720 and a pair of electrical contacts 2725A, 2725B that are configured to electrically connect the heating member 2720 with the battery and/or control component of a control device. In the depicted implementation, the contacts 2725A, 2725B are located on opposite sides of the cartridge 2700 and are configured to be attached to the collar portion 2760. Although in the depicted implementation the contacts 2725A, 2725B are configured to be attached to the collar portion 2760 via a press-fit or snap fit attachment, in other implementations other forms of attachment are possible, including, for example, via an adhesive or via an insert molding process. In the depicted implementation, the heating member 2720 is located proximate the distal end 2708 of the tank portion 2702. As such, the electrical contacts 2725A, 2725B extend downward such that the corresponding ends thereof contact the heating member 2720. In various implementations, the heating member 2720 may be retained by the collar portion 2760 via a press-fit or snap fit attachment, although other forms of attachment are possible, including, for example, via an adhesive or via an insert molding process or being trapped by the collar portion 2760 (e.g., being trapped between the collar portion 2760 and one or more liquid transport elements). In the depicted implementation, the electrical contacts 2725A, 2725B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 2720 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 2720 may be integrated with the liquid transport element 2721. Other types of heating members may also be utilized, as noted above.

The cartridge 2700 of the depicted implementation also includes a liquid transport element 2721. In the depicted implementation, at least a portion of the liquid transport element 2721 is configured to be located proximate the heating member 2720. In the depicted implementation, the liquid transport element 2721 is disposed above the heating member 2720 and extends between the heating member 2720 and a metering plate 2735. The metering plate 2735 of the depicted implementation comprises a flat feature that includes a plurality of openings. In the depicted implementation, the metering plate 2735 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, the metering plate may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

In the installed position, the heating member 2720 of the depicted implementation contacts a bottom surface of the liquid transport element 2721, and a top surface of the liquid transport element 2721 contacts a bottom surface of the metering plate 2735. In the depicted implementation, the metering plate 2735 is disposed in the tank 2702 and below the liquid composition 2724. As such, the metering plate 2735 is configured to deliver liquid composition from the tank 2702 to the liquid transport element 2721. As shown in the figures, the collar portion 2760 of the depicted implementation extends downward such that a portion of the collar portion 2760 is located proximate the distal end 2708 of the tank portion 2702 and is configured to retain the heating member 2720, the liquid transport element 2721, and the metering plate 2735. Additionally, when installed a gap 2747 is formed between the collar portion 2760 and an inside surface of the tank portion 2702, which is configured as an aerosol path.

In various implementations, the liquid transport element 2721 may be formed of one or more materials configured for transport of a liquid, such as by capillary action. In some implementations, for example, the liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport element thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, a vaporization chamber 2740 is formed below the heating member 2720 and proximate the distal end 2708 of the tank portion 2702. In particular, a vaporization chamber 2740 is defined, at least in part, by the collar portion 2760 and the distal end 2708 of the tank portion 2702. As noted above, aerosol is generated in the vaporization chamber 2740 when the heating member 2720 heats at least a portion of the liquid composition contained in the liquid transport element 2721. Based on the features of the cartridge 2700, when a user draws on the aerosol delivery device aerosol formed in the vaporization chamber 2740 extends outward and then travels through the aerosol path between the collar portion 2760 and the tank portion 2702 where it is delivered to the user via the exit portal 2715 of the mouthpiece portion 2710.

FIG. 25 illustrates a cartridge in accordance with another implementation of the present disclosure. In particular, FIG. 25 illustrates a partial cross-section view of a cartridge 2900. In various implementations, a portion of the cartridge 2900 is configured to be removably coupled with a cartridge receiving chamber of a corresponding control device. In many aspects, the cartridge 2900 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figure, the cartridge 2900 of the depicted implementation includes a tank portion 2902 that is defined by an outer tank wall 2904 that includes a proximal end 2906 and a distal end 2908. As such, the tank portion 2902 may be characterized in that the tank wall 2904 is a sidewall that is continuous around the tank, and the distal end 2908 defines a bottom wall. The tank portion 2902 is also configured to contain a liquid composition 2924 configured for vaporization (e.g., an e-liquid or aerosol precursor composition, as described above). The cartridge 2900 also includes a mouthpiece portion 2910 that is defined by an outer mouthpiece wall 2912 that includes a distal end 2916 and a proximal end 2914 with one or more exit portals 2915 defined therein. In the depicted implementation, the cartridge 2900 also includes a collar portion 2960 that is positioned between the mouthpiece portion 2910 and the tank portion 2902. In the depicted implementation, the collar portion 2960 is configured to be joined to the mouthpiece portion 2910 and the tank portion 2902 via a press or snap-fit connection; however, in other implementations, other attachment methods are possible (e.g., via adhesives, heat staking/welding, ultrasonic welding, etc.) or any combination thereof.

In some implementations, the outer tank wall 2904 may be configured to be one of at least partially transparent or translucent so that the liquid composition 2924 contained therein is visible externally. As such, in some implementations, the entire outer tank wall 2904 may be transparent or translucent. Alternatively, in some implementations, only a single side, or a portion (or portions) of one or more sides, of the outer tank wall 2904 may be transparent or translucent while the remaining portions of the outer tank wall may be substantially opaque. In some embodiments, the outer tank wall 2904 or a portion thereof may be substantially opaque, and a strip extending from the proximal end 2906 of the tank 2902 to the distal end 2908 of the tank may be transparent or translucent. In further implementations, the outer tank wall 2904 may be colored. In some implementations, the color can be configured so that the liquid composition 2924 within the tank 2902 is still visible, such by using a transparent or translucent outer tank wall. In other implementations, the tank wall can be configured so that the outer tank wall 2904 has a substantially opaque color.

In the depicted implementation, one or more of the mouthpiece portion 2910, the collar portion 2960, and the tank portion 2902 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figure, the cartridge 2900 further includes a heating member 2920 and a pair of electrical contacts 2925A, 2925B that are configured to electrically connect the heating member 2920 with the battery and/or control component of a control device. In the depicted implementation, the contacts 2925A, 2925B are located on opposite sides of the cartridge 2900 and are configured to be attached to the collar portion 2960. Although in the depicted implementation the contacts 2925A, 2925B are configured to be attached to the collar portion 2960 via a press-fit or snap fit attachment, in other implementations other forms of attachment are possible, including, for example, via an adhesive or via an insert molding process. In the depicted implementation, the electrical contacts 2925A, 2925B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 2920 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum $(Mo(Si, Al)_2)$, titanium, platinum, silver, palladium, alloys of silver and palladium, graphite and graphite-based materials (e.g., carbon-based foams and yarns). In further implementations, the heating member 2920 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 2920 may be integrated with the first liquid transport element 2921. Other types of heating members (e.g., laser diodes, microheaters, etc.) may also be utilized, as noted above.

The cartridge 2900 of the depicted implementation also includes a pair of liquid transport elements. In particular, the cartridge 2900 includes a first liquid transport element 2921, and a second liquid transport element 2922. In the depicted implementation, a portion of the heating member 2920 is configured to be wrapped around a portion of the first liquid transport element 2921 in the area of the collar portion 2960. In the depicted implementation, the second liquid transport element 2922 has a relatively flat shape that includes an opening therein configured to surround a portion of the first liquid transport element 2921 such that the second liquid transport element 2922 forms a seal around the first liquid transport element 2921. In the depicted implementation, the first liquid transport element 2921 has a substantially cylindrical and hollow shape and is substantially aligned with the longitudinal axis of the cartridge. In the depicted implementation, the first liquid transport element 2921 extends thorough the second liquid transport element 2922 and the liquid composition 2924 to the bottom of the tank portion 2902. In the depicted implementation, the outer diameter of the second liquid transport element 2922 is larger than the outer diameter of the first liquid transport element 2921 and the length of the first liquid transport 2921 element is longer than the length of the second liquid transport element 2922.

In the depicted implementation, the cartridge 2900 also includes an upper frame portion 2931 that may include various features configured to retain the heating member 2920 and at least a portion of the first liquid transport element 2921. In the depicted implementation, the upper frame portion 2931 is constructed of a thermoplastic elastomer (TPE) or a silicone material, although other materials are possible. The upper frame portion 2931 of the depicted implementation is also configured to facilitate connection (such as, for example, by pressing together) the ends of the heating member 2920 to the respective electrical contacts 2925A, 2925B. In the depicted implementation, at least a portion of one or more of the upper frame portion 2931, the heating member 2920, the first liquid transport element 2921, the second liquid transport element 2922, and the electrical contacts 2925A, 2925B are contained within the collar portion 2960.

In various implementations, one or both of the first liquid transport element 2921 and the second liquid transport element 2922 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 2921 comprises a ceramic material and the second liquid transport element 2922 comprises a semi-rigid material. In the depicted implementation, the first liquid transport element 2921 and the second liquid transport element 2922 are configured to be press-fit into the collar portion 2960, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 2920 is wrapped around a portion of the first liquid transport element 2921. In the depicted implementation, a vaporization chamber 2940 is located in an area around the first liquid transport element 2921 upon which the heating member 2920 is wrapped, and is defined, at least in part, by the upper frame portion 2931. As noted above, aerosol is generated in the vaporization chamber 2940 when the heating member 2920 heats at least a portion of the liquid composition contained in the first liquid transport element 2921. As such, when a user draws on the aerosol delivery device, aerosol from the vaporization chamber 2940 may be delivered to the user via the exit portal 2915 of the mouthpiece portion 2910.

FIG. 26 illustrates a cartridge in accordance with another implementation of the present disclosure. In particular, FIG. 26 illustrates a partial cross-section view of a cartridge 3100. In various implementations, a portion of the cartridge 3100 is configured to be removably coupled with a cartridge receiving chamber of a corresponding control device. In many aspects, the cartridge 3100 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figure, the cartridge 3100 of the depicted implementation includes a tank portion 3102 that is defined by an outer tank wall 3104 that includes a proximal end 3106 and a distal end 3108. As such, the tank portion 3102 may be characterized in that the tank wall 3104 is a sidewall that is continuous around the tank, and the distal end 3108 defines a bottom wall. The tank portion 3102 is also configured to contain a liquid composition 3124 configured for vaporization (e.g., an e-liquid or aerosol precursor composition, as described above). The cartridge 3100 also includes a mouthpiece portion 3110 that is defined by an outer mouthpiece wall 3112 that includes a distal end 3116 and a proximal end 3114 with one or more exit portals 3115 defined therein. In the depicted implementation, the cartridge 3100 also includes a collar portion 3160 that is positioned between the mouthpiece portion 3110 and the tank portion 3102. In the depicted implementation, the collar portion 3160 is configured to be joined to the mouthpiece portion 3110 and the tank portion 3102 via a press or snap-fit connection; however, in other implementations, other attachment methods are possible (e.g., via adhesives, heat staking/welding, ultrasonic welding, etc.) or any combination thereof.

In some implementations, the outer tank wall 3104 may be configured to be one of at least partially transparent or translucent so that the liquid composition 3124 contained therein is visible externally. As such, in some implementations, the entire outer tank wall 3104 may be transparent or translucent. Alternatively, in some implementations, only a single side, or a portion (or portions) of one or more sides, of the outer tank wall 3104 may be transparent or translucent while the remaining portions of the outer tank wall may be substantially opaque. In some embodiments, the outer tank wall 3104 or a portion thereof may be substantially opaque, and a strip extending from the proximal end 3106 of the tank 3102 to the distal end 3108 of the tank may be transparent or translucent. In further implementations, the outer tank wall 3104 may be colored. In some implementations, the color can be configured so that the liquid composition 3124 within the tank 3102 is still visible, such by using a transparent or translucent outer tank wall. In other implementations, the tank wall can be configured so that the outer tank wall 3104 has a substantially opaque color.

In the depicted implementation, one or more of the mouthpiece portion 3110, the collar portion 3160, and the tank portion 3102 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figure, the cartridge 3100 further includes a heating member 3120 and a pair of electrical contacts 3125A, 3125B that are configured to electrically connect the heating member 3120 with the battery and/or control component of a control device. In the depicted implementation, the contacts 3125A, 3125B are located on opposite sides of the cartridge 3100 and are configured to be attached to the collar portion 3160. Although in the depicted implementation the contacts 3125A, 3125B are configured to be attached to the collar portion 3160 via a press-fit or snap fit attachment, in other implementations other forms of attachment are possible, including, for example, via an adhesive or via an insert molding process. In the depicted implementation, the electrical contacts 3125A, 3125B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In various implementations, the heating member may comprise one or more different materials configured to produce heat when electrical current is applied therethrough. In the depicted implementation, the heating member 3120 comprises a wire coil. Example materials from which the wire coil may be formed include, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member 3120 may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 3120 may be integrated with the first liquid transport element 3121. Other types of heating members (e.g., laser diodes, microheaters, etc.) may also be utilized, as noted above.

The cartridge 3100 of the depicted implementation also includes a pair of liquid transport elements. In particular, the cartridge 3100 includes a first liquid transport element 3121, and a second liquid transport element 3122. In the depicted implementation, a portion of the heating member 3120 is configured to be wrapped around a portion of the first liquid transport element 3121 in the area of the collar portion 3160. In the depicted implementation, the second liquid transport element 3122 has a relatively flat shape that includes an opening therein configured to surround a portion of the first liquid transport element 3121 such that the second liquid transport element 3122 forms a seal around the first liquid transport element 3121. In the depicted implementation, the first liquid transport element 3121 has a substantially cylindrical and solid (e.g., non-hollow) shape and is substantially aligned with the longitudinal axis of the cartridge. In the depicted implementation, the first liquid transport element 3121 extends thorough the second liquid transport element 3122 and the liquid composition 3124 to the bottom of the tank portion 3102. In particular, one end of first liquid transport element 3121 is attached to the mouthpiece portion 3110 via a retaining ring 3137 and the other end of the first liquid transport element 3121 extends to the bottom of the tank portion 3102. In the depicted implementation, the outer diameter of the second liquid transport element 3122 is larger than the outer diameter of the first liquid transport element 2921 and the length of the first liquid transport 3121 element is longer than the length of the second liquid transport element 3122.

In the depicted implementation, the cartridge 3100 also includes an upper frame portion 3131 that may include various features configured to retain the heating member 3120 and at least a portion of the first liquid transport element 3121. In the depicted implementation, the upper frame portion 3131 is constructed of a thermoplastic elastomer (TPE) or a silicone material, although other materials are possible. The upper frame portion 3131 of the depicted implementation is also configured to facilitate connection (such as, for example, by pressing together) the ends of the heating member 3120 to the respective electrical contacts 3125A, 3125B. In the depicted implementation, at least a portion of one or more of the upper frame portion 3131, the heating member 3120, the first liquid transport element 3121, the second liquid transport element 3122, and the electrical contacts 3125A, 3125B are contained within the collar portion 3160.

In various implementations, one or both of the first liquid transport element 3121 and the second liquid transport element 3122 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 3121 comprises a fibrous material and the second liquid transport element 3122 comprises a semi-rigid material. In the depicted implementation, the second liquid transport element 3122 and the retaining ring 3137 are configured to be press-fit into the collar portion 3160, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 3120 is wrapped around a portion of the first liquid transport element 3121. In the depicted implementation, a vaporization chamber 3140 is located in an area around the first liquid transport element 3121 upon which the heating member 3120 is wrapped, and is defined, at least in part, by the upper frame portion 3131. As noted above, aerosol is generated in the vaporization chamber 3140 when the heating member 3120 heats at least a portion of the liquid composition contained in the first liquid transport element 3121. As such, when a user draws on the aerosol delivery device, aerosol from the vaporization chamber 3140 may be delivered to the user via the exit portal 3115 of the mouthpiece portion 3110.

FIGS. 27 and 28 illustrate a cartridge in accordance with another implementation of the present disclosure. In particular, FIG. 27 illustrates an exploded perspective view of a cartridge 3300 according to an example implementation of the present disclosure, and FIG. 28 illustrates a partial cross-section view of the cartridge 3300. In various implementations, a portion of the cartridge 3300 is configured to be removably coupled with a cartridge receiving chamber of a corresponding control device. In many aspects, the cartridge 3300 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 3300 of the depicted implementation includes a tank portion 3302 that is defined by an outer tank wall 3304 that includes a proximal end 3306 and a distal end 3308. As such, the tank portion 3302 may be characterized in that the tank wall 3304 is a sidewall that is continuous around the tank, and the distal end 3308 defines a bottom wall. The tank portion 3302 is also configured to contain a liquid composition configured for vaporization (e.g., an e-liquid or aerosol precursor composition, as described above). The cartridge 3300 also includes a mouthpiece portion 3310 that is defined by an outer mouthpiece wall 3312 that includes a distal end 3316 and a proximal end 3314 with one or more exit portals 3315 defined therein. In the depicted implementation, the cartridge 3300 also includes a collar portion 3360 that is positioned between the mouthpiece portion 3310 and the tank portion 3302. In the depicted implementation, the collar portion 3360 is configured to be joined to the mouthpiece portion 3310 and the tank portion 3302 via a press or snap-fit connection; however, in other implementations, other attachment methods are possible (e.g., via adhesives, heat staking/welding, ultrasonic welding, etc.) or any combination thereof.

In some implementations, the outer tank wall 3304 may be configured to be one of at least partially transparent or translucent so that the liquid composition contained therein is visible externally. As such, in some implementations, the entire outer tank wall 3304 may be transparent or translucent. Alternatively, in some implementations, only a single side, or a portion (or portions) of one or more sides, of the outer tank wall 3304 may be transparent or translucent while the remaining portions of the outer tank wall may be substantially opaque. In some embodiments, the outer tank wall 3304 or a portion thereof may be substantially opaque, and a strip extending from the proximal end 3306 of the tank 3302 to the distal end 3308 of the tank may be transparent or translucent. In further implementations, the outer tank wall 3304 may be colored. In some implementations, the color can be configured so that the liquid composition within the tank 3302 is still visible, such by using a transparent or translucent outer tank wall. In other implementations, the tank wall can be configured so that the outer tank wall 3304 has a substantially opaque color.

In the depicted implementation, one or more of the mouthpiece portion 3302, the collar portion 3360, and the tank portion 3302 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in the figures, the cartridge 3300 further includes a heating member 3320 and a pair of electrical contacts (not shown) that are configured to electrically connect the heating member 3320 with the battery and/or control component of a control device. In the depicted implementation, the contacts are located on opposite sides of the cartridge 3300 and are configured to be attached to the collar portion 3360. Although in the depicted implementation the contacts are configured to be attached to the collar portion 3360 via a press-fit or snap fit attachment, in other implementations other forms of attachment are possible, including, for example, via an adhesive or via an insert molding process. In the depicted implementation, the electrical contacts are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 3320 may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 3320 may be integrated with the first liquid transport element 3321. Other types of heating members (e.g., laser diodes, microheaters, etc.) may also be utilized, as noted above.

The cartridge 3300 of the depicted implementation also includes a plurality of liquid transport elements. In particular, the cartridge 3300 includes a first liquid transport element 3321 and a pair of second transport elements 3322A, 3322B. In the depicted implementation, at least a portion of the first liquid transport element 3321 is configured to be located proximate the heating member 3320. In addition, the second liquid transport elements 3322A, 3322B of the depicted implementation are configured to extend between the first liquid transport element 3321 and the bottom of the tank portion 3302. In the depicted implementation, the second liquid transport elements 3322A, 3322B comprise capillary tubes configured to deliver liquid composition to the first liquid transport element 3321 via capillary effect. In the depicted implementation, the second liquid transport elements 3322A, 3322B have a substantially cylindrical and hollow shape, although other configurations are possible.

As shown in the figures, the first liquid transport element 3321 and the heating member 3320 are located in the collar portion 3360 of the cartridge 3300. The heating member 3320 of the depicted implementation comprises a flat heating element, and the first liquid transport element 3321 comprises a relatively flat element having substantially block shape. Although other configurations are possible, in the depicted implementation the length and width of the first liquid transport element 3321 are larger than its thickness. In such a manner, the heating member 3320 in the installed position contacts a top surface of the first liquid transport element 3321. In the depicted implementation, the second liquid transport elements 3322A, 3322B are substantially aligned with the longitudinal axis of the cartridge and are spaced from each other such that the top surfaces of the second liquid transport elements 3322A, 3322B contact a bottom surface of the first liquid transport element 3321 and the bottom surfaces of the second liquid transport elements 3322A, 3322B are proximate (and in the depicted implementation spaced slightly away from) the bottom of the tank portion 3302.

In the depicted implementation, the first liquid transport element 3321 may comprise a fibrous material, and the second liquid transport elements 3322A, 3322B may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. In still other implementations, one or both of the first liquid transport element 3321 and the second liquid transport elements 3322A, 3322B may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the second liquid transport elements 3322A, 3322B are configured to be press-fit into the collar portion 3360. In some implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 3320 is located in the collar portion 3360. In the depicted implementation, a vaporization chamber 3340 is located in an area above the heating member 3320, and is defined, at least in part, by the mouthpiece portion 3310. As noted above, aerosol is generated in the vaporization chamber 3340 when the heating member 3320 heats at least a portion of the liquid composition contained in the first liquid transport element 3321. As such, when a user draws on the aerosol delivery device, aerosol from the vaporization chamber 3340 may be delivered to the user via the exit portal 3315 of the mouthpiece portion 3310.

FIGS. 29 and 30 illustrate a cartridge in accordance with another implementation of the present disclosure. In particular, FIG. 29 illustrates an exploded perspective view of a cartridge 3500 according to an example implementation of the present disclosure, and FIG. 30 illustrates a partial cross-section view of the cartridge 3500. In various implementations, a portion of the cartridge 3500 is configured to be removably coupled with a cartridge receiving chamber of a corresponding control device. In many aspects, the cartridge 3500 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 3500 of the depicted implementation includes a tank portion 3502 that is defined by an outer tank wall 3504 that includes a proximal end 3506 and a distal end 3508. As such, the tank portion 3502 may be characterized in that the tank wall 3504 is a sidewall that is continuous around the tank, and the distal end 3508 defines a bottom wall. The tank portion 3502 is also configured to contain a liquid composition configured for vaporization (e.g., an e-liquid or aerosol precursor composition, as described above). The cartridge 3500 also includes a mouthpiece portion 3510 that is defined by an outer mouthpiece wall 3512 that includes a distal end 3516 and a proximal end 3514 with an exit portal 3515 defined therein. In the depicted implementation, the cartridge 3500 also includes a collar portion 3560 that is positioned between the mouthpiece portion 3510 and the tank portion 3502. In the depicted implementation, the collar portion 3560 is configured to be joined to the mouthpiece portion 3510 and the tank portion 3502 via a press or snap-fit connection; however, in other implementations, other attachment methods are possible (e.g., via adhesives, heat staking/welding, ultrasonic welding, etc.) or any combination thereof.

In some implementations, the outer tank wall 3504 may be configured to be one of at least partially transparent or translucent so that the liquid composition contained therein is visible externally. As such, in some implementations, the entire outer tank wall 3504 may be transparent or translucent. Alternatively, in some implementations, only a single side, or a portion (or portions) of one or more sides, of the outer tank wall 3504 may be transparent or translucent while the remaining portions of the outer tank wall may be substantially opaque. In some embodiments, the outer tank wall 3504 or a portion thereof may be substantially opaque, and a strip extending from the proximal end 3506 of the tank 3502 to the distal end 3508 of the tank may be transparent or translucent. In further implementations, the outer tank wall 3504 may be colored. In some implementations, the color can be configured so that the liquid composition within the tank 3502 is still visible, such by using a transparent or translucent outer tank wall. In other implementations, the tank wall can be configured so that the outer tank wall 3504 has a substantially opaque color.

In the depicted implementation, one or more of the mouthpiece portion 3510, the collar portion 3560, and the tank portion 3502 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

The cartridge 3500 further includes a heating member 3520 and a pair of electrical contacts (not shown) that are configured to electrically connect the heating member 3520 with the battery and/or control component of a control device. In the depicted implementation, the contacts are located on opposite sides of the cartridge 3500 and are configured to be attached to the collar portion 3560. Although in the depicted implementation the contacts are configured to be attached to the collar portion 3560 via a press-fit or snap fit attachment, in other implementations other forms of attachment are possible, including, for example, via an adhesive or via an insert molding process. In the depicted implementation, the electrical contacts are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 3520 may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 3520 may be integrated with the first liquid transport element 3521. Other types of heating members (e.g., laser diodes, microheaters, etc.) may also be utilized, as noted above.

The cartridge 3500 of the depicted implementation also includes a plurality of liquid transport elements. In particular, the cartridge 3500 includes a first liquid transport element 3521 and a plurality of second transport elements. Although other configurations are possible, the depicted implementation includes five second liquid transport elements 3522A, 3522B, 3522C, 3522D, 3522E. In the depicted implementation, at least a portion of the first liquid transport element 3521 is configured to be located proximate the heating member 3520. In addition, the second liquid transport elements 3522A, 3522B, 3522C, 3522D, 3522E of the depicted implementation are configured to extend between the first liquid transport element 3521 and the bottom of the tank portion 3502. In the depicted implementation, the second liquid transport elements 3522A, 3522B, 3522C, 3522D, 3522E comprise capillary tubes configured to deliver liquid composition to the first liquid transport element 3521 via capillary effect. In the depicted implementation, the second liquid transport elements 3522A, 3522B, 3522C, 3522D, 3522E have a substantially cylindrical and hollow shape, although other configurations are possible.

As shown in the figures, the first liquid transport element 3521 and the heating member 3520 are located in the collar portion 3560 of the cartridge 3500. The heating member 3520 of the depicted implementation comprises a flat heating element, and the first liquid transport element 3521 comprises a relatively flat element having substantially block shape. Although other configurations are possible, in the depicted implementation the length and width of the first liquid transport element 3521 are larger than its thickness. In such a manner, the heating member 3520 in the installed position contacts a top surface of the first liquid transport element 3521. In the depicted implementation, the second liquid transport elements 3522A, 3522B, 3522C, 3522D, 3522E are substantially aligned with the longitudinal axis of the cartridge and are spaced from each other such that the top surfaces of the second liquid transport elements 3522A, 3522B, 3522C, 3522D, 3522E contact a bottom surface of the first liquid transport element 3521 and the bottom surfaces of the second liquid transport elements 3522A, 3522B, 3522C, 3522D, 3522E is proximate (and in the depicted implementation spaced slightly from) the bottom of the tank portion 3502.

In the depicted implementation, the first liquid transport element 3521 may comprise a fibrous material, and the second liquid transport elements 3522A, 3522B, 3522C, 3522D, 3522E may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. In still other implementations, one or both of the first liquid transport element 3521 and the second liquid transport elements 3522A, 3522B, 3522C, 3522D, 3522E may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the second liquid transport elements 3522A, 3522B, 3522C, 3522D, 3522E are configured to be press-fit into the collar portion 3560. In some implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 3520 is located in the collar portion 3560. In the depicted implementation, a vaporization chamber 3540 is located in an area above the heating member 3520, and is defined, at least in part, by the mouthpiece portion 3510. As noted above, aerosol is generated in the vaporization chamber 3540 when the heating member 3520 heats at least a portion of the liquid composition contained in the first liquid transport element 3521. As such, when a user draws on the aerosol delivery device, aerosol from the vaporization chamber 3540 may be delivered to the user via the exit portal 3515 of the mouthpiece portion 3510.

FIGS. 31 and 32 illustrate a cartridge in accordance with another implementation of the present disclosure. In particular, FIG. 31 illustrates an exploded perspective view of a cartridge 3700 according to an example implementation of the present disclosure, and FIG. 32 illustrates a partial cross-section view of the cartridge 3700. In various implementations, a portion of the cartridge 3700 is configured to be removably coupled with a cartridge receiving chamber of a corresponding control device. In many aspects, the cartridge 3700 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 3700 of the depicted implementation includes a tank portion 3702 that is defined by an outer tank wall 3704 that includes a proximal end 3706 and a distal end 3708. As such, the tank portion 3702 may be characterized in that the tank wall 3704 is a sidewall that is continuous around the tank, and the distal end 3708 defines a bottom wall. The tank portion 3702 is also configured to contain a liquid composition configured for vaporization (e.g., an e-liquid or aerosol precursor composition, as described above). The cartridge 3700 also includes a mouthpiece portion 3710 that is defined by an outer mouthpiece wall 3712 that includes a distal end 3716 and a proximal end 3714 with an exit portal 3715 defined therein. In the depicted implementation, the cartridge 3700 also includes an inner frame member 3764 that is positioned below the distal end 3716 of the mouthpiece portion 3710 and between the proximal end 3706 and the distal end 3708 of the tank portion 3702. In the depicted implementation, the inner frame member 3764 comprises a main portion 3765 and a sealing portion 3767. In the depicted implementation, the mouthpiece portion 3710 and the tank portion 3702 are configured to join to one another via a press or snap-fit connection; however, in other implementations, other attachment methods are possible (e.g., via adhesives, heat staking/welding, ultrasonic welding, etc.) or any combination thereof. Likewise, in the depicted implementation, the inner frame 3764 is configured to be joined with the tank portion 3702 via a press or snap-fit connection; however, in other implementations, other attachment methods are possible (e.g., via adhesives, heat staking/welding, ultrasonic welding, etc.) or any combination thereof.

In the depicted implementation, one or more of the mouthpiece portion 3710 and the tank portion 3702 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof. In addition, in the depicted implementation the main portion 3765 of the inner frame member 3764 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), and the sealing portion 3767 of the inner frame member 3764 may be constructed of a thermoplastic elastomer (TPE) or a silicone material, although other materials are possible. As such, in some implementations, the sealing portion 3767 of the inner frame member 3764 may be formed via an overmolding or insert molding process with the main portion 3765 of the inner frame member 3764.

As shown in the figures, the cartridge 3700 further includes a heating member 3720 and a pair of electrical contacts 3725A, 3725B that are configured to electrically connect the heating member 3720 with the battery and/or control component of a control device. In the depicted implementation, the contacts 3725A, 3725B are located on opposite sides of the cartridge 3700 and are configured to extend through a portion of the sealing portion 3767 of the inner frame, the heating member 3720, and into the mouthpiece portion 3710. Although in the depicted implementation the contacts 3725A, 3725B are configured to be attached to the tank portion 3702 via an insert molding process, although other methods are possible, including, for example, via a press-fit or snap fit attachment, or via an adhesive. In the depicted implementation, the electrical contacts 3725A, 3725B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold. The tank portion 3702 of the depicted implementation also includes a metal plate 3766 (see FIG. 32), which is configured to interact with a magnetic feature of the control device to facilitate a mechanical connection between the cartridge 3700 and the control device. In various implementations, the metal plate 3766 may comprise any material configured to be attracted by a magnet, such as various ferromagnetic materials, including, but not limited, to iron, nickel, cobalt, alloys such as steel, and/or any combination thereof. Although other methods are possible, in the depicted implementation the metal plate 3766 is embedded into the bottom wall of the tank portion 3702 via an insert molding process.

In addition to providing electrical connectivity between the heating member 3720 and the battery and/or control component of a control device, the electrical contacts 3725A, 3725B of the depicted implementation may also serve other functions. For example, as shown in detail in FIG. 43, in some implementations the ends of the electrical contacts 3725A, 3725B may extend beyond the heating member 3720 and into corresponding channels formed in the mouthpiece portion 3710. In such a manner, the electrical contacts 3725A, 3725B may also facilitate assembly of the mouthpiece portion 3710. Furthermore, the electrical contacts 3725A, 3725B of some implementations may facilitate attachment and/or retention of the mouthpiece portion 3710 to the tank portion 3702. As such, at least a portion of the ends of the electrical contacts 3725A, 3725B proximate the mouthpiece portion 3710 may create an interference fit with the corresponding channels of the mouthpiece portion. Additionally or alternately, at least a portion of the ends of the electrical contacts 3725A, 3725B proximate the mouthpiece portion 3710 may be knurled so as to facilitate connection between the mouthpiece portion 3710 and the tank portion 3702. In various implementations, a variety of different knurled finishes are possible including, for example, straight knurling, helical knurling, diamond knurling, etc. In some implementations, the knurled ends of the electrical contacts 3725A, 3725B may also facilitate the mechanical connection between the heating member 3720 and the electrical contacts 3725A, 3725B. In further implementations, the heating member 3720 itself may include features that facilitate connection between heating member 3720 and the electrical contacts 3725A, 3725B. For example, FIG. 44 illustrates a perspective view of a portion of the cartridge of FIGS. 31 and 32. In the depicted implementation, the heating member 3720 includes attachment apertures 3770A, 3770B that are configured to engage ends of the electrical contacts 3725A, 3725B. As shown in the detailed portion of the figure, in some implementations the apertures 3770A, 3770B may have a star (or other) pattern that includes a plurality of projecting features configured to "bite" into the ends of the electrical contacts 3725A, 3725B when the heating member 3720 is assembled on the electrical contacts 3725A, 3725B.

In the depicted implementation, the heating member 3720 comprises a flat heating element and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 3720 may be integrated with the first liquid transport element 3721. Other types of heating members (e.g., laser diodes, microheaters, etc.) may also be utilized, as noted above.

The cartridge 3700 of the depicted implementation also includes a pair of liquid transport elements. In particular, the cartridge 3700 includes a first liquid transport element 3721 and a second liquid transport element 3722. In the depicted implementation, at least a portion of the first liquid transport element 3721 is configured to be located proximate the heating member 3720. In addition, the second liquid transport element 3722 of the depicted implementation is configured to extend between the first liquid transport element 3721 and the liquid composition contained within the tank 3702 such that the second liquid transport element 3722 is configured to transport liquid to the first liquid transport element 3721. In the depicted implementation, the second liquid transport element 3722 has a T-shape with a transverse portion 3727 that intersects a longitudinal portion 3729. Although other configurations are possible, in the depicted implementation, the length of the longitudinal portion 3729 is longer than the length of the transverse portion 3727.

As shown in the figures, the first liquid transport element 3721, the heating member 3720, and a portion of the second liquid transport element 3722 are located in the inner frame portion 3764 of the cartridge 3700. In such a manner, the heating member 3720 in the installed position contacts a top surface of the first liquid transport element 3721, and a top surface of the transverse portion 3727 of the second liquid transport element 3722 contacts a bottom surface of the first liquid transport element 3721. In such a manner, the second liquid transport element 3722 is configured to deliver liquid composition to the first liquid transport element 3721.

In various implementations, one or both of the first liquid transport element 3721 and the second liquid transport element 3722 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In the depicted implementation, the first liquid transport element 3721 comprises a fibrous material and the second liquid transport element 3722 comprises a semi-rigid material. In the depicted implementation, the second liquid transport element 3722 is configured to be press-fit into the inner frame member 3764, although other methods of attachment are possible. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, at least a portion of the heating member 3720 is located in the inner frame member 3764. In the depicted implementation, a vaporization chamber 3740 is located in an area above the heating member 3720, and is defined, at least in part, by the mouthpiece portion 3710. As noted above, aerosol is generated in the vaporization chamber 3740 when the heating member 3720 heats at least a portion of the liquid composition contained in the first liquid transport element 3721. As such, when a user draws on the aerosol delivery device, aerosol from the vaporization chamber 3740 may be delivered to the user via the exit portal 3715 of the mouthpiece portion 3710.

In various implementations, at least a portion of the heating member may be referred to as being proximate the distal end of the mouthpiece portion. To illustrate this point, reference is made to FIG. 45, which depicts a partial cross-section view of the cartridge 3700 of FIGS. 31 and 32.

In particular, FIG. 45 depicts the cartridge 3700 including the tank portion 3702 defined by the outer tank wall 3704 that includes the proximal end 3706 and the distal end 3708, and the mouthpiece portion 3710 defined by the outer mouthpiece wall 3712 that includes the proximal end 3714 with the exit portal 3715 defined therein and the distal end 3716 that engages the proximal end 3706 of the tank portion 3702. FIG. 45 also depicts the heating member 3720 and the electrical contacts 3725A, 3725B configured to electrically connect the heating member 3720 with the battery and/or control component of the control device. As evident in the figure, for this implementation and many of the other depicted implementations, the heating member 3720 may be characterized as being located proximate the distal end 3716 (designated in the figure by reference line M-D) of the mouthpiece portion 3710.

FIGS. 33 and 34 illustrate a cartridge in accordance with another implementation of the present disclosure. In particular, FIG. 33 illustrates an exploded perspective view of a cartridge 3900 according to an example implementation of the present disclosure, and FIG. 34 illustrates a partial cross-section view of the cartridge 3900. In various implementations, a portion of the cartridge 3900 is configured to be removably coupled with a cartridge receiving chamber of a corresponding control device. In many aspects, the cartridge 3900 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 3900 of the depicted implementation includes a tank portion 3902 that is defined by an outer tank wall 3904 that includes a proximal end 3906 and a distal end 3908. As such, the tank portion 3902 may be characterized in that the tank wall 3904 is a sidewall that is continuous around the sides of the tank and includes an internal intermediate wall 3949, and an open distal end 3908 below the intermediate wall 3949. In the depicted implementation, the open distal end 3908 of the tank portion 3902 is covered by a bottom cap 3972 and a lower frame 3968. The tank portion 3902 is also configured to contain a liquid composition configured for vaporization (e.g., an e-liquid or aerosol precursor composition, as described above). The cartridge 3900 also includes a mouthpiece portion 3910 that is defined by an outer mouthpiece wall 3912 that includes a distal end 3916 and a proximal end 3914 with an exit portal 3915 defined therein. In the depicted implementation, the cartridge 3900 also includes a collar portion 3960, at least a portion of which is positioned between the mouthpiece portion 3910 and the tank portion 3902. In the depicted implementation, the collar portion 3960 is configured to be joined to the mouthpiece portion 3910 and the tank portion 3902 via a press or snap-fit connection; however, in other implementations, other attachment methods are possible (e.g., via adhesives, heat staking/welding, ultrasonic welding, etc.) or any combination thereof.

In some implementations, the outer tank wall 3904 may be configured to be one of at least partially transparent or translucent so that the liquid composition contained therein is visible externally. As such, in some implementations, the entire outer tank wall 3904 may be transparent or translucent. Alternatively, in some implementations, only a single side, or a portion (or portions) of one or more sides, of the outer tank wall 3904 may be transparent or translucent while the remaining portions of the outer tank wall may be substantially opaque. In some embodiments, the outer tank wall 3904 or a portion thereof may be substantially opaque, and a strip extending from the proximal end 3906 of the tank 3902 to the distal end 3908 of the tank may be transparent or translucent. In further implementations, the outer tank wall 3904 may be colored. In some implementations, the color can be configured so that the liquid composition within the tank 3902 is still visible, such by using a transparent or translucent outer tank wall. In other implementations, the tank wall can be configured so that the outer tank wall 3904 has a substantially opaque color.

In the depicted implementation, one or more of the mouthpiece portion 3910, the collar portion 3960, the tank portion 3902, the lower frame 3968, and the bottom cap 3972 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 3900 further includes a heating member 3920 and a pair of electrical contacts 3925A, 3925B that are configured to electrically connect the heating member 3920 with the battery and/or control component of a control device. In the depicted implementation, the contacts 3925A, 3925B are located on opposite sides of the cartridge 3900 and are configured to be attached to at least one of the bottom cap 3972, the lower frame 3968, and the tank portion 3902. Although in the depicted implementation the contacts 3925A, 3925B are configured to be attached to one or more of these components via a press-fit or snap fit attachment, in other implementations other forms of attachment are possible, including, for example, via an adhesive or via an insert molding process. In the depicted implementation, the heating member 3920 is located proximate the distal end 3908 of the tank portion 3902. In various implementations, the heating member 3920 may be located in and/or retained by the tank portion 3902 via a press-fit or snap fit attachment, although other forms of attachment are possible, including, for example, via an adhesive or via an insert molding process or being trapped by the lower frame 3968 against the tank portion 3902. In the depicted implementation, the electrical contacts 3925A, 3925B are constructed of a conductive material. Examples of conductive materials include, but are not limited to, copper, beryllium copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

The bottom cap 3972 of the depicted implementation further includes a feature configured to retain a magnet 3970, which is configured to facilitate a mechanical connection between the cartridge 3900 and a control device. It should be noted that in other implementations, the bottom cap may include a component, such as, for example, a metal disk, configured to be attracted to a magnet located in the control device. In various implementations of the present disclosure, the magnet 3970 may comprise many different types of magnets, including rare earth magnets. For example, in some implementations, one or more magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more magnets may comprise Samarium Cobalt magnets (also known as SmCo magnets). In still other implementations, one or more magnets may comprise Ceramic/Ferrite magnets. In other implementations, one or more magnets may comprise Aluminum-Nickel-Cobalt (AlNiCo) magnets. In any of the foregoing implementations, one or more magnets may be plated and/or coated. For example, in some implementations, one or more magnets may be coated with nickel. In other implementations, one or more magnets may be coated with one or more of zinc, tin, copper, epoxy, silver and/or gold. In some implementations, one or more magnets may be coated with combinations of these materials. For example, in one implementation, one or more magnets may be coated with nickel, copper, and nickel again. In another implementation, one or more magnets may be coated with nickel, copper, nickel, and a top coating of gold.

In the depicted implementation, the heating member 3920 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 3920 may be integrated with the liquid transport element 3921. Other types of heating members may also be utilized, as noted above.

The cartridge 3900 of the depicted implementation also includes a liquid transport element 3921, at least a portion of which is configured to be located proximate the heating member 3920. In particular, in the depicted implementation the liquid transport element 3921 is located above the heating member 3920 and is configured to be captured by a feature of the intermediate wall 3949 of the tank portion 3902. In the depicted implementation, the liquid transport element 3921 has a relatively flat block-like shape.

In various implementations, the liquid transport element 3921 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

In the depicted implementation, the tank portion includes a vapor channel 3974 that is located on one side of the inside of the tank portion 3902. As shown in the drawings, a vaporization chamber 3940 is located in an area below the heating member 3920, and is defined, at least in part, by the lower frame 3968. As noted above, aerosol is generated in the vaporization chamber 3940 when the heating member 3920 heats at least a portion of the liquid composition contained in the first liquid transport element 3921. As such, when a user draws on the aerosol delivery device, aerosol from the vaporization chamber 3940 may be delivered to the user via the vapor channel 3974 in the tank portion 3902 and the exit portal 3915 of the mouthpiece portion 3910.

FIGS. 35 and 36 illustrate a cartridge in accordance with another implementation of the present disclosure. In particular, FIG. 35 illustrates an exploded perspective view of a cartridge 4100 according to an example implementation of the present disclosure, and FIG. 36 illustrates a partial cross-section view of the cartridge 4100. In various implementations, a portion of the cartridge 4100 is configured to be removably coupled with a cartridge receiving chamber of a corresponding control device. In many aspects, the cartridge 4100 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 4100 of the depicted implementation includes a tank portion 4102 that is defined by an outer tank wall 4104 that includes a proximal end 4106 and a distal end 4108. As such, the tank portion 4102 may be characterized in that the tank wall 4104 is a sidewall that is continuous around the sides of the tank and includes an internal intermediate wall 4149, and an open distal end 4108 below the intermediate wall 4149. In the depicted implementation, the open distal end 4108 of the tank portion 4102 is covered by a bottom cap 4172 and a lower frame 4168. The tank portion 4102 is also configured to contain a liquid composition configured for vaporization (e.g., an e-liquid or aerosol precursor composition, as described above). The cartridge 4100 also includes a mouthpiece portion 4110 that is defined by an outer mouthpiece wall 4112 that includes a distal end 4116 and a proximal end 4114 with one or more exit portals 4115 defined therein. In the depicted implementation, the distal end 4116 of the mouthpiece portion 4110 is configured to be joined to the proximal end 4106 of the tank portion via a press or snap-fit connection; however, in other implementations, other attachment methods are possible (e.g., via adhesives, heat staking/welding, ultrasonic welding, etc.) or any combination thereof. In the depicted implementation, the distal end of the cartridge portion 4110 includes a sealing member 4117 that is disposed around at least a portion of the distal end 4116 of the mouthpiece portion 4110. In the depicted implementation, the sealing member 4117 is constructed of a thermoplastic elastomer (TPE) or a silicone material, although other materials are possible. In some implementation, the sealing member 4117 may be a separate part that is attached to the mouthpiece portion 4110 via a stretch-fit or via adhesive; however, in other implementations, the sealing member 4117 may be part of the mouthpiece portion 4110, such as via an over molding process.

In some implementations, the outer tank wall 4104 may be configured to be one of at least partially transparent or translucent so that the liquid composition contained therein is visible externally. As such, in some implementations, the entire outer tank wall 4104 may be transparent or translucent. Alternatively, in some implementations, only a single side, or a portion (or portions) of one or more sides, of the outer tank wall 4104 may be transparent or translucent while the remaining portions of the outer tank wall may be substantially opaque. In some embodiments, the outer tank wall 4104 or a portion thereof may be substantially opaque, and a strip extending from the proximal end 4106 of the tank 4102 to the distal end 4108 of the tank may be transparent or translucent. In further implementations, the outer tank wall 4104 may be colored. In some implementations, the color can be configured so that the liquid composition within the tank 4102 is still visible, such by using a transparent or translucent outer tank wall. In other implementations, the tank wall can be configured so that the outer tank wall 4104 has a substantially opaque color.

In the depicted implementation, one or more of the mouthpiece portion 4110, the tank portion 4102, the lower frame 4168, and the bottom cap 4172 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 4100 further includes a heating member 4120 and a pair of electrical contacts 4125A, 4125B that are configured to electrically connect the heating member 4120 with the battery and/or control component of a control device. In the depicted implementation, the contacts 4125A, 4125B are located on opposite sides of the cartridge 4100 and are configured to be attached to at least one of the bottom cap 4172, the lower frame 4168, and the tank portion 4102. Although in the depicted implementation the contacts 4125A, 4125B are configured to be attached to one or more of these components via a press-fit or snap fit attachment, in other implementations other forms of attachment are possible, including, for example, via an adhesive or via an insert molding process. In the depicted implementation, the heating member 4120 is located proximate the distal end 4108 of the tank portion 4102. In various implementations, the heating member 4120 may be located in and/or retained by the tank portion 4102 via a press-fit or snap fit attachment, although other forms of attachment are possible, including, for example, via an adhesive or via an insert molding process or being trapped by the lower frame 4168 against the tank portion 4102. In the depicted implementation, the electrical contacts 4125A, 4125B are constructed of a conductive material. Examples of conductive materials include, but are not limited to, copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 4120 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum $(Mo(Si, Al)_2)$, titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 4120 may be integrated with the liquid transport element 4121. Other types of heating members may also be utilized, as noted above.

The cartridge 4100 of the depicted implementation also includes a liquid transport element 4121, at least a portion of which is configured to be located proximate the heating member 4120. In particular, in the depicted implementation the liquid transport element 4121 is located below the heating member 4120 and is configured to be captured by a feature of the lower frame 4168. In the depicted implementation, the liquid transport element 4121 has a relatively flat shape.

In various implementations, the liquid transport element 4121 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, a vaporization chamber 4140 is located in an area above the heating member 4120, and is defined, at least in part, by a portion of the intermediate wall 4149 of the tank portion 4102. In the depicted implementation, the cartridge also includes a separate vapor tube 4174 that is configured to extend between the vaporization chamber 4140 and the mouthpiece portion 4110. In the depicted implementation, the vapor tube 4110 may be constructed of a metal material (e.g., aluminum, stainless steel, metal alloys, etc.), although other materials are possible, including for example, a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof). In other implementations, the vapor tube may be constructed of other materials, including, for example, glass materials, ceramic materials (e.g., alumina, silica, mullite, silicon carbide, silicon nitride, aluminum nitride, etc.), composite materials, and/or any combinations thereof. As noted above, aerosol is generated in the vaporization chamber 4140 when the heating member 4120 heats at least a portion of the liquid composition contained in the first liquid transport element 4121. As such, when a user draws on the aerosol delivery device, aerosol from the vaporization chamber 4140 may be delivered to the user via the vapor tube 4174 and the exit portals 4115 of the mouthpiece portion 4110.

FIGS. 37 and 38 illustrate a cartridge in accordance with another implementation of the present disclosure. In particular, FIG. 37 illustrates an exploded perspective view of a cartridge 4300 according to an example implementation of the present disclosure, and FIG. 38 illustrates a partial cross-section view of the cartridge 4300. In various implementations, a portion of the cartridge 4300 is configured to be removably coupled with a cartridge receiving chamber of a corresponding control device. In many aspects, the cartridge 4300 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 4300 of the depicted implementation includes a tank portion 4302 that is defined by an outer tank wall 4304 that includes a proximal end 4306 and a distal end 4308. As such, the tank portion 4302 may be characterized in that the tank wall 4304 is a sidewall that is continuous around the sides of the tank, and the distal end 4308 defines a bottom wall. In the depicted implementation, a lower frame 4368 is located proximate the distal end 4308 of the tank portion, and an intermediate frame 4374 is located above the lower frame 4368. The tank portion 4302 is also configured to contain a liquid composition configured for vaporization (e.g., an e-liquid or aerosol precursor composition, as described above). The cartridge 4300 also includes a mouthpiece portion 4310 that is defined by an outer mouthpiece wall 4312 that includes a distal end 4316 and a proximal end 4314 with one or more exit portals 4315 defined therein. In the depicted implementation, the distal end 4316 of the mouthpiece portion 4310 is configured to be joined to the proximal end 4306 of the tank portion via a press or snap-fit connection; however, in other implementations, other attachment methods are possible (e.g., via adhesives, heat staking/welding, ultrasonic welding, etc.) or any combination thereof. In the depicted implementation, the distal end of the cartridge portion 4310 includes a sealing member 4317 that is disposed around at least a portion of the distal end 4316 of the mouthpiece portion 4310. In the depicted implementation, the sealing member 4317 is constructed of a thermoplastic elastomer (TPE) or a silicone material, although other materials are possible. In some implementation, the sealing member 4317 may be a separate part that is attached to the mouthpiece portion 4310 via a stretch-fit or via adhesive; however, in other implementations, the sealing member 4317 may be part of the mouthpiece portion 4310, such as via an over molding process.

In some implementations, the outer tank wall 4304 may be configured to be one of at least partially transparent or translucent so that the liquid composition contained therein is visible externally. As such, in some implementations, the entire outer tank wall 4304 may be transparent or translucent. Alternatively, in some implementations, only a single side, or a portion (or portions) of one or more sides, of the outer tank wall 4304 may be transparent or translucent while the remaining portions of the outer tank wall may be substantially opaque. In some embodiments, the outer tank wall 4304 or a portion thereof may be substantially opaque, and a strip extending from the proximal end 4306 of the tank 4302 to the distal end 4308 of the tank may be transparent or translucent. In further implementations, the outer tank wall 4304 may be colored. In some implementations, the color can be configured so that the liquid composition within the tank 4302 is still visible, such by using a transparent or translucent outer tank wall. In other implementations, the tank wall can be configured so that the outer tank wall 4304 has a substantially opaque color.

In the depicted implementation, one or more of the mouthpiece portion 4310, the tank portion 4302, the intermediate frame 4374, and the lower frame 4368 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 4300 further includes a heating member 4320 and a pair of electrical contacts 4325A, 4325B that are configured to electrically connect the heating member 4320 with the battery and/or control component of a control device. In the depicted implementation, the contacts 4325A, 4325B are located on opposite sides of the cartridge 4300 and are configured to be attached to at least one of the intermediate frame 4374, the lower frame 4168, and the tank portion 4302. Although in the depicted implementation the contacts 4325A, 4325B are configured to be attached to one or more of these components via a press-fit or snap fit attachment, in other implementations other forms of attachment are possible, including, for example, via an adhesive or via an insert molding process. In the depicted implementation, the heating member 4320 is located proximate the distal end 4308 of the tank portion 4302. In various implementations, the heating member 4320 may be located in and/or retained by the intermediate frame 4374 via a press-fit or snap fit attachment, although other forms of attachment are possible, including, for example, via an adhesive or via an insert molding process or being trapped by the lower frame 4368 against the intermediate frame 4374. In the depicted implementation, the electrical contacts 4325A, 4325B are constructed of a conductive material. Examples of conductive materials include, but are not limited to, copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

In the depicted implementation, the heating member 4320 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 4320 may be integrated with the first liquid transport element 4321. Other types of heating members may also be utilized, as noted above.

The cartridge 4300 of the depicted implementation also includes a liquid transport element 4321, at least a portion of which is configured to be located proximate the heating member 4320. In particular, in the depicted implementation the liquid transport element 4321 is located below the heating member 4320 and is configured to be captured by a feature of the lower frame 4368. In the depicted implementation, the liquid transport element 4321 has a relatively flat shape.

In various implementations, the liquid transport element 4321 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, a vaporization chamber 4340 is located in an area above the heating member 4320, and is defined, at least in part, by the intermediate frame 4374. In the depicted implementation, the cartridge also includes a separate vapor tube 4376 that is configured to extend between the vaporization chamber 4340 and the mouthpiece portion 4310. In the depicted implementation, the vapor tube 4376 may be constructed of a metal material (e.g., aluminum, stainless steel, metal alloys, etc.), although other materials are possible, including for example, a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof). In other implementations, the vapor tube may be constructed of other materials, including, for example, glass materials, ceramic materials (e.g., alumina, silica, mullite, silicon carbide, silicon nitride, aluminum nitride, etc.), composite materials, and/or any combinations thereof. As noted above, aerosol is generated in the vaporization chamber 4340 when the heating member 4320 heats at least a portion of the liquid composition contained in the first liquid transport element 4321. As such, when a user draws on the aerosol delivery device, aerosol from the vaporization chamber 4340 may be delivered to the user via the vapor tube 4376 and the exit portals 4315 of the mouthpiece portion 4310.

FIGS. 39 and 40 illustrate a cartridge in accordance with another implementation of the present disclosure. In particular, FIG. 39 illustrates an exploded perspective view of a cartridge 4500 according to an example implementation of the present disclosure, and FIG. 40 illustrates a partial cross-section perspective view of the cartridge 4500. In various implementations, a portion of the cartridge 4500 is configured to be removably coupled with a cartridge receiving chamber of a corresponding control device. In many aspects, the cartridge 4500 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 4500 of the depicted implementation includes a tank portion 4502 that is defined by an outer tank wall 4504 that includes a proximal end 4506 and a distal end 4508. As such, the tank portion 4502 may be characterized in that the tank wall 4504 is a sidewall that is continuous around the sides of the tank, with an open distal end 4508. In the depicted implementation, the open distal end 4508 of the tank portion 4502 is covered by a bottom cap 4572. Above the bottom cap 4572 is a lower frame 4568, and above the lower frame 4568 is an intermediate frame 4574. The tank portion 4502 is also configured to contain a liquid composition configured for vaporization (e.g., an e-liquid or aerosol precursor composition, as described above). The cartridge 4500 also includes a mouthpiece portion 4510 that is defined by an outer mouthpiece wall 4512 that includes a distal end 4516 and a proximal end 4514 with an exit portal 4515 defined therein. Although other configurations are possible, in the depicted implementation, the mouthpiece portion 4510 and the tank portion 4502 comprise the same part (referred to herein as the mouthpiece portion 4510/tank portion 4502). In some implementations, the outer mouthpiece wall 4512 of the mouthpiece portion 4510/tank portion 4502 may be created via an overmolding process with the mouthpiece portion 4510/tank portion 4502 (see e.g., FIG. 40).

In some implementations, the outer mouthpiece wall 4512 and/or the outer tank wall 4504 of the mouthpiece portion 4510/tank portion 4502 may be configured to be one of at least partially transparent or translucent so that the liquid composition contained therein is visible externally. As such, in some implementations, the entire outer mouthpiece wall 4512 and outer tank wall 4504 may be transparent or translucent. Alternatively, in some implementations, only the outer tank wall 4504 or only a single side of the outer tank wall 4504 may be transparent or translucent while the remaining portions of the outer tank wall may be substantially opaque. In some embodiments, the outer tank wall 4504 may be substantially opaque, and a strip extending from the proximal end 4506 of the tank 4502 to the distal end 4508 of the tank may be transparent or translucent. In further implementations, the outer tank wall 4504 may be colored. In some implementations, the color can be configured so that the liquid composition within the tank 4502 is still visible, such by using a transparent or translucent outer tank wall. In other implementations, the tank wall can be configured so that the outer tank wall 4504 has a substantially opaque color.

In the depicted implementation, one or more of the mouthpiece portion 4510/tank portion 4502, the intermediate frame 4574, the lower frame 4568, and the bottom cap 4572 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 4500 further includes a heating member 4520 and a pair of electrical contacts 4525A, 4525B that are configured to electrically connect the heating member 4520 with the battery and/or control component of a control device. In the depicted implementation, the contacts 4525A, 4525B are located on opposite sides of the cartridge 4500 and are configured to be attached to at least one of the bottom cap 4572, the lower frame 4568, and the intermediate frame 4574. Although in the depicted implementation the contacts 4525A, 4525B are configured to be attached to one or more of these components via a press-fit or snap fit attachment, in other implementations other forms of attachment are possible, including, for example, via an adhesive or via an insert molding process. In the depicted implementation, the heating member 4520 is located proximate the distal end 4508 of the tank portion 4502. In various implementations, the heating member 4520 may be located in and/or retained by the intermediate frame 4574 via a press-fit or snap fit attachment, although other forms of attachment are possible, including, for example, via an adhesive or via an insert molding process or being trapped by the lower frame 4568 against the intermediate frame 4574. In the depicted implementation, the electrical contacts 4525A, 4525B are constructed of a conductive material. Examples of conductive materials include, but are not limited to, copper, aluminum, platinum, gold, silver, iron, steel, brass, bronze, graphite, conductive ceramic materials, and/or any combination thereof. In some implementations, one or more of the electrical contacts may be constructed of one conductive material and may be plated with another conductive material, such as, for example, nickel and/or gold.

The bottom cap 4572 of the depicted implementation further includes a feature configured to retain a magnet 4570, which is configured to facilitate a mechanical connection between the cartridge 4500 and a control device. It should be noted that in other implementations, the bottom cap may include a component, such as, for example, a metal disk, configured to be attracted to a magnet located in the control device. In various implementations of the present disclosure, the magnet 4570 may comprise many different types of magnets, including rare earth magnets. For example, in some implementations, one or more magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more magnets may comprise Samarium Cobalt magnets (also known as SmCo magnets). In still other implementations, one or more magnets may comprise Ceramic/Ferrite magnets. In other implementations, one or more magnets may comprise Aluminum-Nickel-Cobalt (AlNiCo) magnets. In any of the foregoing implementations, one or more magnets may be plated and/or coated. For example, in some implementations, one or more magnets may be coated with nickel. In other implementations, one or more magnets may be coated with one or more of zinc, tin, copper, epoxy, silver and/or gold. In some implementations, one or more magnets may be coated with combinations of these materials. For example, in one implementation, one or more magnets may be coated with nickel, copper, and nickel again. In another implementation, one or more magnets may be coated with nickel, copper, nickel, and a top coating of gold.

In the depicted implementation, the heating member 4520 comprises a substantially flat heating member and may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 4520 may be integrated with the liquid transport element 4521. Other types of heating members may also be utilized, as noted above.

The cartridge 4500 of the depicted implementation also includes a liquid transport element 4521, at least a portion of which is configured to be located proximate the heating member 4520. In particular, in the depicted implementation the liquid transport element 4521 is located below the heating member 4520 and is configured to be captured by a feature of the lower frame 4568. In the depicted implementation, the liquid transport element 4521 has a relatively flat shape.

In various implementations, the liquid transport element 4521 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, a vaporization chamber 4540 is located in an area above the heating member 4520, and is defined, at least in part, by a portion of the intermediate frame 4574. In the depicted implementation, the cartridge also includes a vapor channel 4576 defined in the mouthpiece portion 4510/tank portion 4502 that extends downward from the distal end 4516 of the mouthpiece portion 4510 toward the intermediate frame 4574. The depicted implementation also includes a vapor tube cap 4578 that is configured to join the end of the vapor channel 4576 to the intermediate frame 4574. As noted above, aerosol is generated in the vaporization chamber 4540 when the heating member 4520 heats at least a portion of the liquid composition contained in the first liquid transport element 4521. As such, when a user draws on the aerosol delivery device, aerosol from the vaporization chamber 4540 may be delivered to the user via the vapor channel 4574 and the exit portal 4515 of the mouthpiece portion 4510.

FIGS. 41 and 42 illustrate a cartridge in accordance with another implementation of the present disclosure. In particular, FIG. 41 illustrates an exploded perspective view of a cartridge 4700 according to an example implementation of the present disclosure, and FIG. 42 illustrates a partial cross-section view of the cartridge 4700. In various implementations, a portion of the cartridge 4700 is configured to be removably coupled with a cartridge receiving chamber of a corresponding control device. In many aspects, the cartridge 4700 and a corresponding control device may have some similar configurations and may include some similar components (and some similar configuration and component variations) as those of the cartridge 300 and the control device 200 described above, which may not be repeated here. As such, reference is made to the pertinent discussions of these configurations and components (and configuration and component variations).

Referring to the figures, the cartridge 4700 of the depicted implementation includes a tank portion 4702 that is defined by an outer tank wall 4704 that includes a proximal end 4706 and a distal end 4708. As such, the tank portion 4702 may be characterized in that the tank wall 4704 is a sidewall that is continuous around the sides of the tank and includes an internal intermediate wall 4749, and an open distal end 4708 below the intermediate wall 4749. In the depicted implementation, the open distal end 4708 of the tank portion 4702 is covered by a bottom cap 4772. A lower frame 4768 is located above the bottom cap 4772. The tank portion 4702 is also configured to contain a liquid composition configured for vaporization (e.g., an e-liquid or aerosol precursor composition, as described above). The cartridge 4700 also includes a mouthpiece portion 4710 that is defined by an outer mouthpiece wall 4712 that includes a distal end 4716 and a proximal end 4714 with an exit portal 4715 defined therein. In the depicted implementation, the distal end 4716 of the mouthpiece portion 4710 is configured to be joined to the proximal end 4106 of the tank portion via a press or snap-fit connection; however, in other implementations, other attachment methods are possible (e.g., via adhesives, heat staking/welding, ultrasonic welding, etc.) or any combination thereof. In the depicted implementation, the distal end of the cartridge portion 4710 includes a sealing member 4717 that is disposed around at least a portion of the distal end 4716 of the mouthpiece portion 4710. In the depicted implementation, the sealing member 4717 is constructed of a thermoplastic elastomer (TPE) or a silicone material, although other materials are possible. In some implementation, the sealing member 4717 may be a separate part that is attached to the mouthpiece portion 4710 via a stretch-fit or via adhesive; however, in other implementations, the sealing member 4717 may be part of the mouthpiece portion 4710, such as an over molding process.

In some implementations, the outer tank wall 4704 may be configured to be one of at least partially transparent or translucent so that the liquid composition contained therein is visible externally. As such, in some implementations, the entire outer tank wall 4704 may be transparent or translucent. Alternatively, in some implementations, only a single side, or a portion (or portions) of one or more sides, of the outer tank wall 4704 may be transparent or translucent while the remaining portions of the outer tank wall may be substantially opaque. In some embodiments, the outer tank wall 4704 or a portion thereof may be substantially opaque, and a strip extending from the proximal end 4706 of the tank 4702 to the distal end 4708 of the tank may be transparent or translucent. In further implementations, the outer tank wall 4704 may be colored. In some implementations, the color can be configured so that the liquid composition within the tank 4702 is still visible, such by using a transparent or translucent outer tank wall. In other implementations, the tank wall can be configured so that the outer tank wall 4704 has a substantially opaque color.

In the depicted implementation, one or more of the mouthpiece portion 4710, the tank portion 4702, the lower frame 4768, and the bottom cap 4772 may be constructed of a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof), although other materials are possible. In other implementations, one or more of these components may be constructed of other materials, including, for example, metal materials (e.g., aluminum, stainless steel, metal alloys, etc.), glass materials, ceramic materials (e.g., alumina, silica, mullite, silicon carbide, silicon nitride, aluminum nitride, etc.), composite materials, and/or any combinations thereof.

As shown in figures, the cartridge 4700 further includes a heating member 4720. In the depicted implementation, the cartridge 4700 does not include separate electrical contacts. Rather, when coupled with the control device, electrical connectors (e.g., spring loaded pogo pins) in the control device are configured to extend through the bottom cap 4772 of the cartridge 4700 and make contact directly with exposed ends of the heating member 4720 such that the heating member 4720 is electrically connected to the battery and/or control component of the control device. In the depicted implementation, the heating member 4720 is located proximate the distal end 4708 of the tank portion 4702. In other implementations, the cartridge may include a pair of electrical contacts that are configured to electrically connect the heating member with the battery and/or control component of a control device. In such implementations, the contacts may be located on opposite sides of the cartridge and may be configured to be attached to at least one of the bottom cap, and the lower frame. In various such implementations, the contacts may be attached to the bottom cap via a press-fit or snap fit attachment, or another form of attachment, including, for example, via an adhesive or via an insert molding process. In various implementations, the heating member 4720 may be retained by the lower frame 4768 via a press-fit or snap fit attachment around the lower frame 4768, although other forms of attachment are possible, including, for example, via an adhesive or via an insert molding process.

In the depicted implementation, the heating member 4720 has a substantially flat heating surface and is wrapped around the lower frame 4768 such that it may be attached to the opposite surface thereof, such as via a pair of attachment tabs. In the depicted implementation, the heating member 4720 may be constructed of a metal material, such as a stainless steel material, including, but not limited to, 304, 304L, 316, or 316L stainless steel. In other implementations, the heating member may be constructed of a different material, such as, for example, stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si, Al)_2$), titanium, platinum, silver, palladium, alloys of silver and palladium, graphite and graphite-based materials (e.g., carbon-based foams and yarns). In further implementations, the heating member may be formed from conductive inks, boron doped silica, and/or ceramics (e.g., positive or negative temperature coefficient ceramics). In other implementations, the heating member may be printed on, embedded within, or otherwise integrated with a porous member. For example, in some implementations the heating member 4720 may be integrated with the liquid transport element 4721. Other types of heating members may also be utilized, as noted above.

The cartridge 4700 of the depicted implementation also includes a liquid transport element 4721, at least a portion of which is configured to be located proximate the heating member 4720. In particular, in the depicted implementation the liquid transport element 4721 is located below the heating member 4720 and is configured to be captured by a feature of the lower frame 4768. In the depicted implementation, the liquid transport element 4721 has a relatively flat shape, although any other shape is possible.

In various implementations, the liquid transport element 4721 may be formed of one or more materials configured for transport of a liquid, such as by capillary action. In some implementations, for example, one or both of the liquid transport elements may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the liquid transport elements thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, one or both of the liquid transport elements may be formed partially or completely from a porous monolith, such as a porous ceramic, a porous glass, or the like. Example monolithic materials that may be suitable for use according to embodiments of the present disclosure are described, for example, in U.S. patent application Ser. No. 14/988,109, filed Jan. 5, 2016, and U.S. Pat. No. 2014/0123989 to LaMothe, the disclosures of which are incorporated herein by reference in their entireties. In some implementations, the porous monolith may form a substantially solid wick.

As shown in the drawings, a vaporization chamber 4740 is located in an area above the heating member 4720, and is defined, at least in part, by a portion of the intermediate wall 4749 of the tank portion 4702. In the depicted implementation, the cartridge also includes a separate vapor tube 4774 that is configured to extend between the vaporization chamber 4740 and the mouthpiece portion 4710. In the depicted implementation, the vapor tube 4774 may be constructed of a metal material (e.g., aluminum, stainless steel, metal alloys, etc.), although other materials are possible, including for example, a molded polymer material, such as, for example, a molded plastic material (e.g., acrylonitrile butadiene styrene (ABS), polyethylene, polycarbonate, Polyamide (Nylon), high impact polystyrene, polypropylene, copolyester, polybutylene terephthlalate, and combinations thereof). In other implementations, the vapor tube may be constructed of other materials, including, for example, glass materials, ceramic materials (e.g., alumina, silica, mullite, silicon carbide, silicon nitride, aluminum nitride, etc.), composite materials, and/or any combinations thereof. As noted above, aerosol is generated in the vaporization chamber 4740 when the heating member 4720 heats at least a portion of the liquid composition contained in the first liquid transport element 4721. As such, when a user draws on the aerosol delivery device, aerosol from the vaporization chamber 4740 may be delivered to the user via the vapor tube 4774 and the exit portal 4715 of the mouthpiece portion 4710.

In some implementations, it will be appreciated that at least a portion of the atomizing member may be disposed within a space defined by a collar portion positioned between the tank portion and mouthpiece portion of a cartridge. Such configurations are illustrated, for example, in FIGS. 5A, 5B, 7A, 7B, 9, 11, 13, 14, 16, 17, 25, 26, 28, and 30. In some implementations, at least a portion of the atomizing member may be disposed proximate a distal end of a collar portion, at least of portion of the collar portion being positioned between the tank portion and mouthpiece portion of a cartridge. Such configurations are illustrated, for example, in FIGS. 19, 20, 22, and 24. In some implementations, the atomizing member may be disposed entirely distally from a distal end of the tank portion of a cartridge. Such configurations are illustrated, for example, in FIGS. 34 and 36, 38, 40, 42. In some such implementations, the atomizing member may be positioned proximate a distal end of the cartridge. Some implementations may include a hood feature (which may, or may not, comprise a curved hood feature), at least a portion of which may be disposed within a space defined by the mouthpiece portion of a cartridge. Such configurations are illustrated, for example, in FIGS. 5A, 5B, 7A, 7B, 19, 20, and 22. In some implementations that include a collar portion, the collar portion engages the mouthpiece portion on end, and the tank portion on a second end such that together they form a wall of the cartridge. Such configurations are illustrated, for example, in FIGS. 5A, 5B, 7A, 7B, 9, 11, 13, 14, 16, 17, 19, 20, 22, 24, 25, 26, 28, 30, and 34. In some implementations that include a collar portion, the collar portion supports and/or retains at least a portion of the electrical contacts of the cartridge. Such configurations are illustrated, for example, in FIGS. 4, 6, 8, 9, 10, 11, 12, 13, 14, 15, 16, 17, 18, 19, 20, 21, 22, 23, 24, 25, and 26.

Although some figures described herein illustrate a cartridge and a control device in a working relationship, it is understood that the cartridge and the control device may exist as individual components. Accordingly, any discussion otherwise provided herein in relation to the components in combination also should be understood as applying to the control device and the cartridge as individual and separate components.

In another aspect, the present disclosure may be directed to kits that provide a variety of components as described herein. For example, a kit may comprise a control device with one or more cartridges. A kit may further comprise a control device with one or more charging components. A kit may further comprise a control device with one or more batteries. A kit may further comprise a control device with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control devices may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:
1. An aerosol delivery device comprising:
   a control device that includes an outer housing defining an outer wall and having a proximal end and a distal end, the proximal end of the control device defining a cartridge receiving chamber, the control device further including a power source and a control component; and a cartridge that includes a mouthpiece portion and a tank portion, the mouthpiece portion and the tank portion having respective proximal and distal ends, the tank portion being configured to contain a liquid composition, the cartridge further including an atomizing member and a liquid transport element, wherein a portion of the cartridge is configured to be removably coupled with the cartridge receiving chamber of the control device, wherein at least a portion of the liquid transport element is located proximate the atomizing member, wherein the atomizing member is configured to vaporize the liquid composition to generate an aerosol, wherein at least a portion of the atomizing member is positioned above the proximal end of the tank portion, wherein the atomizing member comprises a heating member, wherein the heating member comprises a flat heating member, and wherein when installed in the cartridge, the heating member has a bowed shape.

2. The aerosol delivery device of claim 1, wherein the heating member is configured to heat the liquid composition to generate the aerosol.

3. The aerosol delivery device of claim 2, wherein the liquid transport element comprises a first liquid transport element, the cartridge further including a second liquid transport element, and wherein the second liquid transport element is configured to transport liquid to the first liquid transport element.

4. The aerosol delivery device of claim 3, wherein at least a portion of the heating member is positioned between the distal end of the mouthpiece portion and the proximal end of the tank portion.

5. The aerosol delivery device of claim 4, wherein the cartridge further includes a collar portion disposed between the mouthpiece portion and the tank portion, and wherein at least a portion of the heating member is located within the collar portion.

6. The aerosol delivery device of claim 4, wherein the second liquid transport element defines a longitudinal portion that intersects a curved transverse portion, and wherein a length of the longitudinal portion of the second liquid transport element is longer than a length of the transverse portion.

7. The aerosol delivery device of claim 6 further comprising a curved hood feature, wherein the curvature of the hood feature opposes the curvature of the heating member.

8. The aerosol delivery device of claim 4, wherein the second liquid transport element defines a longitudinal portion that intersects a curved transverse portion, and wherein a length of the transverse portion of the second liquid transport element is longer than a length of the longitudinal portion.

9. The aerosol delivery device of claim 8 further comprising a curved hood feature, wherein the curvature of the hood feature opposes the curvature of the heating member.

10. The aerosol delivery device of claim 4, wherein the second liquid transport element defines a longitudinal portion that intersects a transverse portion, and wherein a length of the longitudinal portion of the second liquid transport element is longer than a length of the transverse portion.

11. The aerosol delivery device of claim 1, wherein the cartridge further includes a collar portion disposed between the mouthpiece portion and the tank portion.

12. The aerosol delivery device of 11, wherein the heating member is located at least partially within the collar portion.

13. The aerosol delivery device of 12, further comprising a hood feature positioned proximate the heating member, wherein the hood feature is located at least partially within the mouthpiece portion.

* * * * *

UNITED STATES PATENT AND TRADEMARK OFFICE
CERTIFICATE OF CORRECTION

| | | |
|---|---|---|
| PATENT NO. | : 12,342,860 B2 | Page 1 of 1 |
| APPLICATION NO. | : 16/598505 | |
| DATED | : July 1, 2025 | |
| INVENTOR(S) | : Charles Jacob Novak, III et al. | |

It is certified that error appears in the above-identified patent and that said Letters Patent is hereby corrected as shown below:

In the Claims

In Column 102, Line 29, in Claim 12, delete "of" and insert -- of claim --.

In Column 102, Line 31, in Claim 13, delete "of" and insert -- of claim --.

Signed and Sealed this
Ninth Day of September, 2025

Coke Morgan Stewart
*Acting Director of the United States Patent and Trademark Office*